US011744884B2

(12) United States Patent
Galen et al.

(10) Patent No.: US 11,744,884 B2
(45) Date of Patent: Sep. 5, 2023

(54) **LIVE *SALMONELLA TYPHI* VECTORS ENGINEERED TO EXPRESS HETEROLOGOUS OUTER MEMBRANE PROTEIN ANTIGENS AND METHODS OF USE THEREOF**

(71) Applicants: University of Maryland, Baltimore, MD (US); National Research Council of Canada, Ottawa (CA)

(72) Inventors: James E. Galen, Eldersburg, MD (US); Thanh Pham, Baltimore, MD (US); Dacie R. Bridge, Blairsville, PA (US); Jin Yuan Wang, Silver Spring, MD (US); Wangxue Chen, Ottawa (CA)

(73) Assignees: UNIVERSITY OF MARYLAND, BALTIMORE, Baltimore, MD (US); NATIONAL RESEARCH COUNCIL OF CANADA, Ontario (CA)

( * ) Notice: Subject to any disclaimer, the term of this patent is extended or adjusted under 35 U.S.C. 154(b) by 0 days.

(21) Appl. No.: 16/614,261

(22) PCT Filed: May 15, 2018

(86) PCT No.: PCT/US2018/032662
§ 371 (c)(1),
(2) Date: Nov. 15, 2019

(87) PCT Pub. No.: WO2018/213242
PCT Pub. Date: Nov. 22, 2018

(65) Prior Publication Data
US 2020/0179501 A1 Jun. 11, 2020

Related U.S. Application Data

(60) Provisional application No. 62/506,078, filed on May 15, 2017.

(51) Int. Cl.
| | | |
|---|---|---|
| *A61K 39/02* | (2006.01) | |
| *A61K 39/05* | (2006.01) | |
| *A61K 39/112* | (2006.01) | |
| *A61K 39/108* | (2006.01) | |
| *A61K 39/00* | (2006.01) | |

(52) U.S. Cl.
CPC ...... *A61K 39/0275* (2013.01); *A61K 39/0266* (2013.01); *A61K 39/05* (2013.01); *A61K 2039/523* (2013.01); *A61K 2039/543* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 7,189,402 B1 | 3/2007 | Kitto | |
| 8,703,153 B2 * | 4/2014 | Telfer | A61P 37/04 424/258.1 |
| 2014/0357508 A1 | 12/2014 | Rakestraw | |
| 2015/0216959 A1 * | 8/2015 | Galen | A61K 39/0291 424/200.1 |
| 2016/0235834 A1 | 8/2016 | Bou Arévalo et al. | |

FOREIGN PATENT DOCUMENTS

WO WO-2006065139 A2 * 6/2006 ............ A61P 31/04

OTHER PUBLICATIONS

Ahmad et al. Trials in Vaccinology 5:53-60, 2016.*
Huang et al. Vaccine 33:4479-4485, 2015.*
Park et al. Faseb J. 26, 219-228, 2012.*
Senthilkumar et al. Asian Pacific Journal of Tropical Medicine (2014) 933-939.*
Farhadi et al. Int J Pept Res Ther (2015) 21:325-341.*
Wai et al. Cell, 2003, 115: 25-35.*
Elhenawy et al. mBio. Jul. 12, 2016; 7(4):00940-16.*
International Search Report from Appl. No.: PCT/US18/32662, dated Aug. 13, 2018.
Hartzell et al., Acinetobacter Pneumonia: A Review, MedGenMed, (2007), 9:(3)4.
Kuo et al., Multidrug-Resistant Acinetobacter BaumaNNii Bacteraemia: Clinical features, antimicrobial therapy and outcome, Clin MicroBiol and Infectious Diseases,(2006), 13:196-215.
Vila et al., Therapeutic Options for Acinetobacter Bumannii Infections, Expert Opin. Pharmacother, (2008), 9(4):587-599.
Fournier et al., The Epidemiology and Control of Acinetobacter baumannii in Health Care Facilities, Healthcare Epidemiology, (2006), 42:692-699.
Abbo et al., Impact of multi-drug-resistant Acinetobacter baumannii on clinical outcomes, Eur J Clin Microbiol Infect Dis (2007) 26:793-800.
Nosocomial Outbreak of Infection With Pan-Drug-Resistant Acinetobacter baumannii in a Tertiary Care University Hospital, Infection Control and Hospital Epidemiology, (2009), 30:257-263.
Taccone et al., Successful treatment of septic shock due to pan-resistant Acinetobacter baumannii using combined antimicrobial therapy including tigecycline, Eur J Clin Microbiol Infect Dis (2006) 25:257-260.
Mcconnell et al., Acinetobacter baumannii: human infections, factors contributing to pathogenesis and animal models, FEMS Microbiol Rev, (2013), 37:130-155.

(Continued)

*Primary Examiner* — Oluwatosin A Ogunbiyi
(74) *Attorney, Agent, or Firm* — Nevrivy Patent Law Group P.L.L.C.

(57

(56) References Cited

OTHER PUBLICATIONS

Garcia-Quintanilla et al., Emerging therapies for multidrug resistant Acinetobacter baumannii, Trends in Microbiology Mar. 2013, 21:157-163.
Bentancor et al., Evaluation of the Trimeric Autotransporter Ata as a Vaccine Candidate against Acinetobacter baumannii Infections, Infection and Immunity, (2012), 80:3381-3388.
Luo et al., Active and Passive Immunization Protects against Lethal, Extreme Drug Resistant-Acinetobacter baumannii Infection, PLoS ONE, (2012), 7:1-11.
Mcconnell et al. Active and passive immunization against Acinetobacter baumannii using an inactivated whole cell vaccine. Vaccine, (2011), 29:1-5.
Fattahian et al., Protection against Acinetobacter baumannii infection via its functional deprivation of biofilm associated protein (Bap), Microbial Pathogenesis, (2011), 51:402-406.
Russo et al., The K1 Capsular Polysaccharide of Acinetobacter baumannii Strain 307-0294 Is a Major Virulence Factor, Infection and Immunity, (2010), 3993-4000.
Bentancor et al., Poly-N-Acetyl-β-(1-6)-Glucosamine Is a Target for Protective Immunity against Acinetobacter baumannii Infections, Infection and Immunity, (2012) 80:651-656.
Mcconnell et al., Vaccination with Outer Membrane Complexes Elicits Rapid Protective Immunity to Multidrug-Resistant Acinetobacter baumannii, Infection and Immunity, (2011) 79:518-526.
Lin et al., Acinetobacter baumannii rOmpA Vaccine Dose Alters Immune Polarization and Immunodominant Epitopes, Vaccine, (2013) 31:313-318.

* cited by examiner

CVD *910ssb ompA^St ompA^Ab* (pSEC10)

CVD *910ssb ompA$^{St*}$ompA$^{Ab*}$ompW$^{Ab}$(pSEC10)*

1. blank
2. CVD 910
3. CVD 910(pSEC10)
4. 910$\Delta ompA^{St}$(pSEC10)
5. 910$\Delta ompA^{St}guaBA::ompA^{Ab}$(pSEC10)

LIVE *SALMONELLA TYPHI* VECTORS ENGINEERED TO EXPRESS HETEROLOGOUS OUTER MEMBRANE PROTEIN ANTIGENS AND METHODS OF USE THEREOF

CROSS-REFERENCE TO RELATED APPLICATIONS

This application claims the benefit of U.S. Provisional Appl. No. 62/506,078 filed on May 15, 2017, the contents of which are hereby incorporated by reference in their entirety.

STATEMENT OF FEDERALLY SPONSORED RESEARCH AND DEVELOPMENT

This invention was made with government support under the Grant Number AI095309 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 34,406 Byte ASCII (Text) file named "Sequence_listing_ST25.txt," created on May 14, 2018.

FIELD OF THE INVENTION

The field of the invention relates generally to the field of medicine, molecular biology, in particular vaccine technology.

BACKGROUND OF THE INVENTION

*Acinetobacter baumannii* and *Klebsiella pneumoniae* are Gram-negative non-spore forming bacteria frequently associated with nosocomial infections in acute and chronic intensive care settings including bacteremia and pneumonia[7-12]. Of great concern to public health is the steady rise in the frequency of multidrug-resistant (MDR) clinical isolates that have become resistant to most classes of antibiotics currently available, seriously compromising treatment therapies for patients and drastically increasing the morbidity and mortality associated with infection. The Centers for Disease Control and Prevention has classified carbapenem-resistant *K. pneumoniae* as an urgent threat to public health, and has further classified multidrug-resistant *Acinetobacter* as a serious threat to public health[13]. In addition, the World Health Organization has now issued a report raising serious concerns over the lack of new antibiotics under development to combat the growing threat of antimicrobial resistance[14]. In spite of the fact that effective antibiotic treatment therapies are rapidly dwindling, no licensed vaccines against any of these pathogens are currently available.

Antibiotic resistance in *A. baumannii* has been shown to arise through a variety of genetic mechanisms including acquisition of integron cassettes encoding multiple resistance genes, as well as loss-of-function deletion mutations in which synthesis of protein targets of antibiotics are spontaneously deleted[8,15-17]. The remarkable ease with which the chromosome of *A. baumannii* can both gain and lose gene function to promote persistence and sustained growth has been referred to as genome plasticity. Such genetic drift poses a significant challenge not only to therapeutic treatment of potentially life threatening infections, but also for the development of vaccines targeting humoral immunity to antigenic targets, which ideally must be highly conserved among a wide variety of clinical isolates in order to achieve protective efficacy against disease.

Loss-of-function mutations, upregulation of efflux systems, and acquisition of antibiotic resistance modules through integrons, transposons, and resistance plasmids have also been reported as significant confounding factors to the treatment of *K. pneumoniae* infections, which has significantly reduced the treatment options available for reducing morbidity and mortality associated with bacteremia, pneumonia, and urinary tract infections[18,19]. Multilocus sequence typing has identified ST258 as a hypervirulent carbapenemase-producing clone of *K. pneumoniae* with global dissemination especially in nosocomial settings[20]. Optimum treatment strategies for ST258 infections remain to be firmly established; combined therapies with several antibiotics have shown promise, although use of combinations that include colistin (polymyxin E) risk serious side effects including nephrotoxicity[21] and resistance to this last resort antibiotic is increasing[22-25].

The genome plasticity that rapidly confers antibiotic resistance to clinical isolates of *A. baumannii* and *K. pneumoniae* strongly suggests that discovery of new classes of antibiotics may not provide much needed long-term solutions for consistently effective therapeutic interventions against potentially lethal infections. Therefore, development of efficacious multivalent vaccines against these pathogens presents a very attractive prophylactic alternative to costly treatments with steadily increasing failure rates. Although specific correlates of protection have yet to be defined, experimental animal models have demonstrated that eliciting immunity against outer membrane surface antigens confers significant protection against challenge with clinical isolates of *A. baumannii* and *K. pneumoniae*.

The protective efficacy of outer membrane antigens is clearly supported with experimental data from *A. baumannii*. When purified outer membrane vesicles (OMVs) were used as acellular vaccines, pathogen-specific antibody responses were observed in parenterally immunized mice, with complete protection achieved against septic challenge with fully virulent MDR clinical strains[26,27]. It was later shown that when using genetically engineered OMVs from *A. baumannii* in which synthesis of lipid A was inactivated (resulting in LPS deficient strains), full protection against septic challenge was once again achieved, further supporting the role of outer membrane antigens in protection against disease[28]. When acellular vaccines comprised only of proteins extracted from the bacterial outer membrane, termed outer membrane complexes (OMCs), were used to vaccinate mice intramuscularly, full protection against MDR challenge strains was again achieved, paving the way for the development of fully characterized subunit vaccines comprised of specific outer membrane proteins[29].

As with *A. baumannii*, the protective efficacy of outer membrane antigens against infections with *K. pneumoniae* has also been demonstrated using purified outer membrane vesicles as immunogens. Protection against lethal challenge was achieved in mice immunized intraperitoneally with purified OMVs from *K. pneumoniae* in a bacterial sepsis challenge model using a K1-encapsulated strain[30]. In addition, protection was also demonstrated using sera and splenocytes in adoptive transfer experiments, indicating both antibody-mediated humoral and T-cell-mediated cellular protective mechanisms[30]. It has also been reported that antibody-independent protection can be achieved through activation of Th17 cells against *K. pneumoniae* regardless of capsular polysaccharide serotype; protection was clearly demonstrated in B cell-deficient mice immunized intranasally with purified OMPs from a *K. pneumoniae* serotype K2 capsular type and challenged intratracheally with a *K. pneumoniae* K1 strain[31]. Given that over 78 distinct capsular types have been identified in *K. pneumoniae*[32], capsule-independent protection could significantly improve the efficacy of vaccines against infection with MDR *K. pneumoniae*.

Encouraging results with protective subunit vaccines targeting *A. baumannii* and *K. pneumoniae* outer membrane proteins have recently come from efforts focusing on monomeric eight stranded β-barrel outer membrane proteins[33]. These proteins are generally comprised of eight to ten hydrophobic transmembrane domains (β-barrels) interspersed with at least 4 surface exposed loops that influence biological function[33,34] To date, only two β-barrel proteins have been reported to be highly immunogenic subunit vaccines, capable of conferring excellent protective immunity in mice lethally challenged with MDR *A. baumannii* clinical isolates: AbOmpA[35,36] and AbOmpW[37]. AbOmpA is a 38 kDa non-lipidated β-barrel protein which is highly conserved at the amino acid level among MDR clinical isolates; to our knowledge, no clinical isolate without the ompA gene has yet been identified despite the plasticity of the genome. In addition, AbOmpA is the most highly expressed protein present on the surface of *A. baumannii*[38,39]. AbOmpA appears to function as an adherence factor[40,41]. Quantitative reverse-transcription PCR (qRT-PCR) of *A. baumannii* clinical isolates demonstrated that over-expression of OmpA was a significant risk factor associated with pneumonia, bacteremia, and death[42]. Subunit vaccines comprised of adjuvanted AbOmpA elicited AbOmpA-specific serum IgG antibody responses in subcutaneously immunized mice, which recognized native AbOmpA in purified outer membranes from *A. baumannii* and conferred partial protection against challenge[35,36]. The only other non-lipidated OMP reported to be highly conserved among *A. baumannii* clinical isolates, and capable of conferring protection against septic challenge with MDR isolates, is the 20 kDa outer membrane protein W (AbOmpW). A subunit vaccine comprised solely of purified and refolded AbOmpW elicited AbOmpW-specific serum IgG responses in mice immunized subcutaneously with three adjuvanted doses spaced two weeks apart[37]; excellent protection was observed in both actively and passively immunized mice challenged with MDR *A. baumannii* clinical isolates using a septic challenge model[37].

*K. pneumoniae* OmpA (KpOmpA) has been reported to confer resistance to antimicrobial peptides[43], and inactivation reduces virulence in both the murine pneumonia[44] and urinary tract models of infection[45]. Data supporting the targeting of KpOmpA as a vaccine immunogen comes from immunoproteomic analysis, in which KpOmpA and KpOmpW were identified as among the most frequently and consistently recognized proteins using sera from patients with acute *K. pneumoniae* infections, indicating that these two proteins are expressed and immunologically detected during human infections and could therefore be excellent vaccine antigens; these proteins were not identified when using sera from healthy individuals[46]. Perhaps more significantly, KpOmpA has been reported to function as a pathogen-associated molecular pattern (PAMP) capable of activating dendritic cells to produce cytokines via the Toll-like receptor 2 and enhance innate immunity[47-51]. The protective efficacy of KpOmpA has been demonstrated in mice parenterally vaccinated with a DNA vaccine encoding KpOmpA and subsequently challenged intraperitoneally with a lethal dose of *K. pneumoniae*; in mice immunized intramuscularly with the DNA vaccine, ~60% protection was observed, while ~75% protection was observed in mice vaccinated intradermally[52]. However, in contrast to vaccines against *A. baumannii*, a subunit vaccine targeting KpOmpW remains to be tested for protective efficacy in an experimental challenge model with *K. pneumoniae*.

*Salmonella* has been one of the organisms most studied for use as a mucosal live carrier vaccine delivering foreign antigens to the immune system. A number of attenuated strains expressing heterologous antigens have been produced and successfully tested in animal models and in humans. Over the years, we have developed several attenuated vaccine strains of *Salmonella* derived from serovar Typhi[57-59]. Our attenuated strain advancing the furthest in clinical trials is CVD 908-htrA which was found to be well tolerated in clinical trials at doses up to $5\times10^9$ CFU in the absence of bacteremia[57]. In addition, CVD 908-htrA elicited a broad array of immune responses to S. Typhi antigens that included intestinal secretory IgA antibodies, serum IgG antibodies, and T cell-mediated immunity[57,60]. The ability of CVD 908-htrA to successfully deliver foreign antigens to the human immune system was clearly demonstrated in a recent clinical trial in which volunteers were orally primed with a single dose of attenuated CVD 908-htrA live carrier vaccine presenting two plasmid-encoded outer membrane protein antigens from *Pseudomonas aeruginosa*[61]; all volunteers were then boosted intramuscularly 4 weeks later with a single dose of alum-adjuvanted antigens. These vaccinees mounted *P. aeruginosa*-specific serum IgG responses comparable to subjects in the study immunized with 3 intramuscular doses of adjuvanted subunit vaccine alone; however, orally primed volunteers also mounted *P. aeruginosa*-specific mucosal pulmonary IgA responses that were not observed in systemically immunized subjects[61]. Interestingly, in an additional cohort of volunteers vaccinated with live carrier vaccines derived from the more attenuated licensed vaccine Ty21a, 3 oral priming doses in addition to the systemic booster dose were required to elicit immune responses comparable to those of volunteers receiving only a single priming dose of CVD 908-htrA plus subunit boost.

Over the years, we have developed efficient plasmid-based[62-64] and chromosomal systems[65,66] for expression of immunogenic levels of foreign antigens in attenuated S. Typhi carrier vaccines. Our low copy number plasmid-based expression systems do not involve the use of antibiotic resistance genes for stable introduction into our carrier strains. Rather, all expression plasmids encode the single stranded binding protein (SSB), essential for DNA replication, recombination, and repair[67,68]; these novel plasmids are designed to complement an otherwise lethal deletion of ssb from the chromosome of our carrier vaccines, thus assuring retention of these plasmids in vivo after administration of the vaccine. We have also developed chromosomal expression systems designed to synchronize expression of foreign antigens with the growth phase of the carrier strain to avoid over-attention of carriers by inappropriately high levels of antigen expression in vivo[65,69]. However, in addition to ensuring stable expression of foreign antigens, we have also enhanced efficient delivery of these foreign antigens to immune inductive sites to improve antigen-specific immunity. It is now clear that the manner in which foreign antigens are delivered to the immune system can have a profound impact on the resulting immune responses and ultimately the success of a live carrier vaccine. The induction and extent of mucosal, humoral, and cellular immunity can be significantly influenced by whether foreign antigens are expressed cytoplasmically or exported out of the live carrier. Antigen-specific humoral immunity can increase significantly when antigens are exported either to the bacterial surface or extracellularly into the surrounding milieu, rather than remaining in the cytoplasm[62,63,70]. Therefore, we developed a novel antigen export system in which foreign antigen domains are fused to the carboxyl terminus of an endogenous outer membrane protein of S. Typhi called cytolysin A (ClyA); surface expression of ClyA fusions leads to the export of fused foreign domains out of carrier vaccines via outer membrane vesicles[62]. We have successfully used this antigen delivery strategy to develop a promising carrier-based anthrax vaccine[62,63].

The lack of a practical small animal model for evaluating the immunogenicity of S. Typhi-based live carrier vaccines prior to clinical trials seriously impeded live carrier vaccine development for years. S. Typhi is a highly host-restricted human pathogen that is incapable of inducing a progressive systemic infection in conventional or germfree animal models by either oral or parenteral inoculation[71,72]. However, our laboratory was the first to develop a murine intranasal model of immunogenicity for the pre-clinical assessment of S. Typhi-based live carrier vaccines[73]. Over the years, a number of live carrier vaccine candidates have been tested using this model, and the success of intranasal immunization with S. Typhi vaccine vectors has been demonstrated in both mice and non-human primates. We have shown the induction of antigen-specific serum antibodies in mice against a variety of bacterial toxins[74-77], as well as serum neutralizing antibody responses against anthrax toxin in both mice[64] and non-human primates[63]. Mucosal and T cell mediated immune responses were also induced against a variety of antigens using different vaccine constructs[78,80]. Most importantly, these responses are very similar to those seen in humans[81,82]. The intranasal model of immunogenicity is the only well-characterized animal model available for pre-clinical testing of attenuated S. Typhi live carrier vaccine candidates, and has been used to advance at least 3 live carrier vaccines into clinical trials[83-86].

There is a need to develop new compositions and methods for enhancing immunogenicity and protective immunity against mucosal pathogens. The present invention satisfies this need and provides additional advantages as well.

This background information is provided for informational purposes only. No admission is necessarily intended, nor should it be construed, that any of the preceding information constitutes prior art against the present invention.

SUMMARY OF THE INVENTION

It is to be understood that both the foregoing general description of the embodiments and the following detailed description are exemplary, and thus do not restrict the scope of the embodiments.

In one aspect, the invention relates to designing and remodeling of the outer membrane of an attenuated S. Typhi-based live vector vaccine into an antigen presentation platform in which protective outer membrane antigens, such as one or more antigens from *Acinetobacter baumannii* or *Klebsiella pneumoniae*, are mucosally delivered to immune inductive sites to elicit protection against systemic and mucosal disease. Mucosal delivery of recombinant outer membrane vesicles (rOMVs) via a live vector vaccine offers significant advantages over conventional acellular OMV-based vaccination strategies including: 1] sustained in vivo delivery to mucosal inductive sites, and 2] delivery of rOMVs enriched in properly folded protective antigens.

In another aspect, the invention provides a method of inducing an immune response in a subject in need thereof, comprising administering to the subject an immunologically-effective amount of a live *Salmonella enterica* Typhi vector that has been engineered to express one or more heterologous antigens from a pathogen, wherein the heterologous antigen comprises an outer membrane protein, an antigenic fragment thereof or a variant thereof, wherein the antigen is delivered to a mucosal tissue of the subject by an outer membrane vesicle produced by the *Salmonella* Typhi vector.

In another aspect, the invention provides a method of inducing an immune response in a subject in need thereof, comprising administering to the subject an immunologically-effective amount of isolated recombinant outer membrane vesicles from *Salmonella* Typhi comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen, wherein the outer membrane vesicle is delivered to a mucosal tissue of the subject.

In another aspect, the invention provides an attenuated S. Typhi-bacterial live vector vaccine strain that exhibits enhanced delivery of an antigen to the immune system through increased formation of recombinant outer membrane vesicles (rOMVs). In some embodiments, the S. Typhi-bacterial live vector over-expresses either a ClyA protein and/or the lipid A deacylase PagL which induces extensive OMV formation when over-expressed in *Salmonella*.

In another aspect, the invention provides a live *Salmonella* Typhi vector that has been engineered to express one or more heterologous antigens from a pathogen, wherein the heterologous antigen comprises an outer membrane protein, an antigenic fragment thereof or a variant thereof, wherein the *Salmonella* Typhi vector is capable of delivering the antigen to a mucosal tissue when administered to a subject. In some embodiments, the pathogen is selected from *Acinetobacter baumannii* and *Klebsiella pneumoniae*.

In another aspect, the invention provides a composition comprising a combination of the live *Salmonella* Typhi vectors, wherein a first *Salmonella* Typhi vector expresses i) OmpA, an antigenic fragment thereof or a variant thereof from *Acinetobacter baumannii*; and ii) OmpW, an antigenic fragment thereof or a variant thereof from *Acinetobacter baumannii*; and a second *Salmonella* Typhi vector expresses i) OmpA, an antigenic fragment thereof or a variant thereof from *Klebsiella pneumoniae*; and ii) OmpW, an antigenic fragment thereof or a variant thereof from *Klebsiella pneumoniae*.

In another aspect, the invention provides an attenuated S. Typhi-bacterial live vector vaccine strain expressing the protective outer membrane protein OmpA from *A. baumannii* or *Klebsiella pneumoniae*. In one embodiment, the S. Typhi elicits protective efficacy against *A. baumannii* or *Klebsiella pneumoniae*. In some embodiments, S. Typhi-bacterial live vector comprises a synthetic gene cassette encoding OmpA integrated into the chromosome. In some embodiments, the protective antigen is expressed on the surface of the live vector vaccine. In some embodiments, the vaccine provides protective efficacy against intranasal and/or systemic challenge of the *A. baumannii* clinical isolate LAC-4. In one embodiment, the S. Typhi-bacterial live vector vaccine strain is derived from S. Typhi Ty2.

In another aspect, the invention provides an attenuated S. Typhi-bacterial live vector vaccine strain expressing the protective outer membrane protein OmpA from *A. baumannii* or *Klebsiella pneumoniae*, wherein the S. Typhi-bacterial live vector exhibits enhanced delivery of OmpA to the immune system through increased formation of recombinant outer membrane vesicles (rOMVs). In some embodiments, the S. Typhi-bacterial live vector over-expresses either a ClyA protein, the lipid A deacylase PagL or both. In some embodiments, there is increased extracellular export of OmpA.

In another aspect, the invention provides an attenuated S. Typhi-bacterial bivalent live vector vaccine strain expressing the outer membrane proteins OmpA and OmpW from *A. baumannii* or *Klebsiella pneumoniae*. In some embodiments, the S. Typhi-bacterial live vector over-expresses rOMVs enriched for both OmpA and OmpW. In some embodiments, the S. Typhi-bacterial bivalent live vector over-expresses either a ClyA protein responsible for naturally inducing OMV formation in S. Typhi, the lipid A deacylase PagL, or both.

In another aspect, the invention provides a composition comprising isolated recombinant outer membrane vesicles from *Salmonella* Typhi comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

Figure 1:
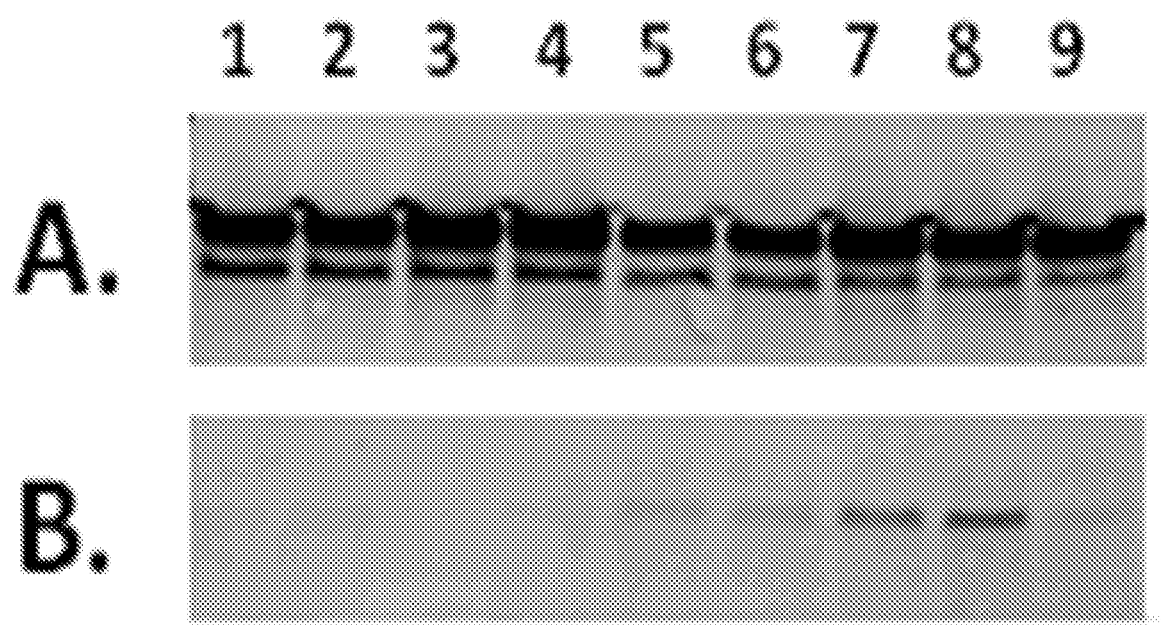
FIG. 1. Western immunoblots of whole cell lysates (A) and culture supernatants (B) from isogenic attenuated S Typhi CVD 910 strains expressing AbOmpA. Samples from approximately $1 \times 10^8$ CFU of exponentially growing cultures were analyzed using polyclonal mouse antibody raised against purified AbOmpA; replicate paired samples were run to correct for variations in loading. Lanes 1-2: 910OmpAAb (pSEC10); Lanes 3-4: 910OmpAAb; Lanes 5-6: 910 ΔOmpAStOmpAAb(pSEC10); Lanes 7-8: 910 ΔOmpAStOmpAAb; Lane 9: 910ssb(pSEC10SOmpAAb).

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual*, 2$^{nd}$ edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

While rapid identification of pathogens, novel therapeutic interventions, and passive immunization have critical roles in disease control, none can substitute for pre-existing protective immunity. Mucosally delivered bacterial live vector vaccines represent a practical and effective strategy for immunization. In this approach, genes that encode protective antigens of unrelated pathogens are expressed in an attenuated vaccine strain and delivered mucosally to generate relevant local and systemic immune responses.

In some embodiments, the invention provides a live *Salmonella* Typhi vector that has been engineered to express one or more heterologous antigens from a pathogen, wherein the heterologous antigen comprises an outer membrane protein, an antigenic fragment thereof or a variant thereof, wherein the *Salmonella* Typhi vector is capable of delivering the antigen to a mucosal tissue when administered to a subject. In some embodiments, the invention provides a bivalent vaccine against pneumonic and systemic infections caused by *Acinetobacter baumannii* or *Klebsiella pneumoniae*.

In some embodiments, the invention provides an attenuated S. Typhi-bacterial live vector vaccine strain that exhibits enhanced delivery of an antigen to the immune system through increased formation of recombinant outer membrane vesicles (rOMVs). In some embodiments, the S. Typhi-bacterial live vector over-expresses either a ClyA protein responsible for naturally inducing OMV formation in S. Typhi, and/or the lipid A deacylase PagL which induces extensive OMV formation when over-expressed in *Salmonella*.

In some embodiments, the invention provides a composition comprising a combination of the live *Salmonella* Typhi vectors, wherein a first *Salmonella* Typhi vector expresses i) OmpA, an antigenic fragment thereof or a variant thereof from *Acinetobacter baumannii*; and ii) OmpW, an antigenic fragment thereof or a variant thereof from *Acinetobacter baumannii*; and a second *Salmonella* Typhi vector expresses i) OmpA, an antigenic fragment thereof or a variant thereof from *Klebsiella pneumoniae*; and ii) OmpW, an antigenic fragment thereof or a variant thereof from *Klebsiella pneumoniae*.

In some embodiments, the invention provides a composition comprising isolated recombinant outer membrane vesicles from *Salmonella* Typhi comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen.

In some embodiments, the invention provides a composition comprising a combination of isolated recombinant outer membrane vesicles from *Salmonella* Typhi, wherein a first isolated recombinant outer membrane vesicle comprises i) OmpA, an antigenic fragment thereof or a variant thereof from *Acinetobacter baumannii*; and ii) OmpW, an antigenic fragment thereof or a variant thereof from *Acinetobacter baumannii*; and a second isolated recombinant outer membrane vesicle comprises i) OmpA, an antigenic fragment thereof or a variant thereof from *Klebsiella pneumoniae*; and ii) OmpW, an antigenic fragment thereof or a variant thereof from *Klebsiella pneumoniae*, wherein the *Salmonella* Typhi has been engineered to express the heterologous antigens.

In some embodiments, the invention provides genetically engineered attenuated strains of S. Typhi as live vaccine platforms for delivery of protective outer membrane proteins to protect against pathogens such as *A. baumannii* or *K. pneumoniae*. These antigens will be expressed on the surface of live vaccines after induction of synthesis in vivo, and will be exported from the surface to immune inductive sites via a unique inducible OMV-mediated export system, as described in more detail below. In some embodiments, the live vaccines will target OmpA from *A. baumannii* and *K. pneumoniae*, which each encode non-cross-reactive versions of OmpA that are highly conserved across each individual species. In some embodiments, the live vaccines comprise OmpW from *A. baumannii* or *K. pneumoniae* or both OmpA and OmpW from *A. baumannii* or *K. pneumoniae*.

Without being bound by theory, delivery of both OmpA and OmpW via rOMVs is expected to preserve the proper conformation of these hydrophobic membrane proteins in vivo to achieve optimum protective efficacy against infection. The approach offers the potential to elicit mucosal immunity against a mucosal pathogen, an advantage not offered by purified subunit vaccines which are administered parenterally to elicit humoral immunity. In some embodiments, the vaccines are delivered via an intranasal route. In some embodiments, the vaccine provides protective immunity against hypervirulent *A. baumannii* LAC-4, for example, using the pneumonic intranasal challenge model.

The *Salmonella* Typhi strain that can be used in the present invention as a vaccine is not limiting. For example, it can include any particular strain that has been genetically attenuated from the original clinical isolate Ty2. Any attenuated *Salmonella* Typhi strain derived from Ty2 can be used as a live vector in accordance with the invention. Non-limiting, exemplary attenuated *Salmonella* Typhi strains include S. Typhi Ty21a, CVD 908, S. Typhi CVD 909, CVD 908-htrA, CVD 915, and CVD 910. In some embodiments, the S. Typhi strain can carry one or more additional chromosomal mutations in an essential gene that is expressed on a plasmid. In some embodiments, the plasmid also encodes a heterologous protein in accordance with the invention, enabling selection and stabilization of the plasmid and preventing loss in S. Typhi. In some embodiments, the S. Typhi strain carries a mutation in the ssb gene which is encoded on a selection expression plasmid.

If heterologous antigens or other proteins are overexpressed using plasmids, plasmid stability can be a key factor in the development of high quality attenuated S. Typhi vaccines. Plasmidless bacterial cells tend to accumulate more rapidly than plasmid-bearing cells. One reason for this increased rate of accumulation is that the transcription and translation of plasmid genes imposes a metabolic burden which slows cell growth and gives plasmidless cells a competitive advantage. Furthermore, foreign plasmid gene products are sometimes toxic to the host cell. Thus, it is advantageous for the plasmid to be under some form of selective pressure, in order to ensure that the encoded antigens are properly and efficiently expressed, so that a robust and effective immune response can be achieved.

In some embodiments, the plasmid is selected within S. Typhi using a non-antibiotic selection system. For example, the plasmid can encode an essential gene that complements an otherwise lethal deletion/mutation of this locus from the live vector chromosome. Exemplary non-antibiotic expression plasmids that can be used in the invention are described herein and further plasmid systems which can be used in the invention are described, for example, in U.S. Patent Appl. Pub. No. 20070281348, U.S. Pat. Nos. 7,141,408, 7,138,112, 7,125,720, 6,977,176, 6,969,513, 6,703,233, and 6,413,768, which are herein incorporated by reference.

In one embodiment, a non-antibiotic genetic stabilization and selection system for expression plasmids is engineered to encode single-stranded binding protein (SSB), an essential protein involved in DNA replication, recombination, and repair which can be deleted from the S. Typhi live vector chromosome (Lohman T M, Ferrari M E. *Escherichia coli* single-stranded DNA-binding protein: multiple DNA-binding modes and cooperativities. Annu Rev Biochem. 1994; 63:527-570; Chase J W, Williams K R. Single-stranded DNA binding proteins required for DNA replication. Annu Rev Biochem. 1986; 55:103-136; Galen J E, Wang J Y, Chinchilla M, Vindurampulle C, Vogel J E, Levy H, Blackwelder W C, Pasetti M F, Levine M. A new generation of stable, nonantibiotic, low-copy-number plasmids improves immune responses to foreign antigens in *Salmonella enterica* serovar Typhi live vectors. Infect Immun. 2010 January; 78(1):337-47). In some embodiments, the plasmid expression vector for S. Typhi encodes a single-stranded binding protein (SSB). In some embodiments, the expression vector is pSEC10S.

In some embodiments of the invention, expression plasmids are employed in which both the random segregation and catalytic limitations inherent in non-antibiotic plasmid selection systems have been removed. The segregation of these plasmids within S. Typhi live vectors is improved using an active partitioning system (parA) for S. Typhi CVD 908-htrA (Galen, J. E., J. Nair, J. Y. Wang, S. S. Wasserman, M. K. Tanner, M. Sztein, and M. M. Levine. 1999. Optimization of plasmid maintenance in the attenuated live vector vaccine strain *Salmonella* Typhi CVD 908-htrA. Infect. Immun. 67:6424-6433). In some embodiments, dependence on catalytic enzymes is avoided by using a plasmid selection/post-segregational killing system based on the ssb gene.

A solution to the instability of multicopy plasmids and the foreign antigens they encode is to integrate foreign gene cassettes into the chromosome of the live vector. However, the drop in copy number becomes both an advantage and a disadvantage; while the reduced copy number will certainly reduce the metabolic burden associated with both the multicopy plasmid itself and the encoded foreign protein(s), this reduction in foreign antigen synthesis ultimately leads to reduced delivery of these antigens to the host immune system and possibly reduced immunogenicity. This explanation could account for why in clinical trials serum immune responses to chromosomally encoded antigens have to date been modest. (Gonzalez C, Hone D, Noriega F R et al. *Salmonella* Typhi vaccine strain CVD 908 expressing the circumsporozoite protein of *Plasmodium falciparum*: strain construction and safety and immunogenicity in humans. J Infect Dis. 1994; 169:927-931; Khan. S, Chatfield S, Stratford R et al. Ability of SPI2 mutant of S. Typhi to effectively induce antibody responses to the mucosal antigen enterotoxigenic *E. coli* heat labile toxin B subunit after oral delivery to humans. Vaccine. 2007; 25:4175-4182).

In some embodiments, the pathogen is *Acinetobacter baumannii*. In some embodiments, the pathogen is *Klebsiella pneumoniae*. In some embodiments, the pathogen is a bacterial or viral pathogen. In some embodiments, the pathogen is selected from the group consisting of *Streptococcus pneumonia, Neisseria meningitidis, Haemophilus influenza, Klebsiella* spp., *Pseudomonas* spp., *Salmonella* spp., *Shigella* spp., and Group *B streptococci, Bacillus anthracis* adenoviruses; *Bordetella pertussus*; Botulism; bovine rhinotracheitis; *Brucella* spp.; *Branhamella catarrhalis*; canine hepatitis; canine distemper; Chlamydiae; Cholera, coccidiomycosis; cowpox; tularemia; filoviruses, arenaviruses; bunyaviruses; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; *Burkholderia mallei*; Globulin, *Haemophilus* influenza type b; *Haemophilus influenzae; Haemophilus pertussis; Helicobacter pylori; Hemophilus* spp.; hepatitis; hepatitis A; hepatitis B; Hepatitis C; herpes viruses, HIV, HIV-1 viruses, HIV-2 viruses, HTLV, Influenza, Japanese encephalitis; *Klebsiellae* spp. *Legionella pneumophila; leishmania*; leprosy; lyme disease, malaria immunogen; measles, meningitis; meningococcal; Meningococcal Polysaccharide Group A, Meningococcal Polysaccharide Group C; mumps; Mumps Virus; mycobacteria; *Mycobacterium tuberculosis; Neisseria* spp; *Neisseria gonorrhoeae*; ovine blue tongue; ovine encephalitis; papilloma; SARS and associated coronaviruses; parainfluenza; paramyxovirus; paramyxoviruses; Pertussis; Plague, *Coxiella burnetti; Pneumococcus* spp.; *Pneumocystis carinii*; Pneumonia; Poliovirus; *Proteus* species, *Pseudomonas aeruginosa*; rabies; respiratory syncytial virus; rotavirus; Rubella, Salmonellae; schistosomiasis; Shigellae; simian immunodeficiency virus; Smallpox, *Staphylococcus aureus; Staphylococcus* spp.; *Streptococcus pyogenes; Streptococcus* spp.; swine influenza; tetanus, *Treponema pallidum*; Typhoid; Vaccinia; varicella-zoster virus; and *Vibrio cholera* and combinations thereof.

In some embodiments, the outer membrane protein is OmpW from *Acinetobacter baumannii*. In some embodiments the nucleotide and amino acid sequence of OmpW from *Acinetobacter baumannii* corresponds to SEQ ID NOS:9 and 10, respectively. In some embodiments, the outer membrane protein is OmpW from *Klebsiella pneumoniae*. In some embodiments the nucleotide and amino acid sequence of OmpW from *Klebsiella pneumoniae* corresponds to SEQ ID NOS: 13 and 14, respectively.

In some embodiments, the outer membrane protein is OmpA from *Acinetobacter baumannii*. In some embodiments the nucleotide and amino acid sequence of OmpA from *Acinetobacter baumannii* corresponds to SEQ ID NOS:7 and 8, respectively In some embodiments, the outer membrane protein is OmpA from *Klebsiella pneumoniae*. In some embodiments the nucleotide and amino acid sequence of OmpA from *Klebsiella pneumoniae* corresponds to SEQ ID NOS: 11 and 12, respectively.

In some embodiments, the *Salmonella* Typhi vector comprises both OmpW and OmpA from *Acinetobacter baumannii* or *Klebsiella pneumoniae*.

An antigenic or biologically active fragment is a polypeptide having an amino acid sequence that entirely is the same as part but not all of the amino acid sequence of one of the polypeptides. The antigenic fragment can be "free-standing," or comprised within a larger polypeptide of which they form a part or region, most preferably as a single continuous region.

In some embodiments, the antigenic or biologically active fragments include, for example, truncation polypeptides having the amino acid sequence of the polypeptides, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, and high antigenic index regions.

The fragment can be of any size. An antigenic fragment is capable of inducing an immune response in a subject or be recognized by a specific antibody. In some embodiments, the fragment corresponds to an amino-terminal truncation mutant. In some embodiments, the number of amino terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to carboxyl-terminal truncation mutant. In some embodiments, the number of carboxyl terminal amino acids missing from the fragment ranges from 1-100 amino acids. In some embodiments, it ranges from 1-75 amino acids, 1-50 amino acids, 1-40 amino acids, 1-30 amino acids, 1-25 amino acids, 1-20 amino acids, 1-15 amino acids, 1-10 amino acids and 1-5 amino acids.

In some embodiments, the fragment corresponds to an internal fragment that lacks both the amino and carboxyl terminal amino acids. In some embodiments, the fragment is 7-200 amino acid residues in length. In some embodiments, the fragment is 10-100 amino acid residues, 15-85 amino acid residues, 25-65 amino acid residues or 30-50 amino acid residues in length. In some embodiments, the fragment is 7 amino acids, 10 amino acids, 12 amino acids, 15 amino acids, 20 amino acids, 25 amino acids, 30 amino acids, 35 amino acids, 40 amino acids, 45 amino acids, 50 amino acids 55 amino acids, 60 amino acids, 80 amino acids or 100 amino acids in length.

In some embodiments, the fragment is at least 50 amino acids, 100 amino acids, 150 amino acids, 200 amino acids or at least 250 amino acids in length. Of course, larger antigenic fragments are also useful according to the present invention, as are fragments corresponding to most, if not all, of the amino acid sequence of the polypeptides described herein.

In some embodiments, the polypeptides have an amino acid sequence at least 80, 85%, 90%, 91%, 92%, 93%, 94%, 95%, 96%, 97%, 98%, 99%, or 100% identical to the polypeptides described herein or antigenic or biologically active fragments thereof. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which several, 5 to 10, 1 to 5, or 1 to 2 amino acids are substituted, deleted, or added in any combination.

In some embodiments, the polypeptides are encoded by polynucleotides that are optimized for high level expression in *Salmonella* using codons that are preferred in *Salmonella*. As used herein, a codon that is "optimized for high level expression in *Salmonella*" refers to a codon that is relatively more abundant in *Salmonella* in comparison with all other codons corresponding to the same amino acid. In some embodiments, at least 10% of the codons are optimized for high level expression in *Salmonella*. In some embodiments, at least 25%, at least 50%, at least 75%, at least 80%, at least 85%, at least 90%, at least 95%, or at least 99% of the codons are optimized for high level expression in *Salmonella*.

In some embodiments, OmpA comprises one or more mutations. In some embodiments, the mutation comprises one or more substitution mutations selected from D271A and R286A, with reference to *Acinetobacter baumannii* OmpA. In some embodiments, OmpA comprises both D271A and R286A mutations.

In some embodiments, the outer membrane protein is expressed on a plasmid in S. Typhi. In some embodiments, the plasmid has a non-antibiotic based plasmid selection system. In some embodiments, the plasmid expresses a gene that is essential for the growth of S. Typhi and has been chromosomally mutated in S. Typhi. In some embodiments, the gene encodes single stranded binding protein (SSB).

In some embodiments, outer membrane vesicles capable of mucosally presenting properly folded protective antigens to the immune system are generated through inducible over-expression of one or more vesicle-catalyzing proteins, such as ClyA and PagL. PagL and ClyA encompasses full length PagL and ClyA as well as biologically active fragments and variants of PagL and ClyA.

ClyA is an endogenous protein in S. Typhi, that can catalyze the formation of large outer membrane vesicles when over-expressed. Such a mechanism for vesicle formation raised the intriguing possibility of engineering ClyA to export from a live vector, via vesicles, heterologous foreign antigens; these vesicles could also carry immunomodulatory lipopolysaccharide (LPS) to perhaps improve the immunogenicity of an otherwise poorly immunogenic antigen. The utility of ClyA for enhancing the immunogenicity of the foreign Protective Antigen (PA83) from anthrax toxin, a strategy which produced a live vector anthrax vaccine proven to be immunogenic in both mouse and non-human primate animal models[53,67] has been confirmed. Like ClyA, over-expression of PagL has also been recently reported to induce prolific formation of outer membrane vesicles[6]; interestingly, although the pagL gene is present in the murine pathogen S. Typhimurium, it is absent in S. Typhi.

ClyA from S. Typhi was first described by Wallace et al., who also reported the crystal structure for the homologous HlyE hemolysin from *E. coli*. (Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.). ClyA protein can cause hemolysis in target cells. The present invention encompasses use of both hemolytically active and hemolytically inactive mutant forms of ClyA, with hemolytically inactive mutant forms being more preferred where preservation of antigen export and immunogenicity of the resulting proteins can be maintained. In some embodiments, the nucleotide and amino acid sequence of ClyA corresponds to SEQ ID NOS: 15 and 16, respectively. In some embodiments, the ClyA is mutated to reduce the hemolytic activity of ClyA while still retaining the export function of ClyA. In one embodiment, the ClyA mutant is ClyA I198N.

In another embodiment, the ClyA mutant is ClyA C285W. In some embodiments, the ClyA is mutated to reduce hemolytic activity of ClyA. In some embodiments, the ClyA mutant is selected from the group consisting of ClyA I198N, ClyA C285W, ClyA A199D, ClyA E204K. In some embodiments, the ClyA is a fusion protein. In some embodiments, the ClyA comprises I198N, A199D, and E204K substitution mutations. The mutant sequences are with reference to SEQ ID NO: 16.

The lipid A deacylase PagL which can be used in the invention is not particularly limiting. PagL encompasses full length PagL as well as biologically active fragments and variants of PagL. In some embodiments, PagL is from *Salmonella enterica*. In some embodiments, PagL is from the *Salmonella enterica* serovar Typhimurium. In some embodiments, the nucleotide sequence comprising PagL has been optimized. In some embodiments, one or more codons (e.g., rare codons) have been optimized to enhance expression. In some embodiments, the putative ribosome binding sites have been optimized to enhance expression. In some embodiments, the nucleotide sequence of PagL comprises SEQ ID NOS: 1, 3 or 5. In some embodiments, the amino acid sequence of PagL comprises SEQ ID NOS:2 or 4.

In some embodiments, the outer membrane protein is chromosomally integrated in S. Typhi. In some embodiments, the homologous S. Typhi outer membrane protein has been deleted or inactivated. It will be appreciated that inserting the gene cassettes into, e.g., the guaBA, htrA, ssb, and/or rpoS locus of S. Typhi can be accomplished, for example, using the lambda Red recombination system (Datsenko K A and Wanner B L. One-step inactivation of chromosomal genes in *Escherichia coli* K-12 using PCR products. PNAS. 2000. 97(12): 6640-5.). In some embodiments, the outer membrane protein is inserted into the guaBA locus of S. Typhi. In some embodiments, the outer membrane protein is inserted into the rpoS locus of S. Typhi. In some embodiments, the outer membrane protein OmpW is chromosomally integrated into the guaBA locus. In some embodiments, the outer membrane protein OmpA is chromosomally integrated into the rpoS locus.

In some embodiments, immunogenic cassettes can be integrated into either the ΔguaBA or ΔrpoS locus of CVD 910ssb, for example, to compare the immunogenicity of chromosomal integrations versus antigen-specific immunogenicity elicited by plasmid-based expression. In some embodiments, only the open reading frames of ΔguaBA and ΔrpoS are deleted, leaving the original promoters for these sites intact. In some embodiments, insertion cassettes include the $P_{ompC}$ promoter from the low copy expression plasmids, such that integration into ΔguaBA or ΔrpoS results in nested promoters controlling inducible expression of a given cassette at two levels.

In some embodiments, OmpA and/or OmpW outer membrane proteins from *A. baumannii* or *K. pneumoniae* are integrated into the chromosome of S. Typhi and expressed chromosomally. In some embodiments, OmpA and/or OmpW are integrated into the guaBA, htrA, ssb, and/or rpoS locus of S. Typhi. In some embodiments, chromosomal integration achieves high level expression and export of these proteins from the outer surface of an attenuated S. Typhi live vector, conferring protective efficacy against challenge, without over-attenuation of the vaccine.

In one embodiment, the invention provides an attenuated S. Typhi-bacterial live vector vaccine strain expressing the protective outer membrane protein OmpA from *A. baumannii* or *K. pneumoniae*. In one embodiment, the S. Typhi elicits protective efficacy against *A. baumannii* or *K. pneumoniae*. In some embodiments, S. Typhi-bacterial live vector comprises a synthetic gene cassette encoding OmpA integrated into the chromosome. In some embodiments, the protective antigen is expressed on the surface of the live vector vaccine. In some embodiments, the vaccine provides protective efficacy against intranasal and/or systemic challenge of the *A. baumannii* clinical isolate LAC-4, recently reported to be highly virulent in mice by either of these challenge routes. In some embodiments, the vaccine provides protective efficacy against intranasal and/or systemic challenge of carbapenem-resistant *K. pneumoniae*. In one embodiment, the S. Typhi-bacterial live vector vaccine strain is derived from S. Typhi Ty2. In some embodiments, the S. Typhi-bacterial live vector over-expresses either a ClyA protein, the lipid A deacylase PagL or both. In some embodiments, there is increased extracellular export of OmpA.

In another embodiment, the invention provides an attenuated S. Typhi-bacterial bivalent live vector vaccine strain expressing the outer membrane proteins OmpA and OmpW from *A. baumannii* or *K. pneumoniae*. In some embodiments, the S. Typhi-bacterial live vector over-expresses rOMVs enriched for both OmpA and OmpW. In some embodiments, the S. Typhi-bacterial bivalent live vector over-expresses either a ClyA protein responsible for naturally inducing OMV formation in S. Typhi, the lipid A deacylase PagL, or both.

Pharmaceutical Compositions

In some embodiments, the invention provides pharmaceutical compositions comprising S. Typhi live vector vaccines of the invention. Such compositions can be for use in vaccination of individuals, such as humans. Such pharmaceutical compositions may include pharmaceutically effective carriers, and optionally, may include other therapeutic ingredients, such as various adjuvants known in the art. Non-limiting examples of pharmaceutically acceptable carriers or excipients include, without limitation, any of the standard pharmaceutical carriers or excipients such as phosphate buffered saline solutions, water, emulsions such as oil/water emulsions, microemulsions, and the like.

In some embodiments, the composition comprises one or more live S. Typhi live vectors of the invention. In some embodiments, the composition comprises a combination of live *Salmonella* Typhi vectors, wherein a first *Salmonella* Typhi vector expresses i) OmpA, an antigenic fragment thereof or a variant thereof from *Acinetobacter baumannii*; and ii) OmpW, an antigenic fragment thereof or a variant thereof from *Acinetobacter baumannii*; and a second *Salmonella* Typhi vector expresses i) OmpA, an antigenic fragment thereof or a variant thereof from *Klebsiella pneumoniae*; and ii) OmpW, an antigenic fragment thereof or a variant thereof from *Klebsiella pneumoniae*.

In some embodiments, the invention provides a composition comprising isolated recombinant outer membrane vesicles from a live *Salmonella* Typhi vector of the invention, comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen.

In some embodiments, the invention provides a composition comprising a combination of isolated recombinant outer membrane vesicles from live *Salmonella* Typhi vectors of the disclosure. In some embodiments, the invention provides a composition comprising a combination of isolated recombinant outer membrane vesicles from live *Salmonella* Typhi vectors, wherein a first isolated recombinant outer membrane vesicle comprises i) OmpA, an antigenic fragment thereof or a variant thereof from *Acinetobacter baumannii*; and ii) OmpW, an antigenic fragment thereof or a variant thereof from *Acinetobacter baumannii* and a second isolated recombinant outer membrane vesicle comprises i) OmpA, an antigenic fragment thereof or a variant thereof from *Klebsiella pneumoniae*; and ii) OmpW, an antigenic fragment thereof or a variant thereof from *Klebsiella pneumoniae*, wherein the *Salmonella* Typhi has been engineered to express the heterologous antigens.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the S. Typhi live vector or isolated recombinant outer membrane vesicles which are desirable and efficacious for the vaccination application. The bacterial live vector materials or recombinant outer membrane vesicles are delivered in an amount capable of eliciting an immune reaction in which it is effective to increase the patient's immune response to the expressed outer membrane protein(s).

The bacterial live vector vaccines or isolated recombinant outer membrane vesicles of the present invention may be usefully administered to the host animal with any other suitable pharmacologically or physiologically active agents, e.g., antigenic and/or other biologically active substances.

The attenuated S. Typhi-bacterial live vector expressing one or more outer membrane proteins or isolated recombinant outer membrane vesicles described herein can be prepared and/or formulated without undue experimentation for administration to a mammal, including humans, as appropriate for the particular application. The pharmaceutical compositions may be manufactured without undue experimentation in a manner that is itself known, e.g., by means of conventional mixing, dissolving, dragee-making, levitating, emulsifying, encapsulating, entrapping, spray-drying, or lyophilizing processes, or any combination thereof.

In one embodiment, the attenuated S. Typhi-bacterial live vector expressing one or more outer membrane proteins or isolated recombinant outer membrane vesicles are administered mucosally. Suitable routes of administration may include, for example, oral, lingual, sublingual, rectal, transmucosal, nasal, buccal, intrabuccal, intravaginal, or intestinal administration; intravesicular; intraurethral; administration by inhalation; intranasal, or intraocular injections, and optionally in a depot or sustained release formulation. Furthermore, one may administer the compound in a targeted drug delivery system. Combinations of administrative routes are possible.

The dose rate and suitable dosage forms for the bacterial live vector vaccine compositions or recombinant isolated outer membrane vesicles of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

In some embodiments, the attenuated S. Typhi-bacterial live vector expressing one or more outer membrane proteins or recombinant isolated outer membrane vesicles can also be prepared for nasal administration. As used herein, nasal administration includes administering the compound to the mucous membranes of the nasal passage or nasal cavity of the subject. Pharmaceutical compositions for nasal administration of the S. Typhi-bacterial live vector or recombinant isolated outer membrane vesicles include therapeutically effective amounts of the S. Typhi-bacterial live vector or recombinant isolated outer membrane vesicles prepared by well-known methods to be administered, for example, as a nasal spray, nasal drop, suspension, gel, ointment, cream or powder. Administration of the S. Typhi-bacterial live vector or isolated recombinant outer membrane vesicles may also take place using a nasal tampon or nasal sponge.

The compositions may also suitably include one or more preservatives, anti-oxidants, or the like. Some examples of techniques for the formulation and administration of the S. Typhi-bacterial live vector or isolated recombinant outer membrane vesicles may be found in *Remington: The Science and Practice of Pharmacy*, Lippincott Williams & Wilkins Publishing Co., 21$^{st}$ addition, incorporated herein by reference.

In one embodiment, the pharmaceutical compositions contain the S Typhi-bacterial live vector or isolated recombinant outer membrane vesicles in an effective amount to achieve their intended purpose. In one embodiment, an effective amount means an amount sufficient to prevent or treat an infection. In one embodiment, to treat means to reduce the development of, inhibit the progression of, or ameliorate the symptoms of a disease in the subject being treated. In one embodiment, to prevent means to administer prophylactically, e.g., in the case wherein in the opinion of the attending physician the subject's background, heredity, environment, occupational history, or the like, give rise to an expectation or increased probability that that subject is at risk of having the disease, even though at the time of diagnosis or administration that subject either does not yet have the disease or is asymptomatic of the disease.

Therapeutic Methods

The present invention also includes methods of inducing an immune response in a subject. The immune response may be directed to one or more one or more outer membrane protein antigens expressed by the *Salmonella* Typhi live vector.

In some embodiments, the invention provides a method of inducing an immune response in a subject in need thereof, comprising administering to the subject an immunologically-effective amount of a live *Salmonella* Typhi vector that has been engineered to express one or more heterologous antigens from a pathogen, wherein the heterologous antigen comprises an outer membrane protein, an antigenic fragment thereof or a variant thereof, wherein the antigen is delivered to a mucosal tissue of the subject by an outer membrane vesicle produced by the *Salmonella* Typhi vector.

In some embodiments, the invention provides a method of inducing an immune response in a subject in need thereof, comprising administering to the subject an immunologically-effective amount of isolated recombinant outer membrane vesicles from *Salmonella* Typhi comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen, wherein the outer membrane vesicle is delivered to a mucosal tissue of the subject. In another aspect, the present invention is directed to methods of inducing an immune response against *A. baumannii* and/or *Klebsiella pneumoniae* in a subject in need thereof, comprising administering to the subject an immunologically-effective amount of a live *Salmonella* Typhi vector as described herein. In some embodiments, the live vector is administered mucosally. In some embodiments, the S. Typhi-bacterial live vector expresses rOMVs enriched for OmpA and/or OmpW.

In one embodiment, the method comprises administering a combination of live *Salmonella* Typhi vectors to a subject. In some embodiments, the combination comprises a first *Salmonella* Typhi vector that expresses i) OmpA, an antigenic fragment thereof or a variant thereof from *Acinetobacter baumannii*; and ii) OmpW, an antigenic fragment thereof or a variant thereof from *Acinetobacter baumannii*; and a second *Salmonella* Typhi vector that expresses i) OmpA, an antigenic fragment thereof or a variant thereof from *Klebsiella pneumoniae*; and ii) OmpW, an antigenic fragment thereof or a variant thereof from *Klebsiella pneumoniae*. In some embodiments, the combination of vectors is present in the same composition. In some embodiments, the vectors are present in separate compositions.

In one embodiment, the method comprises administering a combination of isolated recombinant outer membrane vesicles to a subject. In some embodiments, the combination of isolated recombinant outer membrane vesicles comprises a first outer membrane vesicles comprising i) OmpA, an antigenic fragment thereof or a variant thereof from *Acinetobacter baumannii*; and ii) OmpW, an antigenic fragment thereof or a variant thereof from *Acinetobacter baumannii*; and a second outer membrane vesicles comprising i) OmpA, an antigenic fragment thereof or a variant thereof from *Klebsiella pneumoniae*; and ii) OmpW, an antigenic fragment thereof or a variant thereof from *Klebsiella pneumoniae*.

Vaccine strategies are well known in the art and therefore the vaccination strategy encompassed by the invention does not limit the invention in any manner. In certain aspects of the invention, the S. Typhi live vector vaccine expressing one or more outer membrane protein antigens or isolated recombinant outer membrane vesicles is administered alone in a single application or administered in sequential applications, spaced out over time.

In other aspects of the invention, the S. Typhi live vector vaccine is administered as a component of a heterologous prime/boost regimen. "Heterologous prime/boost" strategies are 2-phase immunization regimes involving sequential administration (in a priming phase and a boosting phase) of the same antigen in two different vaccine formulations by the same or different route. In particular aspects of the invention drawn to heterologous prime/boost regimens, a mucosal prime/parenteral boost immunization strategy is used. For example, one or more S. Typhi live vector vaccines as taught herein is administered orally or other mucosal route and subsequently boosted parentally with a peptide vaccine comprising one or more of the outer membrane protein antigens.

In another aspect, the present invention is directed to methods of inducing an immune response against an outer membrane protein antigen from a pathogen in a subject in need thereof, comprising administering to the subject an immunologically-effective amount of a live *Salmonella* Typhi vector of the invention as a prime, and subsequently administering a boost composition comprising an outer membrane protein antigen, an antigenic fragment thereof or a variant thereof, and combinations thereof.

In some embodiments, the S. Typhi live vector vaccine is administered as a prime and is boosted with or isolated recombinant outer membrane vesicles of the invention. In some embodiments, the isolated recombinant outer membrane vesicles of the invention are administered as a prime and is boosted with the S. Typhi live vector vaccine of the invention. In some embodiments, the boost is administered mucosally, e.g., orally, or parenterally.

As used herein, an "immune response" is the physiological response of the subject's immune system to an immunizing composition. An immune response may include an innate immune response, an adaptive immune response, or both. In one embodiment of the present invention, the immune response is a protective immune response. A protective immune response confers immunological cellular memory upon the subject, with the effect that a secondary exposure to the same or a similar antigen is characterized by one or more of the following characteristics: shorter lag phase than the lag phase resulting from exposure to the selected antigen in the absence of prior exposure to the immunizing composition; production of antibody which continues for a longer period than production of antibody resulting from exposure to the selected antigen in the absence of prior exposure to the immunizing composition; a change in the type and quality of antibody produced in comparison to the type and quality of antibody produced upon exposure to the selected antigen in the absence of prior exposure to the immunizing composition; a shift in class response, with IgG antibodies appearing in higher concentrations and with greater persistence than IgM, than occurs in response to exposure to the selected antigen in the absence of prior exposure to the immunizing composition; an increased average affinity (binding constant) of the antibodies for the antigen in comparison with the average affinity of antibodies for the antigen resulting from exposure to the selected antigen in the absence of prior exposure to the immunizing composition; and/or other characteristics known in the art to characterize a secondary immune response.

In a further embodiment, the method of inducing an immune response comprises administering a pharmaceutical formulation as provided herein comprising one or more Salmonella Typhi live vectors or isolated recombinant outer membrane vesicles of the present invention to a subject in an amount sufficient to induce an immune response in the subject (an immunologically-effective amount). In some embodiments, the immune response is sufficient to confer protective immunity upon the subject against a later infection by the pathogen. In some embodiments, the compositions are administered intranasally.

In some embodiments, one or more S. Typhi live vector vaccines or isolated recombinant outer membrane vesicles of the invention are mucosally administered in a first priming administration, followed, optionally, by a second (or third, fourth, fifth, etc. . . . ) priming administration of the live vector vaccine or isolated recombinant outer membrane vesicles from about 2 to about 10 weeks later. In some embodiments, a boosting composition is administered from about 3 to about 12 weeks after the priming administration. In some embodiments, the boosting composition is administered from about 3 to about 6 weeks after the priming administration. In some embodiments, the boosting composition is substantially the same type of composition administered as the priming composition (e.g., a homologous prime/boost regimen).

In practicing immunization protocols for treatment and/or prevention, an immunologically-effective amount of a live Salmonella Typhi vector or isolated recombinant outer membrane vesicles is administered to a subject. As used herein, the term "immunologically-effective amount" means the total amount of a live S. Typhi vector or isolated recombinant outer membrane vesicles that is sufficient to show an enhanced immune response in the subject. When "immunologically-effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously.

The particular dosage depends upon the age, weight, sex and medical condition of the subject to be treated, as well as on the method of administration. Suitable doses can be readily determined by those of skill in the art.

The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject," "patient," and "host" are used interchangeably.

In some embodiments, the live Salmonella Typhi vectors or compositions comprising isolated recombinant outer membrane vesicles are administered to one or more subjects in long-term care facilities where vaccination would supplement rigorous antimicrobial stewardship to reduce the incidence of infections both prior to and upon transfer of patients to acute-care hospitals[53-55]. In some embodiments, subjects can be administered the vectors or compositions prior to discharge from hospitals after treatment for bacterial sepsis, pneumonia, or urinary tract infections, to prevent recurrence due to treatment failure or re-infection with more resistant pathogenic strains. In some embodiments, the subjects are military personnel at risk for skin and soft tissue infections with A. baumannii arising from severe trauma or burn injuries sustained on the battlefield[56].

The live Salmonella Typhi vectors or isolated recombinant outer membrane vesicles of the invention may be administered to warm-blooded mammals of any age. The live Salmonella Typhi vectors can be administered as a single dose or multiple priming doses, followed by one or more boosters. For example, a subject can receive a single dose, then be administered a booster dose up to 1 month, 2 months, 3 months, 4 months, 5 months, 6 months, 9 months, 1 year, 2 years, 3 years, 4 years, 5 years, 6 years, 7 years, 8 years, 9 years, or 10 or more years later.

Sample Embodiments

This section describes exemplary compositions and methods of the invention, presented without limitation, as a series of paragraphs, some or all of which may be alphanumerically designated for clarity and efficiency. Each of these paragraphs can be combined with one or more other paragraphs, and/or with disclosure from elsewhere in this application, including the materials incorporated by reference, in any suitable manner. Some of the paragraphs below expressly refer to and further limit other paragraphs, providing without limitation examples of some of the suitable combinations.

1. A method of inducing an immune response in a subject in need thereof, comprising administering to the subject an immunologically-effective amount of a live Salmonella enterica Typhi vector that has been engineered to express one or more heterologous antigens from a pathogen, wherein the heterologous antigen comprises an outer membrane protein, an antigenic fragment thereof or a variant thereof, wherein the antigen is delivered to a mucosal tissue of the subject by an outer membrane vesicle produced by the Salmonella Typhi vector.

2. The method of paragraph 1, wherein the pathogen is selected from Acinetobacter baumannii and Klebsiella pneumoniae.

3. The method of paragraph 2, wherein the outer membrane protein is OmpW.

4. The method of paragraph 2, wherein the outer membrane protein is OmpA.

5. The method of paragraph 2, wherein the Salmonella Typhi vector has been engineered to express both OmpW and OmpA from the pathogen.

6. The method of any of paragraphs 1-5, wherein the outer membrane protein is chromosomally integrated in S. Typhi.

7. The method of any of paragraphs 1-6, wherein the homologous S. Typhi outer membrane protein has been deleted or inactivated.

8. The method of any of paragraphs 1-7, wherein the outer membrane protein is inserted into an S. Typhi locus selected from the group consisting of guaBA, rpoS, htrA, ssb, and combinations thereof.

9. The method of any of paragraphs 1-8, wherein the outer membrane protein is inserted into the rpoS locus of S. Typhi.

10. The method of any of paragraphs 2-9, wherein the outer membrane protein OmpW is chromosomally integrated into the guaBA locus.

11. The method of any of paragraphs 2-10, wherein the outer membrane protein OmpA is chromosomally integrated into the rpoS locus.

12. The method of any of paragraphs 4-11, wherein the OmpA comprises one or more mutations.

13. The method of paragraph 22, wherein the mutation comprises one or more substitution mutations selected from D271A and R286A.

14. The method of paragraph 12, wherein OmpA comprises both D271A and R286A mutations.

15. The method of any of paragraphs 1-14, wherein the S. Typhi overexpresses a cytolysin A (ClyA) protein to facilitate outer membrane vesicle formation.

16. The method of paragraph 15, wherein the ClyA is mutated to reduce hemolytic activity of ClyA.

17. The method of paragraph 16, wherein the ClyA mutant is selected from the group consisting of ClyA I198N, ClyA A199D, ClyA E204K, ClyA C285W and combinations thereof.

18. The method of any of paragraphs 15-17, wherein the ClyA is a fusion protein.

20. The method of any of paragraphs 17, wherein the ClyA comprises I198N, A199D, and E204K substitution mutations.

21. The method of any of paragraphs 1-20, wherein the Salmonella Typhi vector overexpresses lipid A deacylase PagL.

22. The method of paragraph 21, wherein the PagL amino acid sequence is selected from SEQ ID NO:2 and SEQ ID NO:4.

23. The method of any of paragraphs 15-22, wherein the PagL and/or ClyA is expressed on a plasmid in S. Typhi.

24. The method of paragraph 23, wherein the plasmid has a non-antibiotic based plasmid selection system.

25. The method of paragraph 24, wherein the plasmid expresses a gene that is essential for the growth of S. Typhi and has been chromosomally mutated in S. Typhi.

26. The method of paragraph 25, wherein the gene encodes single stranded binding protein (SSB).

27. The method of any of paragraphs 1-26, wherein a combination of the live Salmonella Typhi vectors are administered to the subject, wherein a first Salmonella Typhi vector expresses i) OmpA, an antigenic fragment thereof or a variant thereof from Acinetobacter baumannii; and ii) OmpW, an antigenic fragment thereof or a variant thereof from Acinetobacter baumannii and a second Salmonella Typhi vector expresses i) OmpA, an antigenic fragment thereof or a variant thereof from Klebsiella pneumoniae; and ii) OmpW, an antigenic fragment thereof or a variant thereof from Klebsiella pneumoniae.

28. The method of any of paragraphs 1-27, wherein the subject is first administered the live Salmonella Typhi vector as a prime and subsequently administered an immunologically-effective amount of the live Salmonella Typhi vector as a boost.

29. The method of any of paragraphs 1-27, wherein the subject is first administered the live Salmonella Typhi vector as a prime and subsequently administered an immunologically-effective amount of isolated recombinant outer membrane vesicles produced from the Salmonella Typhi vector as a boost.

30. The method of any of paragraphs 1-29, wherein the Salmonella Typhi vector and/or isolated recombinant outer membrane vesicles are administered intranasally.

31. A method of inducing an immune response in a subject in need thereof, comprising administering to the subject an immunologically-effective amount of isolated recombinant outer membrane vesicles from Salmonella Typhi comprising one or more heterologous antigens from a pathogen, wherein the heterologous antigen comprises an outer membrane protein, an antigenic fragment thereof or a variant thereof, wherein the Salmonella Typhi has been engineered to express the heterologous antigen, wherein the outer membrane vesicle is delivered to a mucosal tissue of the subject.

32. The method of paragraph 31, wherein the pathogen is selected from Acinetobacter baumannii and Klebsiella pneumoniae.

33. The method of paragraph 32, wherein the outer membrane protein is OmpW.

34. The method of paragraph 32, wherein the outer membrane protein is OmpA.

35. The method of paragraph 32, wherein the Salmonella Typhi has been engineered to express both OmpW and OmpA from the pathogen.

36. The method of any of paragraphs 31-35, wherein the outer membrane protein is chromosomally integrated in S. Typhi.

37. The method of any of paragraphs 31-36, wherein the homologous S. Typhi outer membrane protein has been deleted or inactivated.

38. The method of any of paragraphs 31-37, wherein the outer membrane protein is inserted into an S. Typhi locus selected from the group consisting of guaBA, rpoS, htrA, ssb, and combinations thereof.

39. The method of any of paragraphs 31-38, wherein the outer membrane protein is inserted into the rpoS locus of S. Typhi.

40. The method of any of paragraphs 32-39, wherein the outer membrane protein OmpW is chromosomally integrated into the guaBA locus.

41. The method of any of paragraphs 32-40, wherein the outer membrane protein OmpA is chromosomally integrated into the rpoS locus.

42. The method of any of paragraphs 34-41, wherein the OmpA comprises one or more mutations.

43. The method of paragraph 42, wherein the mutation comprises one or more substitution mutations selected from D271A and R286A.

44. The method of paragraph 42, wherein OmpA comprises both D271A and R286A mutations.

45. The method of any of paragraphs 31-44, wherein the S. Typhi overexpresses a cytolysin A (ClyA) protein to facilitate outer membrane vesicle formation.

46. The method of paragraph 45, wherein the ClyA is mutated to reduce hemolytic activity of ClyA.

47. The method of paragraph 46, wherein the ClyA mutant is selected from the group consisting of ClyA I198N, ClyA A199D, ClyA E204K, ClyA C285W and combinations thereof.

48. The method of any of paragraphs 45-47, wherein the ClyA is a fusion protein.

49. The method of any of paragraphs 47, wherein the ClyA comprises I198N, A199D, and E204K substitution mutations.

50. The method of any of paragraphs 31-49, wherein the *Salmonella* Typhi vector overexpresses lipid A deacylase PagL.

51. The method of paragraph 50, wherein the PagL amino acid sequence is selected from SEQ ID NO:2 and SEQ ID NO:4.

52. The method of any of paragraphs 45-51, wherein the PagL and/or ClyA is expressed on a plasmid in S. Typhi.

53. The method of paragraph 52, wherein the plasmid has a non-antibiotic based plasmid selection system.

54. The method of paragraph 53, wherein the plasmid expresses a gene that is essential for the growth of S. Typhi and has been chromosomally mutated in S. Typhi.

55. The method of paragraph 54, wherein the gene encodes single stranded binding protein (SSB).

56. The method of any of paragraphs 31-55, wherein a combination of isolated recombinant outer membrane vesicles are administered to the subject, wherein a first outer membrane vesicles comprises i) OmpA, an antigenic fragment thereof or a variant thereof from *Acinetobacter baumannii*; and ii) OmpW, an antigenic fragment thereof or a variant thereof from *Acinetobacter baumannii* and a second outer membrane vesicles comprises i) OmpA, an antigenic fragment thereof or a variant thereof from *Klebsiella pneumoniae*; and ii) OmpW, an antigenic fragment thereof or a variant thereof from *Klebsiella pneumoniae*.

57. The method of any of paragraphs 31-56, wherein the subject is first administered the isolated recombinant outer membrane vesicles as a prime and subsequently administered an immunologically-effective amount of the outer membrane vesicles as a boost.

58. The method of any of paragraphs 31-56, wherein the subject is first administered the outer membrane vesicles as a prime and subsequently administered an immunologically-effective amount of the *Salmonella* Typhi vector as a boost.

59. The method of any of paragraphs 31-58, wherein the *Salmonella* Typhi vector and/or isolated recombinant outer membrane vesicles are administered intranasally.

60. A live *Salmonella* Typhi vector that has been engineered to express one or more heterologous antigens from a pathogen, wherein the heterologous antigen comprises an outer membrane protein, an antigenic fragment thereof or a variant thereof, wherein the *Salmonella* Typhi vector is capable of delivering the antigen to a mucosal tissue when administered to a subject.

61. The *Salmonella* Typhi vector of paragraph 60, wherein the pathogen is selected from *Acinetobacter baumannii* and *Klebsiella pneumoniae*.

62. The *Salmonella* Typhi vector of paragraph 60, wherein the outer membrane protein is OmpW.

63. The *Salmonella* Typhi vector of paragraph 60, wherein the outer membrane protein is OmpA.

64. The *Salmonella* Typhi vector of paragraph 60, wherein the *Salmonella* Typhi vector has been engineered to express both OmpW and OmpA from the pathogen.

65. The *Salmonella* Typhi vector of any of paragraphs 60-64, wherein the outer membrane protein is chromosomally integrated in S. Typhi.

66. The *Salmonella* Typhi vector of any of paragraphs 60-65, wherein the homologous S. Typhi outer membrane protein has been deleted or inactivated.

67. The *Salmonella* Typhi vector of any of paragraphs 60-66, wherein the outer membrane protein is inserted into an S. Typhi locus selected from the group consisting of guaBA, rpoS, htrA, ssb, and combinations thereof.

68. The *Salmonella* Typhi vector of any of paragraphs 60-67, wherein the outer membrane protein is inserted into the rpoS locus of S. Typhi.

69. The *Salmonella* Typhi vector of any of paragraphs 60-68, wherein the outer membrane protein OmpW is chromosomally integrated into the guaBA locus.

70. The *Salmonella* Typhi vector of any of paragraphs 60-69, wherein the outer membrane protein OmpA is chromosomally integrated into the rpoS locus.

71. The *Salmonella* Typhi vector of any of paragraphs 63-70, wherein the OmpA comprises one or more mutations.

72. The *Salmonella* Typhi vector of paragraph 71, wherein the mutation comprises one or more substitution mutations selected from D271A and R286A.

73. The *Salmonella* Typhi vector of paragraph 71, wherein OmpA comprises both D271A and R286A mutations.

74. The *Salmonella* Typhi vector of any of paragraphs 60-73, wherein the S. Typhi overexpresses a cytolysin A (ClyA) protein to facilitate outer membrane vesicle formation.

75. The *Salmonella* Typhi vector of paragraph 74, wherein the ClyA is mutated to reduce hemolytic activity of ClyA.

76. The *Salmonella* Typhi vector of paragraph 75, wherein the ClyA mutant is selected from the group consisting of ClyA I198N, ClyA A199D, ClyA E204K, ClyA C285W and combinations thereof.

77. The *Salmonella* Typhi vector of any of paragraphs 74-76, wherein the ClyA is a fusion protein.

78. The *Salmonella* Typhi vector of paragraph 77, wherein the ClyA comprises I198N, A199D, and E204K substitution mutations.

79. The *Salmonella* Typhi vector of any of paragraphs 60-78, wherein the *Salmonella* Typhi vector overexpresses lipid A deacylase PagL.

80. The *Salmonella* Typhi vector of paragraph 79, wherein the PagL amino acid sequence is selected from SEQ ID NO:2 and SEQ ID NO:4.

81. The *Salmonella* Typhi vector of any of paragraphs 74-80, wherein the PagL and/or ClyA is expressed on a plasmid in S. Typhi.

82. The *Salmonella* Typhi vector of paragraph 81, wherein the plasmid has a non-antibiotic based plasmid selection system.

83. The *Salmonella* Typhi vector of paragraph 82, wherein the plasmid expresses a gene that is essential for the growth of S. Typhi and has been chromosomally mutated in S. Typhi.

84. The *Salmonella* Typhi vector of paragraph 83, wherein the gene encodes single stranded binding protein (SSB).

85. A composition comprising a combination of the live *Salmonella* Typhi vectors according to paragraphs 60-84, wherein a first *Salmonella* Typhi vector expresses i) OmpA, an antigenic fragment thereof or a variant thereof from *Acinetobacter baumannii*; and ii) OmpW, an antigenic fragment thereof or a variant thereof from *Acinetobacter baumannii* and a second *Salmonella* Typhi vector expresses i) OmpA, an antigenic fragment thereof or a variant thereof from *Klebsiella pneumoniae*; and ii) OmpW, an antigenic fragment thereof or a variant thereof from *Klebsiella pneumoniae*.

86. A composition comprising isolated recombinant outer membrane vesicles from *Salmonella* Typhi comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen.

87. The composition of paragraph 86, wherein the pathogen is selected from *Acinetobacter baumannii* and *Klebsiella pneumoniae*.

88. The composition of paragraph 87, wherein the outer membrane protein is OmpW.

89. The composition of paragraph 87, wherein the outer membrane protein is OmpA.

90. The composition of paragraph 87, wherein the *Salmonella* Typhi has been engineered to express both OmpW and OmpA from the pathogen.

91. The composition of any of paragraphs 86-90, wherein the outer membrane protein is chromosomally integrated in S. Typhi.

92. The composition of any of paragraphs 86-91, wherein the homologous S. Typhi outer membrane protein has been deleted or inactivated.

93. The composition of any of paragraphs 86-92, wherein the outer membrane protein is inserted into an S. Typhi locus selected from the group consisting of guaBA, rpoS, htrA, ssb, and combinations thereof.

94. The composition of any of paragraphs 86-93, wherein the outer membrane protein is inserted into the rpoS locus of S. Typhi.

95. The composition of any of paragraphs 86-94, wherein the outer membrane protein OmpW is chromosomally integrated into the guaBA locus.

96. The composition of any of paragraphs 86-95, wherein the outer membrane protein OmpA is chromosomally integrated into the rpoS locus.

97. The composition of any of paragraphs 89-96, wherein the OmpA comprises one or more mutations.

98. The composition of paragraph 97, wherein the mutation comprises one or more substitution mutations selected from D271A and R286A.

99. The composition of paragraph 97, wherein OmpA comprises both D271A and R286A mutations.

100. The composition of any of paragraphs 86-99, wherein the S. Typhi overexpresses a cytolysin A (ClyA) protein to facilitate outer membrane vesicle formation.

101. The composition of paragraph 100, wherein the ClyA is mutated to reduce hemolytic activity of ClyA.

102. The composition of paragraph 101, wherein the ClyA mutant is selected from the group consisting of ClyA I198N, ClyA A199D, ClyA E204K, ClyA C285W and combinations thereof.

103. The composition of any of paragraphs 100-102, wherein the ClyA is a fusion protein.

104. The composition of any of paragraphs 102, wherein the ClyA comprises I198N, A199D, and E204K substitution mutations.

105. The composition of any of paragraphs 86-104, wherein the *Salmonella* Typhi overexpresses lipid A deacylase PagL.

106. The composition of paragraph 105, wherein the PagL amino acid sequence is selected from SEQ ID NO:2 and SEQ ID NO:4.

107. The composition of any of paragraphs 100-106, wherein the PagL and/or ClyA is expressed on a plasmid in S. Typhi.

108. The composition of paragraph 107, wherein the plasmid has a non-antibiotic based plasmid selection system.

109. The composition of paragraph 108, wherein the plasmid expresses a gene that is essential for the growth of S. Typhi and has been chromosomally mutated in S. Typhi.

110. The composition of paragraph 109, wherein the gene encodes single stranded binding protein (SSB).

111. A composition comprising a combination of the isolated recombinant outer membrane vesicles of paragraphs 86-110, wherein a first isolated recombinant outer membrane vesicle comprises i) OmpA, an antigenic fragment thereof or a variant thereof from *Acinetobacter baumannii*; and ii) OmpW, an antigenic fragment thereof or a variant thereof from *Acinetobacter baumannii* and a second isolated recombinant outer membrane vesicle comprises i) OmpA, an antigenic fragment thereof or a variant thereof from *Klebsiella pneumoniae*; and ii) OmpW, an antigenic fragment thereof or a variant thereof from *Klebsiella pneumoniae*.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. Generation of *Salmonella enterica* Serovar Typhi Live Vaccines Against *Acinetobacter baumannii* and *Klebsiella pneumoniae*

While rapid identification of pathogens, novel therapeutic interventions, and passive immunization have critical roles in disease control, none can substitute for pre-existing protective immunity. Mucosally delivered bacterial live carrier vaccines represent a practical and versatile strategy for immunization. In this approach, genes that encode protective antigens of unrelated pathogens are expressed in an attenuated vaccine strain and delivered mucosally to generate relevant local and systemic immune responses. Using appropriate genetic engineering of a *Salmonella enterica* serovar Typhi live vaccine platform, we will construct a safe, effective, and practical multivalent carrier vaccine against pneumonic and systemic infections caused by multidrug-resistant (MDR) strains of *Acinetobacter baumannii* and carbapenem-resistant *Klebsiella pneumoniae*. No licensed vaccine is currently available against either of these pathogens.

A novel multivalent vaccine against these MDR pathogens will be developed that elicits humoral, cellular, and mucosal immunity against the highly conserved outer membrane proteins OmpA and OmpW from each pathogen. Synthetic gene cassettes encoding these foreign antigens will be stably integrated into the chromosome of a live attenuated S. Typhi vaccine candidate, enabling high level expression of OmpA and OmpW on the outer surface of the carrier vaccine. To enhance antigen-specific immunity, we will export these vaccine antigens off the surface of the live vaccine in vivo using a novel inducible outer membrane vesicle delivery system to improve delivery of sufficient antigen to immune inductive sites to confer protection against challenge. Induction of OMV formation and antigen delivery will be accomplished by over-expression of PagL, a lipid A deacylase recently reported to catalyze hypervesiculation when over-expressed in *Salmonella*[1]. Given that deacylation detoxifies lipid A by reducing TLR4-mediated activation of inflammatory responses[2,3], we propose to purify these recombinant OMVs (rOMVs) from our carrier strains and test the protective efficacy of these component vaccines as well.

Part 1. Bivalent S. Typhi-based carrier vaccines expressing the protective outer membrane proteins OmpA and OmpW from either *A. baumannii* or *K. pneumoniae* will be created and will efficiently export both foreign antigens via PagL-mediated OMVs. We will verify high levels of OmpA and OmpW expression by western immunoblot analysis, surface expression by flow cytometry, and efficient extracellular export in purified OMVs with reduced reactogenicity.

Part 2. Bivalent S. Typhi-based carrier vaccines will be created and will efficiently express OmpA and OmpW from either *A. baumannii* or *K. pneumoniae* and will elicit protection against challenge in mice. Mice will be immunized intranasally using either a homologous prime-boost strategy (Part 2A) or a heterologous prime-boost strategy (Part 2B). Homologous immunization will use either carrier vaccine alone or rOMVs purified from carrier strains; heterologous immunization will involve priming with carrier vaccine and boosting with rOMVs. Humoral and cellular immunity will be measured, with specific emphasis on antigen-specific Th17 responses. Mice immunized against *A. baumannii* will be challenged either by the systemic or pulmonary route with the virulent clinical isolate LAC-4[4,5]. Mice immunized against *K. pneumoniae* will be lethally challenged by either the systemic or pulmonary route with the virulent O1:K2 strain B5055[6].

Part 3: Carrier vaccines and purified OMVs, developed and tested in parts 1 and 2 against challenge with a single pathogen, will confer protection against challenge with both *A. baumannii* and *K. pneumoniae* in mice mucosally primed with doses containing a mix of the 2 carrier vaccines and boosted with mixed OMV preparations. We will test both carrier vaccine-prime/OMV boost and OMV-prime/carrier vaccine boost immunization strategies against sequential challenge with both pathogens. We will also test protection against polymicrobial infection by simultaneously challenging with lethal doses of both *A. baumannii* and *K. pneumoniae*.

In some aspects, the invention remodels the outer membrane of an attenuated S. Typhi-based live carrier vaccine into an antigen presentation platform in which protective outer membrane antigens are mucosally delivered to immune inductive sites to elicit protection. Four independent vaccines can be generated (two live carrier vaccines and two purified rOMV-based acellular vaccines against either *A. baumannii* or *K. pneumoniae*) with the flexibility to mix carrier vaccines and rOMVs into single dose formulations to potentially improve protective efficacy.

Outer Membrane Remodeling as a Vaccine Strategy. In this example, we will utilize attenuated strains of S. Typhi as live vectors for expression and delivery of protective outer membrane proteins to the immune system via mucosal immunization. Historically, attenuated S. Typhi live vectors have been engineered for expression of foreign antigens either within the cytoplasm of the live vector (less immunogenic) or exported onto the surface of the live vector (more immunogenic), and have typically involved a single foreign antigen expressed from a plasmid. In this example, we propose a novel strategy, which will mimic previous success achieved with *A. baumannii* and *K. pneumoniae* outer membrane vesicles, in which the outer membrane of our live vector vaccine strain will be "remodeled" such that the outer membrane itself functions as the antigen delivery platform and biological source of highly immunogenic recombinant outer membrane vesicles (rOMVs), genetically engineered to be specifically enriched in OmpA and OmpW protective antigens. We will enhance the formation and delivery of these rOMVs in two novel ways: 1] we will enhance the formation of rOMVs by reducing the anchoring properties of OmpA to the rigid peptidoglycan of our live vector vaccine, an observation first reported by Park et al[87] to reduce the non-covalent association of OmpA with peptidoglycan; in addition, we will further enhance this effect by deleting the endogenous S. Typhi $ompA^{St}$ gene to again reduce interaction of endogenous StOmpA with the peptidoglycan layer; 2] we will enhance the delivery of rOMVs through inducible over-expression of a novel protein PagL which catalyzes OMV formation.

Inducible Vesicle Delivery System. We have developed a novel antigen delivery system through inducible over-expression of the vesicle-catalyzing protein PagL, which increases formation of outer membrane vesicles capable of mucosally presenting properly folded outer membrane protective antigens to the immune system. Over-expression of PagL has been shown to induce prolific formation of outer membrane vesicles in *Salmonella*[1]. Interestingly, PagL is a 3-O-deacylase[88] which converts proinflammatory hexa-acylated lipid A into penta-acylated forms, thereby reducing TLR-4 signaling of inflammatory responses 100-fold[2,3]. Therefore, rOMVs exported from *Salmonella* strains through over-expression of PagL would be expected to be less reactogenic, which would improve the clinical acceptability of these vesicles if purified and used as primary or booster vaccines. Although the pagL gene is naturally found in the murine pathogen S. Typhimurium, it is absent from the genome of S. Typhi. In this example, the protective efficacy of a live vector vaccine against *A. baumannii* and *K. pneumoniae* can be significantly improved through PagL-mediated hypervesiculation to enhance mucosal delivery of protective OmpA and OmpW proteins via recombinant OMVs. Mice will be intranasally immunized only with live carrier vaccines or purified rOMVs (i.e. homologous prime-boosting). In another aspect mice will be intranasally primed with carrier vaccine and intranasally boosted with purified rOMVs.

Results

AbOmpA Expression in Attenuated S. Typhi Live Vector Vaccines is not Pathogenic. We have engineered a novel attenuated strain of S. Typhi, CVD 910, specifically intended for use as a carrier vaccine presenting foreign antigens capable of eliciting protective immunity against unrelated human pathogens such as *A. baumannii* and *K. pneumoniae*. This strain replaces our previously constructed attenuated vaccine candidate, CVD 908-htrA, derived from the wild-type pathogen Ty2 and carrying attenuating deletion mutations in aroC, aroD, and htrA, which proved to be safe and highly immunogenic in Phase 2 clinical trials[60]. CVD 910 was engineered to carry deletions in guaBA and htrA, while maintaining the same level of attenuation as the clinically proven CVD 908-htrA strain. We conducted a preliminary assessment of the attenuation of CVD 910 using a hog gastric mucin intraperitoneal murine challenge model to compare the minimum lethal dose causing death in 50% of a group of BALB/c mice (LD50) for CVD 910 versus CVD 908-htrA. For this model, we broadly follow the guidelines recommended in the Code of Federal Regulations for Food and Drugs, Title 21, Part 620.13 (c-d), 1986 for intraperitoneal challenge of mice with S. Typhi. Using this method, we confirmed the LD50 for both CVD 910 and CVD 908-htrA to be approximately $5 \times 10^5$ CFU[65], versus an LD50 of ~10 CFU for wildtype Ty2[89] in this challenge model.

Having established a baseline level of safety for CVD 910, comparable to that of the clinically acceptable vaccine candidate CVD 908-htrA, we then demonstrated the utility of this vaccine strain for use as a carrier by developing and testing a vaccine against pneumonic plague caused by *Y. pestis*. We constructed a bivalent live plague carrier vaccine encoding a protective F1 capsular protein antigen successfully exported to the surface of the live vector vaccine, as well as a cytoplasmically expressed protective LcrV protein required for secretion of *Y. pestis* virulence effector proteins; the genetic cassette encoding F1 was integrated into the deleted guaBA chromosomal locus of CVD 910, and a separate genetic cassette encoding LcrV was integrated into the deleted htrA of CVD 910. In mice immunized intranasally with this bivalent carrier vaccine, we achieved 100% protection against a lethal pulmonary challenge with fully virulent *Y. pestis*[66] demonstrating the utility of CVD 910 as a carrier vaccine platform as well as the feasibility of chromosomal integration as a key strategy for engineering protective multivalent vaccines.

We then designed a synthetic $ompA^{Ab}$ synthetic expression cassette encoding the 38.6 kDa AbOmpA candidate vaccine antigen, expressed on a non-antibiotic genetically stabilized low-copy-number expression plasmid pSEC10; this unique plasmid is maintained by expression of the critical single-stranded binding protein SSB which has been deleted from the chromosome of CVD 910[64]. Given reports in the literature that AbOmpA functions as a virulence factor in vitro when studied using tissue culture cells[90,91] it was critical for us to formally exclude the possibility of AbOmpA unacceptably increasing the virulence of the CVD 910 strain carrying this plasmid [designated here as CVD 910(pSEC10Ab)]. We therefore evaluated the effect of plasmid-based expression of AbOmpA on virulence by repeating the hog gastric mucin challenge studies for CVD 910 (pSEC10Ab) versus the parent vaccine CVD 910. We determined the LD50 of CVD 910 to be $2.14 \times 10^6$ CFU versus $8.73 \times 10^6$ CFU for CVD 910(pSEC10Ab). We conclude that expression of AbOmpA has no effect on the safety of CVD 910, and that CVD 910 expressing AbOmpA constitutes a clinically acceptable candidate for further development of a live carrier vaccine against *A. baumannii* infections.

Figure 2:
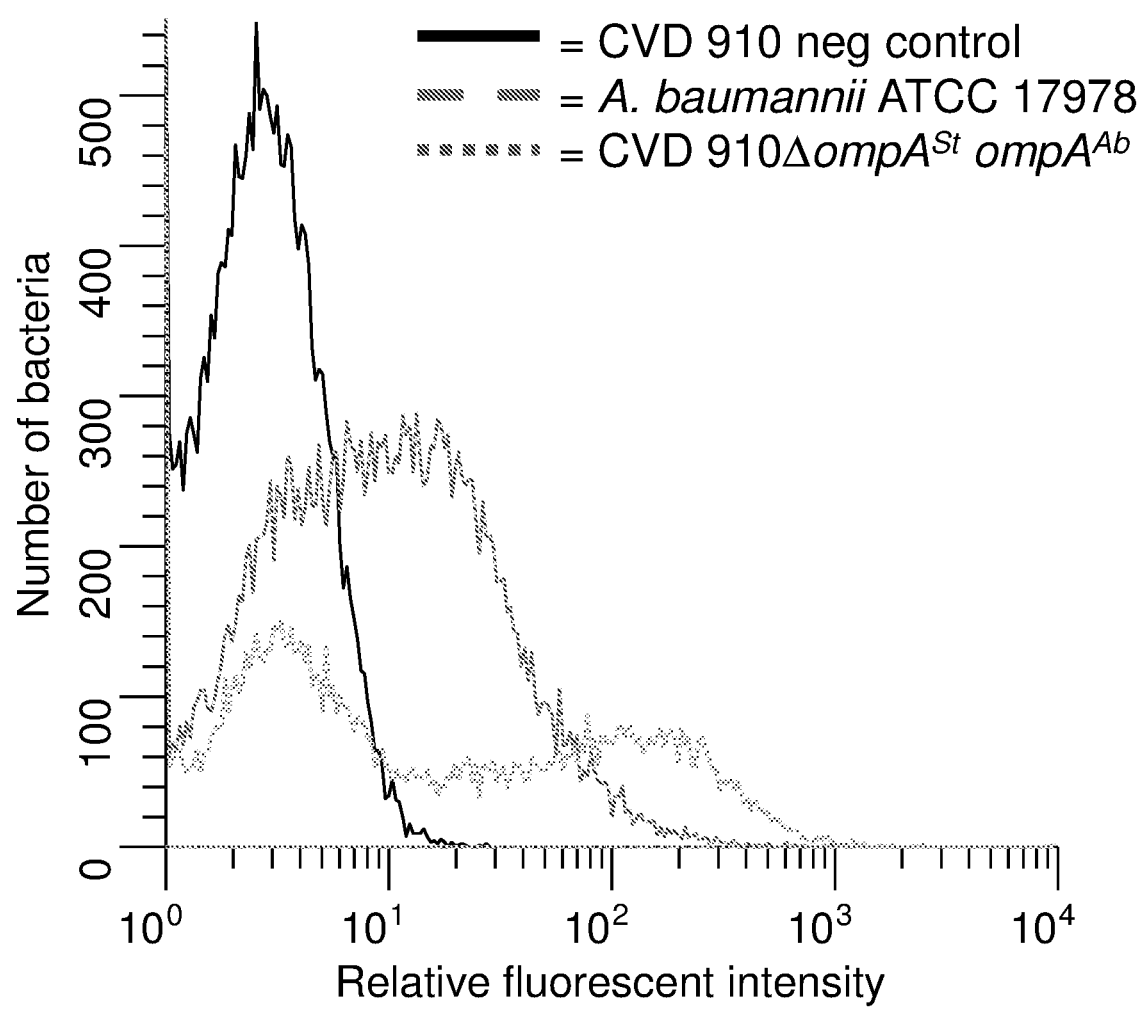
FIG. 2. Flow cytometry histograms of *A. baumannii* ATCC versus monovalent 910DOmpA$^{St}$OmpA$^{Ab}$ exponentially growing cells, Cells were stained with primary mouse AbOmpA-specific polyclonal mouse antiserum (diluted 1:25) and secondary anti-mouse Alexa fluor488 (1:25) antibody. 50,000 events were collected and background fluorescence was determined using CVD910 ΔOmpA ΔguaAB::OmpA$^{ab}$ stained only with anti-mouse Alexa fluor488.

Surface Expression of AbOmpA in CVD 910. Having ruled out any safety concerns with the expression of AbOmpA in CVD 910, we then used the chromosomal integration techniques, previously proven in the development of a highly immunogenic and protective live mucosal vaccine against pneumonic plague[66], to construct several monovalent live carrier strains in which the $ompA^{Ab}$ synthetic expression cassette was integrated into the chromosome of CVD 910. These strains were designed to address 3 critical questions that would provide a solid scientific foundation upon which the current examples could be based: 1] can AbOmpA be recognized on the surface of the live vector by AbOmpA-specific antibodies, 2] can a foreign OmpA protein such as AbOmpA be expressed in the outer membrane of CVD 910 without being affected by expression of the endogenous StOmpA from S. Typhi (encoded by $ompA^{St}$), and 3] can surfaced-expressed AbOmpA be efficiently exported from CVD910 via outer membrane vesicles? We first constructed a monovalent live vector strain in which the $ompA^{Ab}$ synthetic expression cassette was integrated into the ΔguaBA site of CVD 910, creating CVD 910ompA$^{Ab}$. To determine any influence of StOmpA on AbOmpA expression, we constructed an additional live vector in which $ompA^{St}$ was deleted to create CVD 910ΔompA$^{St}$ompA$^{Ab}$. We then confirmed expression of AbOmpA in both CVD 910ompA$^{Ab}$ and CVD 910ΔompA$^{St}$ompA$^{Ab}$ by western immunoblot analysis (data not shown). To demonstrate surface expression of AbOmpA, we used flow cytometry to determine surface accessibility of AbOmpA epitopes by comparing surface labeling of CVD 910ΔompA$^{St}$ompA$^{Ab}$ to surface labelling of wild type *A. baumannii* ATCC 17978; both strains were stained with primary polyclonal mouse AbOmpA-specific antiserum, followed by secondary staining with anti-mouse Alexa fluor488. As shown in FIG. 2, the monovalent carrier produced two fluorescence peaks, one of which (57% of the cells) was equivalent to the unstained CVD 910 negative control and the other peak (43% of the cells) with an impressive mean fluorescence of 159.4; the fluorescence of ATCC 17978 presented as a single peak with a mean fluorescence of 23.4. We interpreted the biphasic fluorescence of CVD 910ΔompA$^{St}$ompA$^{Ab}$ as indicative of incomplete export of over-expressed AbOmpA to the surface of the carrier strain.

TABLE 1

Monovalent *S. Typhi*-based carrier vaccines expressing AbOmpA from *A. baumannii*.

| STRAIN | AbOmpA allele | Chromosomal integration site | StOmpA |
|---|---|---|---|
| CVD 910 negative control | — | — | + |
| CVD 910(pSEC10) | — | — | + |
| CVD 910ΔompA$^{St}$(pSEC10) | wild type | guaBA | – |
| CVD 910ΔompA$^{St}$ompA$^{Ab}$(pSEC10) | wild type | guaBA | – |
| CVD 910ΔompA$^{St}$ompA$^{Ab*}$(pSEC10) exponential | D271A and R286A | rpoS | – |
| CVD 910ΔompA$^{St}$ompA$^{Ab*}$(pSEC10) stationary | D271A and R286A | rpoS | – |

Figure 3:
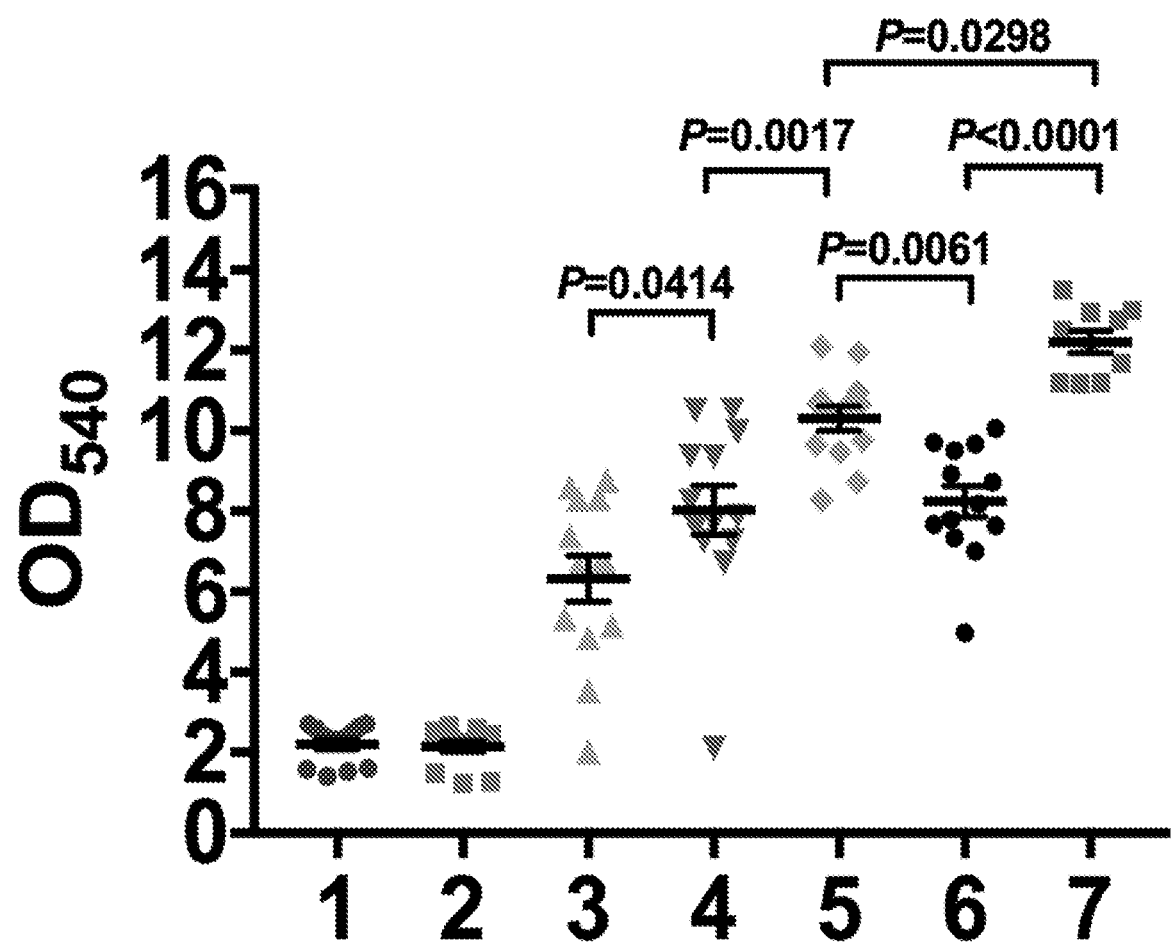
FIG. 3. Hemolytic activity of isogenic attenuated S Typhi CVD 910 live vector strains expressing AbOmpA. Samples from approximately $2 \times 10^7$ CFU of synchronized bacterial cultures were analyzed for hemolytic activity using sheep red blood cells. Data are pooled from 3 independent assays with five measurements per group. Lane 1: PBS; Lane 2: 910; Lane 3: 910(pSEC10); Lane 4: 910DOmpA$^{St}$ (pSEC10); Lane 5: 910ΔOmpA$^{St}$ΔguaBA::OmpA$^{Ab}$ (pSEC10); Lane 6: 910ΔOmpA$^{St}$ΔrpoS::OmpA$^{Ab}$* (pSEC10) expo; Lane 7: 910ΔOmpA$^{St}$ΔrpoS::OmpA$^{Ab}$* (pSEC10) stat.
Figure 4:
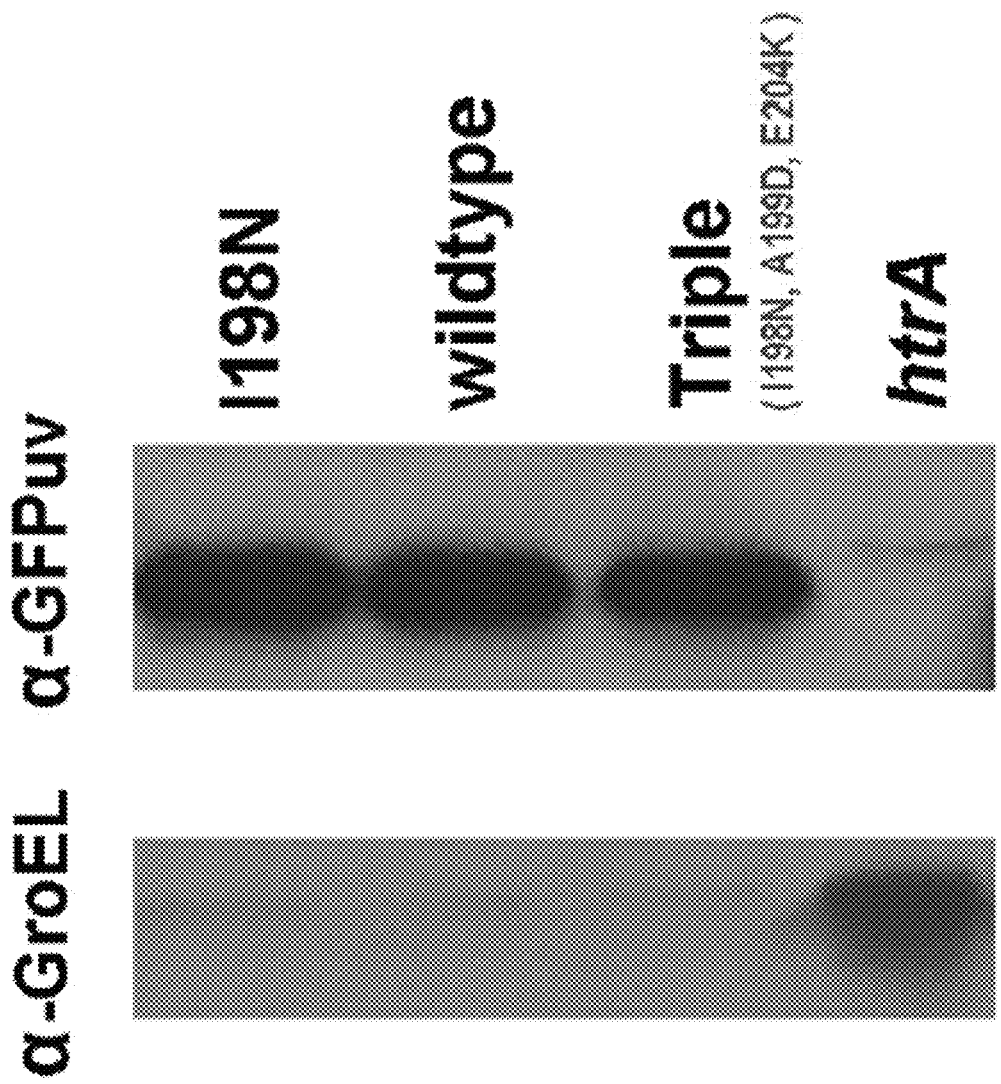
FIG. 4. Western immunoblot of culture supernatants from DH5a expressing non-hemolytic fusions of ClyA fused to the fluorescent reporter protein GFPuv (ClyA*-GFPuv) or wildtype ClyA-GFPuv protein. (A.) Culture supernatants stained with anti-GFP polyclonal antibody to detect exported ClyA*-GFPuv fusions. (B.) Culture supernatants stained with polyclonal antibody against the cytoplasmic protein GroEL; a lysate of CVD 908-htrA(pClyA-GFPuv) was included as a control for background autolysis of live vectors.

Proof-of-Principle Studies with an OMV-Mediated Antigen Delivery Platform. We then investigated any influence of endogenous StOmpA expression on the extracellular export of surface-expressed AbOmpA via outer membrane vesicles. Export of AbOmpA via rOMVs was facilitated by over-expression of a novel endogenous protein in S. Typhi called cytolysin A (ClyA), first reported by Wai et al. to catalyze the formation of large outer membrane vesicles when over-expressed[92]; we have successfully exploited over-expression of ClyA for export of foreign antigens out of engineered carrier strains[62]. Since ClyA exhibits hemolytic activity, we can indirectly monitor export of surface-expressed foreign antigens such as AbOmpA via ClyA-mediated vesiculation by measuring the hemolytic activity in the supernatants of carrier strains; as hemolytic activity in supernatants increases, we can infer that ClyA-mediated export of AbOmpA via OMVs increases as well. However, ClyA-mediated vesicle formation for export of AbOmpA could theoretically be hindered by the presence of endogenous StOmpA naturally synthesized in CVD 910. In support of this hypothesis, Park et al. have reported that the carboxyl-terminus of OmpA proteins tightly associates with the peptidoglycan layer of Gram-negative bacteria[87]. However, Park et al have also noted that the alanine substitutions D271A and R286A block the strong association of the mutant OmpA$^{D271A-R286A}$ protein to rigid peptidoglycan[87]. Therefore, we hypothesized that ClyA-mediated export of AbOmpA could be improved by incorporating these same D271A and R286A substitutions into our synthetic ompA$^{Ab}$ gene to "loosen up" the outer membrane by expressing this modified ompA$^{Ab}$* allele in CVD 910ΔompA$^{St}$ in which StOmpA had been previously deleted. To test this hypothesis, we therefore constructed a panel of isogenic carrier strains, over-expressing ClyA from our low-copy-number expression plasmid pSEC10, as presented in Table 1. After multiple attempts at integrating the ompA$^{Ab}$* allele into the guaBA locus proved unsuccessful, we chose instead to integrate into the rpoS locus, a site we have previously exploited for successful expression of other foreign antigens[66]; therefore, expression of ompA$^{Ab}$ alleles integrated into the guaBA locus will be optimally expressed during the exponential phase of growth, while optimum expression from the rpoS locus will occur in stationary phase. All strains were grown at 37° C. into mid-log phase growth unless otherwise noted, and ClyA-mediated export of OMVs (along with surface-expressed AbOmpA) was then quantitatively evaluated by measuring the hemolytic activity at OD$_{540}$ of approximately 2×10$^7$ CFU of bacteria against sheep red blood cells[93]. As shown in FIG. 3, no hemolytic activity was present in the vaccine strain CVD 910 (lane 2), but increased as expected with the introduction of the expression plasmid pSEC10 encoding ClyA (lane 3). Interestingly, hemolytic activity increased yet again upon deletion of the endogenous ompA$^{St}$ (p=0.0414; lane 4 versus lane 3), supporting the hypothesis that OmpA coordinates with peptidoglycan and reduces ClyA-mediated OMV formation. Surprisingly, trans-complementation of ompA$^{St}$ with ompA$^{Ab}$ integrated into the guaBA locus further increased hemolytic activity (p=0.0017; lane 5 versus lane 4), suggesting that AbOmpA may not be associating as tightly with the peptidoglycan as wild type StOmpA. However, hemolytic activity was the highest in the live vector in which the mutant ompA$^{Ab}$* was expressed in a live vector in which ompA$^{St}$ was deleted (p=0.0298; lane 7 versus lane 5), strongly supporting the hypothesis that ClyA-mediated export of OMVs (along with foreign outer membrane protein antigens such as AbOmpA) can be efficiently carried out when significant interactions between OmpA proteins (whether homologous or heterologous) and peptidoglycan are reduced or removed. We therefore expect that rOMVs exported from S. Typhi-based carrier vaccines will be able to present properly folded and surface accessible OmpA and OmpW to the immune system, and that over-expression of rOMVs will enhance delivery and improve protective efficacy.

Development of a PagL-Mediated Antigen Delivery Platform. Because ClyA is a hemolysin with cytopathic characteristics[94,95] that may reduce the clinical acceptability of candidate vaccine strains in which ClyA is over-expressed, we sought to develop a non-pathogenic alternative for inducing formation and export of OMVs based on PagL.

We therefore constructed a synthetic pagL gene and inserted it into our non-antibiotic low-copy-number expression plasmid pSEC10, replacing the clyA gene to create pPagL.

Figure 14:
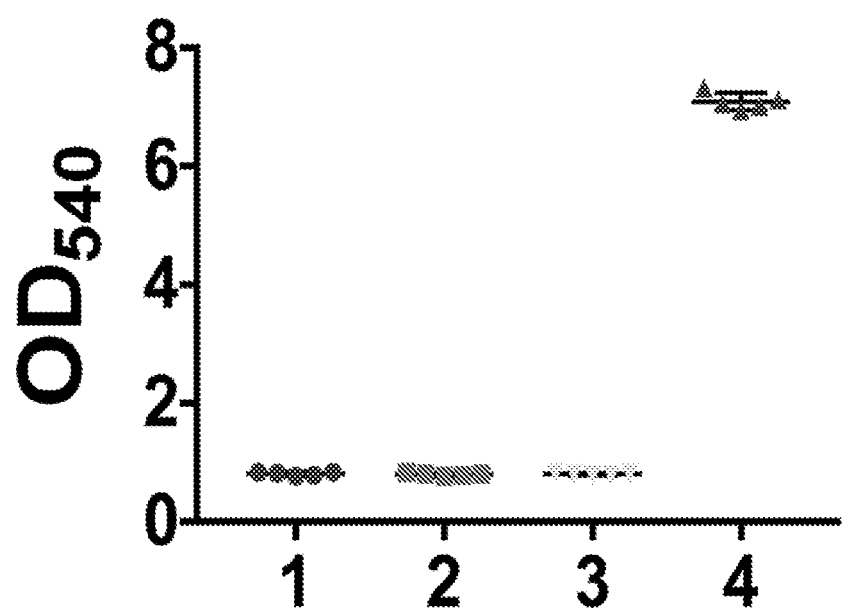
FIG. 14. Hemolytic activity of isogenic attenuated S. Typhi CVD 910 live vector strains expressing chromosomally encoded ClyA exported by over-expression of PagL. Samples from approximately 2×10$^7$ CFU of synchronized bacterial cultures were analyzed for hemolytic activity using sheep red blood cells, with five measurements per group. Lane 1: PBS; Lane 2: 910; Lane 3: 910ΔguaBA::clyA; Lane 4: 910ΔguaBA::clyA(pPagL).

As with our previous experiments with inducible outer membrane vesicles, we wished to monitor OMV export by measuring the hemolytic activity associated with ClyA-mediated vesiculation. Therefore, we integrated a cassette encoding ClyA into the guaBA locus of CVD 910 and then introduced pPagL into the resulting strain to create CVD 910ΔguaBA::clyA(pPagL). Note that in this particular strain, ClyA is acting as a surrogate hemolytic reporter for a chromosomally encoded OmpA protein, with over-expression of plasmid-encoded PagL expected to significantly improve rOMV export. All strains were grown at 37° C. into early-log phase growth, and hemolytic activity was measured at OD$_{540}$ for approximately 2×10$^7$ CFU of bacteria against sheep red blood cells. As shown in FIG. 14, no hemolytic activity was present in the vaccine strain CVD 910 as expected (lane 2). Surprisingly, the hemolytic activity of chromosomally encoded ClyA was not detected in CVD 910ΔguaBA::clyA (lane 3), due to the drop in copy number versus plasmid-encoded hemolytic activity observed for CVD 910(pSEC10) [see FIG. 3, lane 3]. However, significant hemolytic activity was observed when pPagL was introduced into 910ΔguaBA::clyA (lane 4), clearly demonstrating that over-expression of PagL induces excellent export of outer membrane proteins (i.e. ClyA in this case) via outer membrane vesicles. We therefore expect that OmpA and OmpW outer membrane proteins from A. baumannii and K. pneumoniae can be efficiently exported from S. Typhi-based carrier vaccines via rOMVs through over-expression of PagL to enhance delivery and improve protective efficacy.

Summary of Studies. Taken together, our results firmly establish the feasibility of developing an attenuated S. Typhi-based mucosal live vector vaccine that can efficiently express and deliver properly folded foreign outer membrane proteins to the surface of our live vector vaccine. These foreign antigens can be expressed from chromosomally integrated gene cassettes which will allow construction of a bivalent live vector vaccine that does not require large and potentially unstable multicopy expression plasmids for delivery of OmpA and OmpW antigens from A. baumannii and K. pneumoniae. To improve the clinical acceptability of our candidate live carrier vaccine, we have formally excluded any effect of AbOmpA expression on the virulence of our live vector. We have also engineered a unique outer membrane vesicle antigen delivery platform and successfully completed proof-of-principle studies demonstrating the efficiency of a PagL-mediated antigen delivery system using ClyA as a model outer membrane protein for export via recombinant rOMVs.

Experimental Design.

Part 1: Bivalent S. Typhi-based carrier vaccines, derived from S. Typhi Ty2 and expressing the protective outer membrane proteins OmpA and OmpW from either *A. baumannii* or *K. pneumoniae* will efficiently export both foreign antigens via PagL-mediated OMVs. We will verify high levels of cell associated OmpA and OmpW expression by western immunoblot analysis, surface expression by flow cytometry, and efficient extracellular export in purified OMVs.

Figure 5:
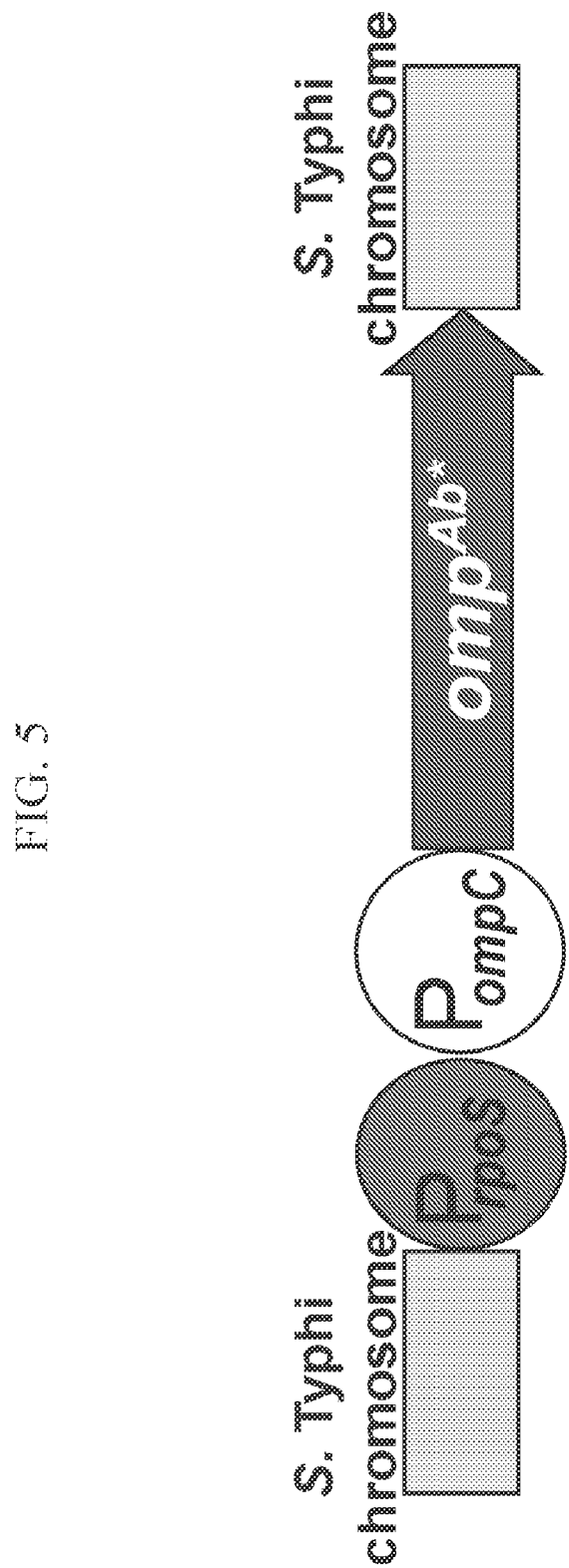
FIG. 5. Strategy for stable chromosomal integration into CVD 910 of cassettes encoding protective outer membrane protein antigens from *A. baumannii*. All cassettes are engineered such that the *A. baumannii* allele is primarily controlled by the osmotically induced $P_{ompC}$ promoter. Chromosomal integration is carried out such that the inducible promoter of the chromosomal target is preserved, creating transcriptional fusions in which differential expression of *A. baumannii* antigens is controlled at two levels, to avoid over-attenuation by antigens (as evidenced by hemolytic activity) is dependent on viable organisms and not lysis of bacteria.

We will construct pathogen-specific bivalent carrier vaccines targeting both OmpA and OmpW from either *A. baumannii* or *K. pneumoniae*; both antigens will be encoded by chromosomally integrated synthetic gene cassettes. Given that available data from OmpA-based adjuvanted subunit vaccines conferred only partial protection against challenge in experimental animal models, we hypothesize that inclusion of both OmpA and OmpW in a bivalent vaccine against a single MDR pathogen will confer maximum protection against infection; we can then increase the breadth of protection by mixing mono-specific vaccines. Chromosomally integrated cassettes will be transcriptionally regulated by nested promoters, allowing induction by either growth phase or environmental signals (such as osmolarity) likely to be encountered in vivo by vaccines after mucosal immunization (FIG. 5). This strategy was successfully exploited by our group to engineer a mucosal plague vaccine using CVD 910, which proved both immunogenic and protective using a murine intranasal immunogenicity and challenge model[66]. Regulated chromosomal expression of OmpA and OmpW will avoid over-attenuation of the carrier vaccine by unregulated constitutive expression, which could also reduce immunogenicity by formation of inclusion bodies or reduced surface expression through saturation of membrane transport pathways[96,97].

Figure 6:
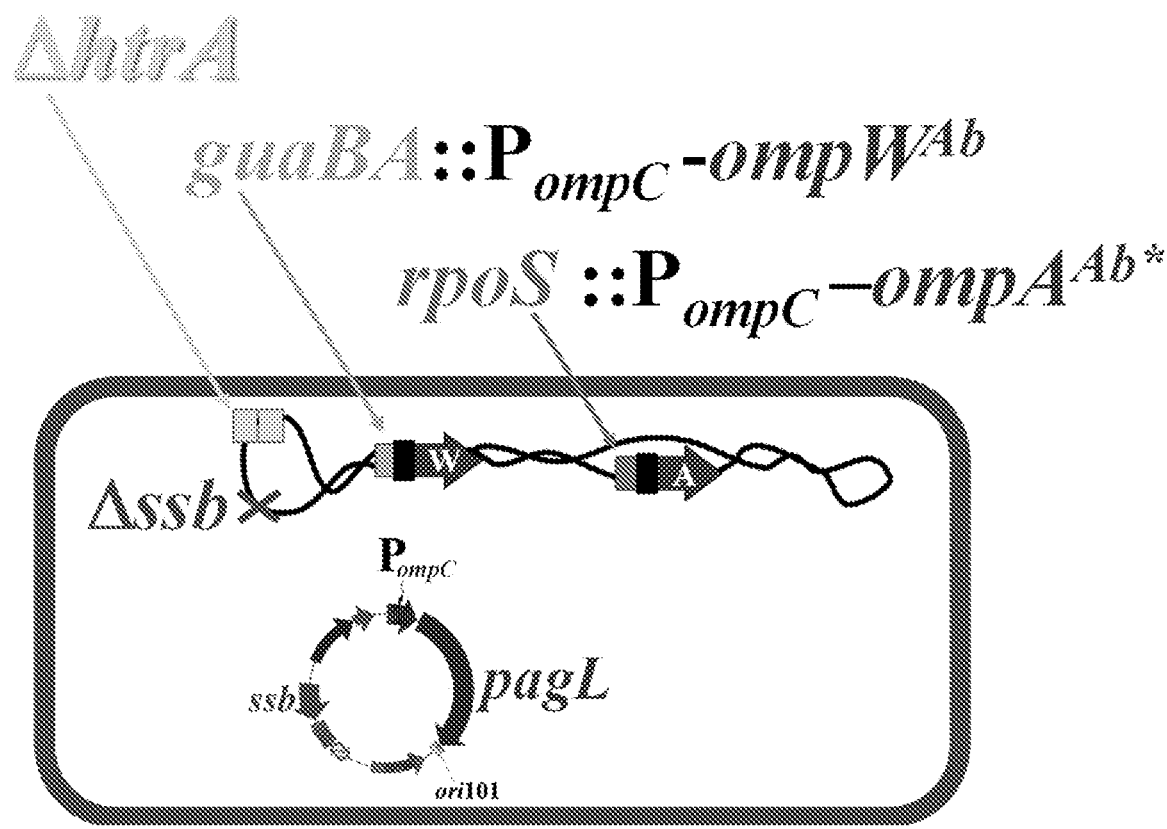
Figure 7:
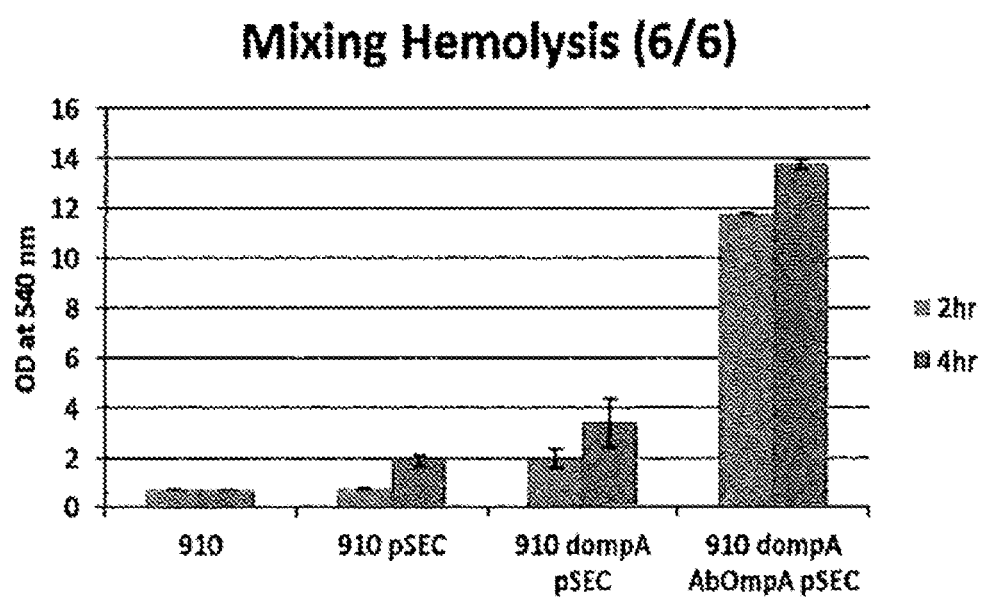
Figure 8:
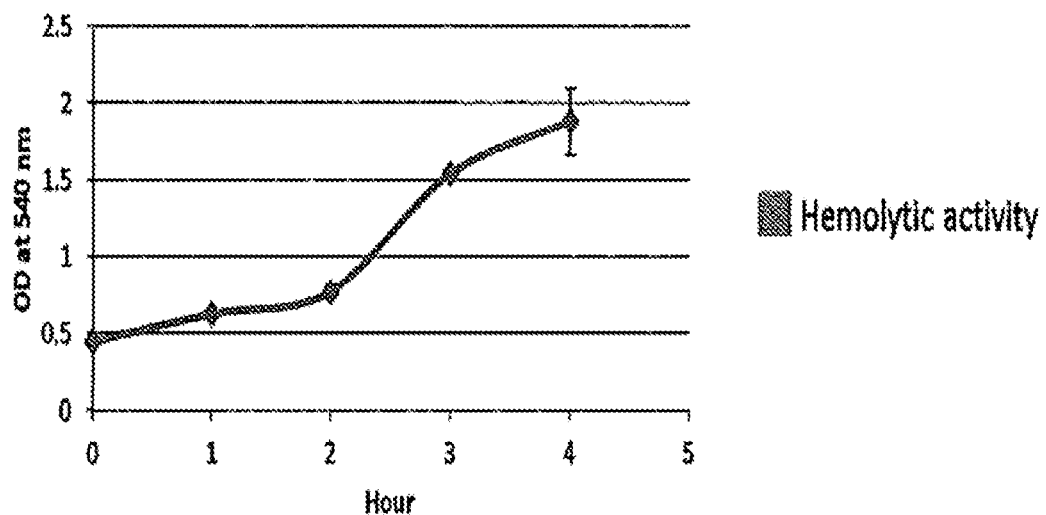
Figure 9:
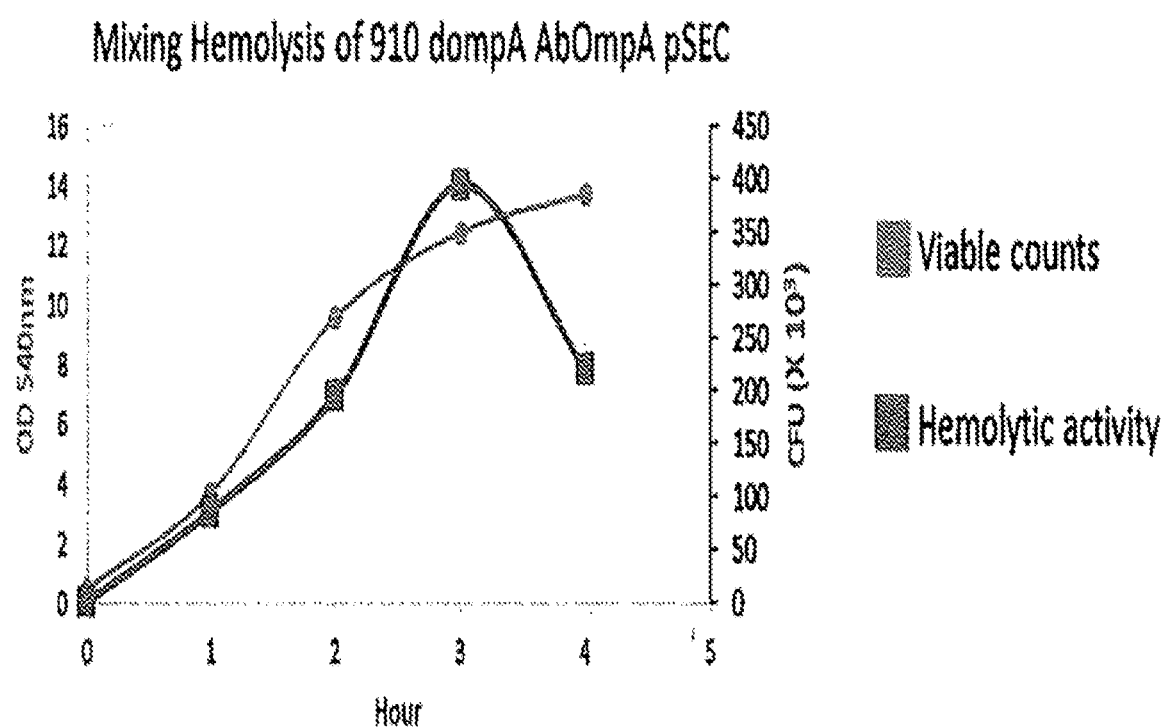
Figure 10:
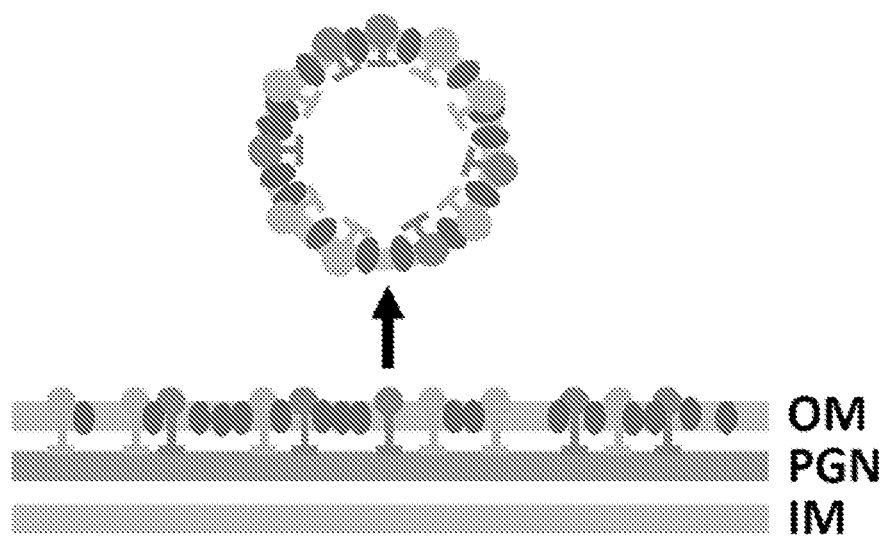
FIG. 10. An embodiment of an inducible OMV antigen delivery system.
Figure 11:
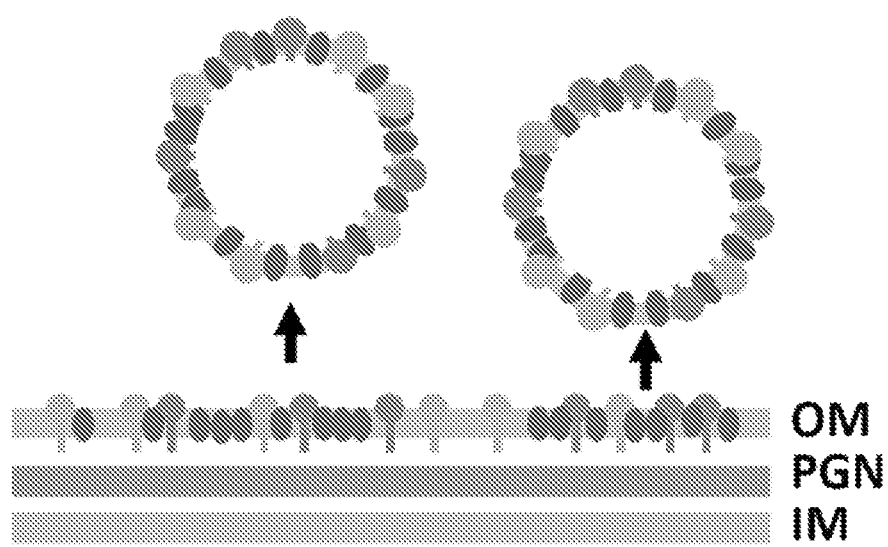
FIG. 11. An embodiment of an inducible OMV antigen delivery system.
Figure 12:
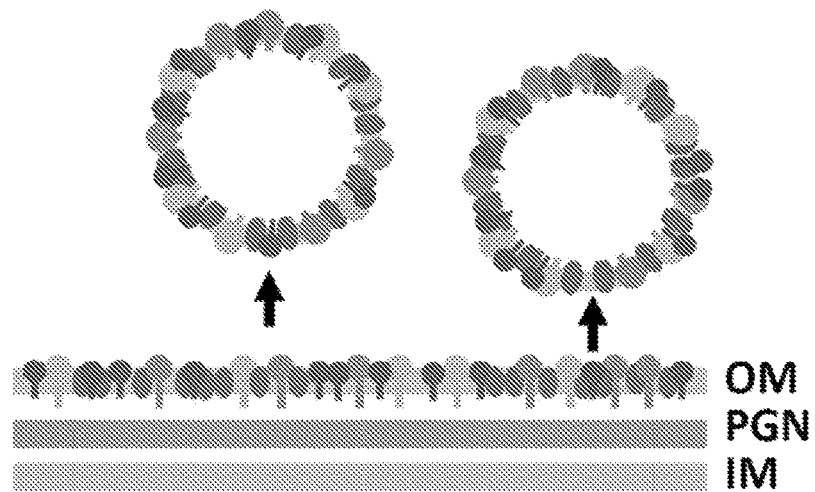
FIG. 12. An embodiment of an inducible OMV antigen delivery system.

Approach. For construction of a bivalent carrier vaccine against *A. baumannii*, we will integrate a synthetic $P_{ompC}$-ompW$^{Ab}$ cassette into the guaBA locus of our previously constructed monovalent CVD 910ΔompA$^{St}$ΔrpoS::ompA$^{Ab}$* carrier strain. We will then use our published non-antibiotic plasmid-stabilization system, based on expression of the essential single-stranded binding (SSB) protein, to construct a non-antibiotic version of the expression plasmid pPagL (expressing SSB). The resulting stabilized plasmid will be introduced into our bivalent carrier vaccine after deletion of chromosomal ssb, creating CVD 910ΔompA$^{St}$ΔguaBA::ompW$^{Ab}$ΔrpoS::ompA$^{Ab}$*Δssb (pPagL) carrier strain (FIG. 6 and hereafter referred to as CVD 910Ab). Using the identical strategy with synthetic gene cassettes, we will also construct the remaining carrier CVD 910Kp. For comparison in immunological studies, we will construct monovalent carrier strains expressing either OmpA or OmpW from both the guaBA and rpoS loci, to be designated as CVD 910-2A$^{Ab}$ and CVD 910-2W$^{Ab}$ for *A. baumannii*, and CVD910-2A$^{Kp}$ and CVD 910-2W$^{Kp}$ for *K. pneumoniae*. Since transcriptional control of the guaBA locus is controlled by growth rate[98], expression of OmpW in these carriers will be metabolically synchronized with the growth rate of the live vector; expression of OmpA from rpoS will be independently controlled by induction in stationary phase growth[99]. This tiered expression strategy will allow synthesis of both OmpA and OmpW to be metabolically synchronized with the growth rate and fitness of the live carrier vaccine in the host, thereby avoiding over-attenuation from inappropriately high pulses of both foreign antigens synthesized all at once[69]. We will confirm expression of both OmpA and OmpW by western immunoblot analysis using antisera either already in hand or raised in mice immunized with purified proteins by our group. We will also use these antibodies to examine the efficiency of co-expression of both OmpA and OmpW on the surface of each bivalent carrier vaccine candidate by flow cytometry. In addition, we will purify monovalent and bivalent outer membrane vesicles from the respective carrier strains, using well-characterized published protocols developed for use with S. Typhimurium[100], and verify reduced reactogenicity by measuring NF-κB-dependent luciferase activity through TLR4 activation for rOMVs vs unmodified OMVs from carriers without pPagL[2,3]. Hereafter, monovalent OMVs will be designated as OMV$^{AbOmpA}$ and OMV$^{AbOmpW}$ from *A. baumannii*-specific carriers, and OMV$^{KpOmpA}$ and OMV$^{KpOmpW}$ from *K. pneumoniae*-specific carriers; bivalent vesicles will be designated as OMV$^{Ab}$ and OMV$^{Kp}$ from *A. baumannii* and *K. pneumoniae* respectively. Unmodified OMVs will be prepared from CVD 910(pPagL) in which no foreign antigens are encoded (designated as OMV$^{910}$).

We can increase the level of chromosomal expression by integrating additional copies of the synthetic cassette. Since construction of CVD 910 was accomplished by attenuating deletion mutations in guaBA and htrA, we can integrate into the remaining htrA locus, or perhaps the ssb locus deleted for introduction of pPagL.

Part 2. Bivalent S. Typhi-based carrier vaccines efficiently expressing OmpA and OmpW from either *A. baumannii* or *K. pneumoniae* will elicit protection against challenge in mice.

The goal of this example is to develop mucosal vaccines against potentially lethal infections with MDR *A. baumannii* and *K. pneumoniae*. We will accomplish this by successfully completing proof-of-concept efficacy studies demonstrating protection against sepsis and pneumonia in mucosally immunized mice challenged either by the intraperitoneal or intranasal route respectively. We will first examine protection elicited using only carrier strains or purified rOMVs (i.e. homologous immunization strategy; Part 2A) or a heterologous immunization strategy in which animals receive sequential immunizations with carrier vaccine and rOMVs (Part 2B); we have observed superior immunity and protection in mice using a heterologous prime-boost strategy[66,76]. Although the primary endpoint for these studies is protective efficacy, we will also investigate potential humoral and cellular correlates of protection. Capsule-independent CD4$^+$ Th17-mediated protection against multiple serotypes of *K. pneumoniae* has been reported[31], and CD4$^+$ Th17-mediated protection against *A. baumannii* infections has recently been proposed[1]. Therefore, in addition to measuring antigen-specific serum IgG and IgA responses, we will specifically examine potential correlations between antigen-specific CD4$^+$ Th17 responses and protection.

Part 2A. Protective immunity elicited by a homologous prime-boost immunization strategy.

Approach. The immunogenicity of the monovalent and bivalent carrier vaccines established in Part 1 will be evaluated in BALB/c mice randomized into 5 groups and immunized intranasally (IN) on days 0 and 28 with ~5×10$^9$ colony forming units (CFU) as detailed in Table 2, Part 2A, experiment 1. For immunization of mice with purified rOMVs (Part 2A, experiment 2), we will conduct a dose-escalating pilot study in mice immunized once IN with non-adjuvanted bivalent rOMVs in increasing doses of 1 μg, 5 μg, and 10 μg, with the intent to elicit at least 50% protection based on previously published protection studies using OMVs purified from *A. baumannii*[26,27] and *K. pneumoniae*[30] in which at least 2 doses were given intramuscularly. The dose conferring 50% protection will then be tested for full protection in Experiment 2 in which mice will receive two doses of rOMV IN on days 0 and 28. Antigen-specific serum IgG and IgG isotypes will be measured by ELISA from sera collected on days 0, 14, 28, and 41, as previously described by our group[63,102]. In an attempt to correlate mucosal immunity with protection, we will also measure OMP-specific sIgA in pulmonary washes collected on day 41 as previously described[5,6]. Mice will then be challenged on day 42 with fully virulent *A. baumannii* strain LAC-4[4] or fully virulent *K. pneumoniae* B5055[103]; groups will be equally divided and half challenged IN with either $1 \times 10^8$ CFU of LAC-4 or $5 \times 10^4$ CFU of B5055 to evaluate protective efficacy against pneumonic challenge; the remaining immunized mice will be challenged intraperitoneally (IP) with $1 \times 10^6$ CFU of LAC-4[4,5] or $1 \times 10^5$ CFU of B5055 to determine protective efficacy against septic dissemination. Survival will be scored in both models 7 days post-challenge (i.e. day 49). To examine OMP-specific Th17 responses, we will harvest both lungs and spleens from immunized but not yet challenged mice on day 41 (5 mice) and challenged mice on day 49; we will also quantify bacterial tissue burden from blood, lungs and spleens after challenge, both from moribund mice as well as from protected mice following euthanasia 7 days post-challenge. We will purify splenocytes and pulmonary lymphoid cells from harvested tissue, stimulate either with PBS, $OMV^{Ab}$, or $OMV^{Kp}$, and measure Th17 effector cytokines IL-17A and IL-22 as previously described[31]. Since other cells such as γδ T cells and NK cells are also able to produce these cytokines[104-108], we will not only segregate them (NK and as γδ T cells) in different fluorescent channels, but also confirm that the mononuclear cells producing these cytokines are indeed CD4+ Th17 by assaying for the transcription factor ROR-γt. Moreover, we will also evaluate whether the CD4+ Th17 cells induced by vaccination and/or challenge show characteristics of memory cells (CD45RA/CD62L classification).

TABLE 2

Proposed mouse experiments for Part 2 (experiments with *A. baumannii* antigens only; identical study designs for experiments with *K. pneumoniae* antigens and challenged with Kp B5055)

| Group | Prime | Boost | Targeted Foreign Antigens | Challenge pathogen N* [route] |
|---|---|---|---|---|
| Part 2A; Experiment 1 - homologous prime-boost immunization strategy with carrier vaccine only ||||| 
| 1 | PBS | PBS | — | 20 Ab LAC 4 [IP (n = 5) or IN (n = 5)] |
| 2 | CVD 910 | CVD 910 | — | 25 Ab LAC 4 [IP (n = 10) or IN (n = 10)] |
| 3 | CVD 910-2A$^{Ab}$ | CVD 910-2A$^{Ab}$ | AbOmpA | 25 Ab LAC 4 [IP (n = 10) or IN (n = 10)] |
| 4 | CVD 910-2W$^{Ab}$ | CVD 910-2W$^{Ab}$ | AbOmpW | 25 Ab LAC 4 [IP (n = 10) or IN (n = 10)] |
| 5 | CVD 910Ab | CVD 910Ab | AbOmpA + AbOmpW | 25 Ab LAC 4 [IP (n = 10) or IN (n = 10)] |
| Part 2A; Experiment 2 - homologous prime-boost immunization strategy with OMV vaccine only ||||| 
| 1 | PBS | PBS | — | 20 Ab LAC 4 [IP (n = 5) or IN (n = 5)] |
| 2 | OMV$^{910}$ | OMV$^{910}$ | — | 25 Ab LAC 4 [IP (n = 10) or IN (n = 10)] |
| 3 | OMV$^{AbOmpA}$ | OMV$^{AbOmpA}$ | AbOmpA | 25 Ab LAC 4 [IP (n = 10) or IN (n = 10)] |
| 4 | OMV$^{AbOmpW}$ | OMV$^{AbOmpW}$ | AbOmpW | 25 Ab LAC 4 [IP (n = 10) or IN (n = 10)] |
| 5 | OMV$^{Ab}$ | OMV$^{Ab}$ | AbOmpA + AbOmpW | 25 Ab LAC 4 [IP (n = 10) or IN (n = 10)] |
| Part 2B; Experiment 1 - heterologous carrier prime/OMV boost immunization strategy ||||| 
| 1 | PBS | PBS | — | 20 Ab LAC 4 [IP (n = 5) or IN (n = 5)] |
| 2 | CVD 910 | OMV$^{910}$ | — | 25 Ab LAC 4 [IP (n = 10) or IN (n = 10)] |
| 3 | CVD 910-2A$^{Ab}$ | OMV$^{AbOmpA}$ | AbOmpA | 25 Ab LAC 4 [IP (n = 10) or IN (n = 10)] |
| 4 | CVD 910-2W$^{Ab}$ | OMV$^{AbOmpW}$ | AbOmpW | 25 Ab LAC 4 [IP (n = 10) or IN (n = 10)] |
| 5 | CVD 910Ab | OMV$^{Ab}$ | AbOmpA + AbOmpW | 25 Ab LAC 4 [IP (n = 10) or IN (n = 10)] |

*For measuring Th17 responses, spleens and lungs will be harvested from 5 PBS control mice on days 0 and 41, leaving 10 mice for challenge. Spleens and lungs will also be harvested from 5 immunized mice (Grps 2-5) on day 41, leaving 20 mice for challenge. A final set of tissues will be collected from post-challenged mice, including any mice that succumbed as well as from protected mice on day 49.

Part 2B. Protective immunity elicited by a heterologous prime-boost immunization strategy.

Approach. We will randomize BALB/c mice into 5 groups primed on day 0 with carrier vaccine and boosted on day 28 with rOMVs at a dose determined in Part 2A to confer 50% protection against challenge. As in Part 2A, humoral and mucosal immunity will be determined, mice will be challenged IP or IN on day 42 with either LAC-4 or B5055, and we will investigate whether CD4+ Th17 responses correlate with protection.

We can also test increasing doses up to 50 μg, which elicited protection against homologous challenge with either A. baumannii[26,27] and K. pneumoniae[30]. We expect the highest levels of immunity and protection to be elicited in mice immunized using a heterologous prime-boost immunization strategy. If significant protection is observed in mice challenged with B5055 (a K2 serotype), we will repeat the experiment and test for efficacy against other K. pneumoniae capsular types which we are currently testing for virulence in mice under separate funding.

Part 3: Carrier vaccines and purified OMVs, developed and tested in Parts 1 and 2 against challenge with a single pathogen will confer protection against challenge with both A. baumannii and K. pneumoniae in mice mucosally primed with doses containing a mix of the 2 carrier vaccines and boosted with mixed OMV preparations.

Approach. We will randomize mice into 5 groups, prime on day 0 and boost on day 28 as was done in Part 2. For immunization with rOMVs, we will combine individual doses used in Part 2B experiment 1 into a single dose; therefore, if 10 μg of either $OMV^{Ab}$ or $OMV^{Kp}$ were used in Part 2, then a combined rOMV vaccine dose would contain a total of 20 μg in a single dose. After boosting on day 28, mice will be homologously challenged IP or IN with either LAC-4 or B5055 on day 42. As in previous parts, humoral and mucosal immunity will be determined and $CD4^+$ Th17 responses correlated with protection.

We can increase the level of the affected individual vaccine in the mix to improve responses. As in Part 2B, if significant protection is observed in mice challenged with

TABLE 3

Proposed mouse experiments for Part 3 (vaccinated with both A. baumannii and K. pneumoniae antigens)

| Group | Prime | Boost | Targeted Foreign Antigens | Challenge pathogen N* [route] |
|---|---|---|---|---|
| | Part 3; Experiment 1 (experiment 2 will test an OMV prime/carrier boost reversed immunization strategy) |||||
| 1 | PBS | PBS | — | 20 Ab LAC 4 [IN (n = 5)] or KP B5055 [IN (n = 5)] |
| 2 | CVD 910 | $OMV^{910}$ | — | 25 Ab LAC 4 [IN (n = 10)] or KP B5055 [IN (n = 10)] |
| 3 | CVD 910-$2A^{Ab}$ + CVD 910-$2A^{Kp}$ | $OMV^{AbOmpA}$ + $OMV^{KpOmpA}$ | AbOmpA + KpOmpA | 25 Ab LAC 4 [IN (n = 10)] or KP B5055 [IN (n = 10)] |
| 4 | CVD 910-$2W^{Ab}$ + CVD 910-$2A^{Kp}$ | $OMV^{AbOmpW}$ + $OMV^{KpOmpW}$ | AbOmpW + KpOmpW | 25 Ab LAC 4 [IN (n = 10)] or KP B5055 [IN (n = 10)] |
| 5 | CVD 910Ab + CVD 910Kp | $OMV^{Ab}$ + $OMV^{Kp}$ | AbOmpA + KpOmpA + AbOmpW + KpOmpW | 25 Ab LAC 4 [IN (n = 10)] or KP B5055 [IN (n = 10)] |
| | Part 3; Experiment 3 |||||
| 1 | PBS | PBS | — | 15 Ab LAC 4 and KP B5055 [IN (n = 5)] |
| 2 | CVD 910 | $OMV^{910}$ | — | 15 Ab LAC 4 and KP B5055 [IN (n = 10)] |
| 3 | CVD 910-$2A^{Ab}$ + CVD 910-$2A^{Kp}$ | $OMV^{AbOmpA}$ + $OMV^{KpOmpA}$ | AbOmpA + KpOmpA | 15 Ab LAC 4 and KP B5055 [IN (n = 10)] |
| 4 | CVD 910-$2W^{Ab}$ + CVD 910-$2A^{Kp}$ | $OMV^{AbOmpW}$ + $OMV^{KpOmpW}$ | AbOmpW + KpOmpW | 15 Ab LAC 4 and KP B5055 [IN (n = 10)] |
| 5 | CVD 910Ab + CVD 910Kp | $OMV^{Ab}$ + $OMV^{Kp}$ | AbOmpA + KpOmpA + AbOmpW + KpOmpW | 15 Ab LAC 4 and KP B5055 [IN (n = 10)] |

*For measuring Th17 responses, spleens and lungs will be harvested from 5 PBS control mice on days 0 and 41, leaving 10 mice for challenge in experiments 1 and 2, and 5 for experiment 3. Spleens and lungs will also be harvested from 5 immunized mice (Grps 2-5) on day 41, leaving 20 mice for challenge in experiments 1 and 2, and 10 for experiment 3. A final set of tissues will be collected from post-challenged mice, including any mice that succumbed as well as from protected mice on day 48.

Here we will determine the protective efficacy for mice primed with a mixture of both carrier vaccines and boosted with a mixture of both $OMV^{Ab}$ and $OMV^{Kp}$ (Table 3, Part 3, experiment 1); we will also study if the order of carrier vaccine and rOMV administered in a heterologous prime-boost strategy affects protective efficacy against homologous challenge with either A. baumannii or K. pneumoniae (Part 3, experiment 2). In addition, a number of recent reports describe co-infection with antibiotic-resistant isolates of both A. baumannii and K. pneumoniae[109-113]. Therefore, we will also determine whether robust protection against polymicrobial infection can be achieved by challenging immunized mice with a lethal dose comprising both pathogens.

B5055 (a K2 serotype), we will repeat the experiment and test for efficacy against other K. pneumoniae capsular types.

CONCLUSION

In this example, we propose to use a single carrier vaccine platform, derived from an attenuated strain of S. Typhi and further engineered for deletion of StOmpA and inducible expression of PagL, to efficiently deliver rOMVs in which OmpA and OmpW proteins from either A. baumannii or K. pneumoniae are over-expressed on the surface of each exported vesicle. Expression and export of rOMVs will be induced in vivo by both growth rate and osmolarity following mucosal immunization. This example will generate at least four independent vaccines—2 individual live carrier vaccines and 2 purified rOMV-based acellular vaccines—against either *A. baumannii* or *K. pneumoniae*. In addition, we will have the unparalleled flexibility to mix carrier vaccines and rOMVs into single dose formulations of each type of vaccine to optimize vaccination. This platform could be used to develop mucosal vaccines against additional MDR pathogens including *Pseudomonas aeruginosa*, for which protective OmpA-like proteins have also proven to confer protection in experimental animal challenge models using mucosal *Salmonella*-based vaccines[14].

Example 2. Development of a PagL-Mediated Antigen Delivery Platform

Because ClyA is a hemolysin with cytopathic characteristics[94,95] that may reduce the clinical acceptability of candidate vaccine strains in which ClyA is over-expressed, we sought to develop a non-pathogenic alternative for inducing formation and export of OMVs based on PagL. We therefore constructed three synthetic pagL gene alleles, designated pagL v1 (SEQ ID NOS: 1 and 2), pagL v2 (SEQ ID NOS: 3 and 4), and pagL v3 (SEQ ID NOS: 5). These 3 versions differ in the 5'-terminal DNA sequences controlling the translation efficiency of each allele; this cautious engineering approach was adopted because the optimal translation efficiency of pagL assuring sufficient synthesis of biologically active PagL, while avoiding potentially lethal over-expression of this protein, was unknown at the time of these experiments. The amino acid sequence of pagL v2 and v3 is identical. To this end, pagL v1 carries an optimized ribosome binding site (RBS), an ATG start codon, and several optimized codons codon at the beginning of the gene to enhance translation efficiency. pagL v2 is similar to v1 but contains a GTG start codon to slightly reduce translation efficiency. pagL v3 is essentially identical to the wild type chromosomal sequence of the pagL gene naturally present within *Salmonella enterica* serovar Typhimurium. Therefore, we expected the highest levels of PagL synthesis from v1, with decreasing levels of synthesis from v2 and the lowest levels of synthesis from v3.

Figure 13:
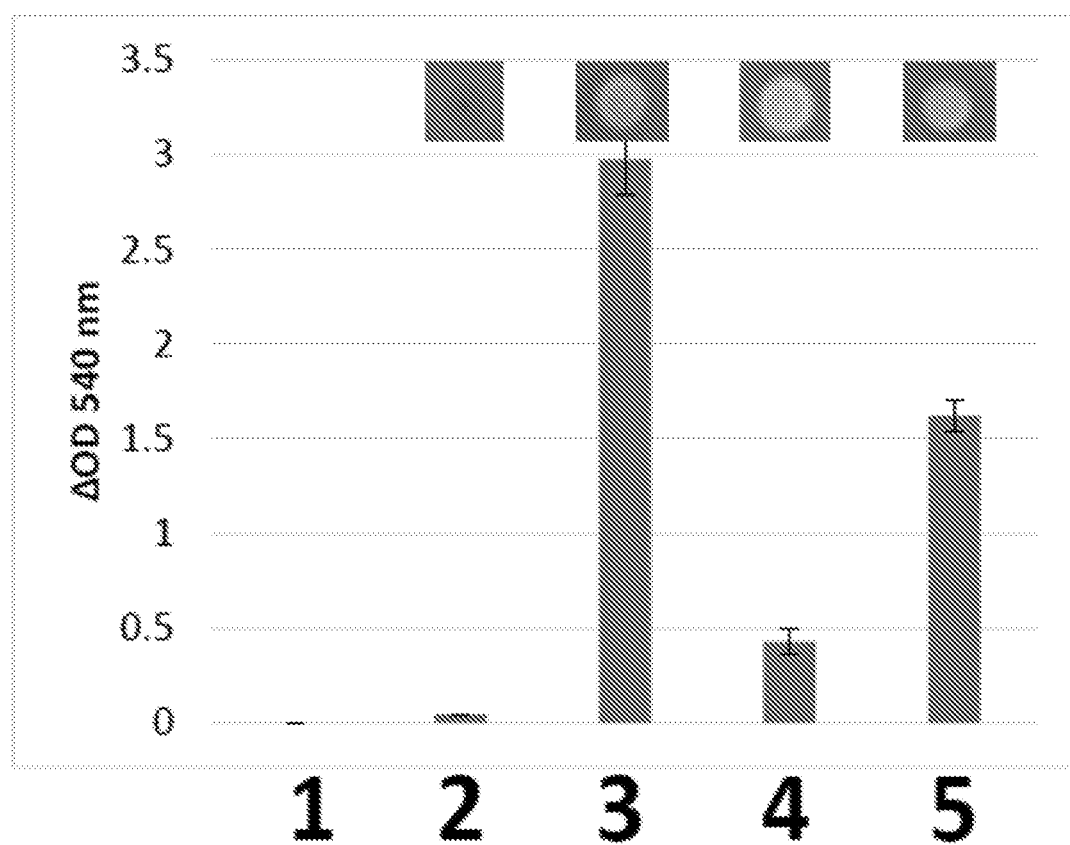
FIG. 13. Export of OmpA$^{Ab}$ in OMVs from CVD 910 live vaccine strains.

Each cassette was inserted as a BamHI-NheI fragment into our non-antibiotic low-copy-number expression plasmid pSEC10 digested with BamHI and NheI, replacing the clyA gene to create pPagL; the expected sequence of pPagL v1 is listed in SEQ ID NO:6. As with our previous experiments with inducible recombinant outer membrane vesicles (rOMVs), we wished to monitor OMV export by measuring the hemolytic activity associated with ClyA-containing vesicles. Therefore, we integrated a cassette encoding ClyA into the guaBA locus of CVD 910 and then introduced pPagL into the resulting strain to create CVD 910DguaBA::clyA(pPagL). Note that in this particular strain, ClyA is acting as a surrogate hemolytic reporter for a chromosomally encoded OmpA protein, with over-expression of plasmid-encoded PagL expected to significantly improve rOMV export. All strains were grown at 37° C. into early-log phase growth, and hemolytic activity was measured at $OD_{540}$ for approximately $2 \times 10^7$ CFU of bacteria against sheep red blood cells. As shown in FIG. 13, no hemolytic activity was present in the vaccine strain CVD 910 as expected (lane 2). Surprisingly, the hemolytic activity of chromosomally encoded ClyA was not detected in CVD 910DguaBA::clyA (lane 3), due to the drop in copy number versus plasmid-encoded hemolytic activity observed for CVD 910 (pSEC10). However, striking hemolytic activity was observed when pPagL was introduced into 910DguaBA::clyA (lane 4), clearly demonstrating that over-expression of PagL induces excellent export of rOMVs (containing ClyA as the surrogate outer membrane protein in this case).

We therefore expect that OmpA and OmpW outer membrane proteins from *A. baumannii* can be efficiently exported from S. Typhi-based carrier vaccines via rOMVs through over-expression of PagL to enhance delivery and improve protective efficacy. Further, one skilled in the art will readily appreciate that this technology serves as a delivery platform for development of live mucosal carrier vaccines against any bacterial pathogen for which targeted outer membrane protein(s) have the potential for eliciting protective efficacy. In addition, we point out that the rOMVs resulting from the construction of such carrier vaccines can be efficiently purified and used as parenteral vaccines in their own right, or used in the context of a heterologous mucosal prime-parenteral boost (or the reverse order) to further enhance the protective efficacy of such a vaccine platform.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

LITERATURE CITED

1. Elhenawy W, Bording-Jorgensen M, Valguarnera E, Haurat M F, Wine E, Feldman M F. LPS Remodeling triggers formation of outer membrane vesicles in *Salmonella. mBio* 2016; 7(4): e00940-16. doi:10.1128/mBio.00940-16.
2. Kawasaki K, Ernst R K, Miller S I. Deacylation and palmitoylation of lipid A by Salmonellae outer membrane enzymes modulate host signaling through Toll-like receptor 4. *J Endotoxin Res* 2004; 10(6): 439-44.
3. Kawasaki K, Ernst R K, Miller S I. 3-O-deacylation of lipid A by PagL, a PhoP/PhoQ-regulated deacylase of *Salmonella* typhimurium, modulates signaling through Toll-like receptor 4. *J Biol Chem* 2004; 279(19): 20044-8.
4. Harris G, Kuo Lee R, Lam C K, et al. A mouse model of *Acinetobacter baumannii*-associated pneumonia using a clinically isolated hypervirulent strain. *Antimicrob Agents Chemother* 2013; 57(8): 3601-13.
5. KuoLee R, Harris G, Yan H, et al. Intranasal immunization protects against *Acinetobacter baumannii*-associated pneumonia in mice. *Vaccine* 2015; 33(1): 260-7.
6. Chen W H, Kang T J, Bhattacharjee A K, Cross A S. Intranasal administration of a detoxified endotoxin vaccine protects mice against heterologous Gram-negative bacterial pneumonia. *Innate Immun* 2008; 14(5): 269-78.
7. McConnell M J, Actis L, Pachon J. *Acinetobacter baumannii*: human infections, factors contributing to pathogenesis and animal models. *FEMS Microbiol Rev* 2013; 37(2): 130-55.
8. Lin M F, Lan C Y. Antimicrobial resistance in *Acinetobacter baumannii*: From bench to bedside. *World journal of clinical cases* 2014; 2(12): 787-814.
9. Howard A, O'Donoghue M, Feeney A, Sleator R D. *Acinetobacter baumannii*: an emerging opportunistic pathogen. *Virulence* 2012; 3(3): 243-50.

10. Tumbarello M, Trecarichi E M, De Rosa F G, et al. Infections caused by KPC-producing *Klebsiella pneumoniae*: differences in therapy and mortality in a multicentre study. *J Antimicrob Chemother* 2015; 70(7): 2133-43.
11. Rodrigo-Troyano A, Sibila O. The respiratory threat posed by multidrug resistant Gram-negative bacteria. *Respirology* 2017.
12. Poolman J T, Wacker M. Extraintestinal Pathogenic *Escherichia coli*, a Common Human Pathogen: Challenges for Vaccine Development and Progress in the Field. *J Infect Dis* 2016; 213(1): 6-13.
13. United States Centers for Disease Control and Prevention. Antibiotic resistance threats in the United States, 2013. http://www.cdc.gov/drugresistance/pdf/ar-threats-2013-508.pdf.
14. World Health Organization. Antibacterial agents in clinical development: an analysis of the antibacterial clinical development pipeline, including tuberculosis. Geneva: World Health Organization; 2017. (WHO/EMP/IAU/2017.11). License: CC BY-NC-SA 3.0 IGO.
15. Chan A P, Sutton G, DePew J, et al. A novel method of consensus pan-chromosome assembly and large-scale comparative analysis reveal the highly flexible pan-genome of *Acinetobacter baumannii*. *Genome Biol* 2015; 16: 143.
16. Garcia-Quintanilla M, Pulido M R, Moreno-Martinez P, et al. Activity of host antimicrobials against multidrug-resistant *Acinetobacter baumannii* acquiring colistin resistance through loss of lipopolysaccharide. *Antimicrob Agents Chemother* 2014; 58(5): 2972-5.
17. Moffatt J H, Harper M, Harrison P, et al. Colistin resistance in *Acinetobacter baumannii* is mediated by complete loss of lipopolysaccharide production. *Antimicrob Agents Chemother* 2010; 54(12): 4971-7.
18. Gomez-Simmonds A, Uhlemann A C. Clinical Implications of Genomic Adaptation and Evolution of Carbapenem-Resistant *Klebsiella pneumoniae*. *J Infect Dis* 2017; 215(suppl_1): S18-s27.
19. Logan L K, Weinstein R A. The Epidemiology of Carbapenem-Resistant Enterobacteriaceae: The Impact and Evolution of a Global Menace. *J Infect Dis* 2017; 215(suppl_1): S28-s36.
20. Chen L, Mathema B, Chavda K D, DeLeo F R, Bonomo R A, Kreiswirth B N. Carbapenemase-producing *Klebsiella pneumoniae*: molecular and genetic decoding. *Trends Microbiol* 2014; 22(12): 686-96.
21. Pitout J D, Nordmann P, Poirel L. Carbapenemase-Producing *Klebsiella pneumoniae*, a Key Pathogen Set for Global Nosocomial Dominance. *Antimicrob Agents Chemother* 2015; 59(10): 5873-84.
22. Qamar S, Shaheen N, Shakoor S, Farooqi J, Jabeen K, Hasan R. Frequency of colistin and fosfomycin resistance in carbapenem-resistant Enterobacteriaceae from a tertiary care hospital in Karachi. *Infection and drug resistance* 2017; 10: 231-6.
23. Newton-Foot M, Snyman Y, Maloba M R B, Whitelaw A C. Plasmid-mediated mcr-1 colistin resistance in *Escherichia coli* and *Klebsiella* spp. clinical isolates from the Western Cape region of South Africa. *Antimicrobial resistance and infection control* 2017; 6: 78.
24. Mansour W, Haenni M, Saras E, et al. Outbreak of colistin-resistant carbapenemase-producing *Klebsiella pneumoniae* in Tunisia. *Journal of global antimicrobial resistance* 2017; 10: 88-94.
25. Granata G, Petrosillo N. Resistance to Colistin in *Klebsiella pneumoniae*: A 4.0 Strain? *Infect Dis Rep* 2017; 9(2): 7104.
26. McConnell M J, Rumbo C, Bou G, Pachon J. Outer membrane vesicles as an acellular vaccine against *Acinetobacter baumannii*. *Vaccine* 2011; 29(34): 5705-10.
27. Huang W, Yao Y, Long Q, et al. Immunization against multidrug-resistant *Acinetobacter baumannii* effectively protects mice in both pneumonia and sepsis models. *PLoS One* 2014; 9(6): e100727.
28. Garcia-Quintanilla M, Pulido M R, Pachon J, McConnell M J. Immunization with lipopolysaccharide-deficient whole cells provides protective immunity in an experimental mouse model of *Acinetobacter baumannii* infection. *PLoS One* 2014; 9(12): e114410.
29. McConnell M J, Dominguez-Herrera J, Smani Y, Lopez-Rojas R, Docobo-Perez F, Pachon J. Vaccination with outer membrane complexes elicits rapid protective immunity to multidrug-resistant *Acinetobacter baumannii*. *Infect Immun* 2011; 79(1): 518-26.
30. Lee W H, Choi H I, Hong S W, Kim K S, Gho Y S, Jeon S G. Vaccination with *Klebsiella pneumoniae*-derived extracellular vesicles protects against bacteria-induced lethality via both humoral and cellular immunity. *Exp Mol Med* 2015; 47: e183.
31. Chen K, McAleer J P, Lin Y, et al. Th17 cells mediate clade-specific, serotype-independent mucosal immunity. *Immunity* 2011; 35(6): 997-1009.
32. Pan Y J, Lin T L, Chen Y H, et al. Capsular types of *Klebsiella pneumoniae* revisited by wzc sequencing. *PLoS One* 2013; 8(12): e80670.
33. McClean S. Eight stranded beta-barrel and related outer membrane proteins: role in bacterial pathogenesis. *Protein and peptide letters* 2012; 19(10): 1013-25.
34. Krishnan S, Prasadarao N V. Outer membrane protein A and OprF: versatile roles in Gram-negative bacterial infections. *The FEBS journal* 2012; 279(6): 919-31.
35. Luo G, Lin L, Ibrahim A S, et al. Active and passive immunization protects against lethal, extreme drug resistant-*Acinetobacter baumannii* infection. *PLoS One* 2012; 7(1): e29446.
36. Badmasti F, Ajdary S, Bouzari S, Fooladi A A, Shahcheraghi F, Siadat S D. Immunological evaluation of OMV+Bap and AbOmpA+Bap as vaccine candidates against *Acinetobacter baumannii* sepsis infection. *Mol Immunol* 2015.
37. Huang W, Wang S, Yao Y, et al. OmpW is a potential target for eliciting protective immunity against *Acinetobacter baumannii* infections. *Vaccine* 2015; 33(36): 4479-85.
38. Marti S, Sanchez-Cespedes J, Oliveira E, Bellido D, Giralt E, Vila J. Proteomic analysis of a fraction enriched in cell envelope proteins of *Acinetobacter baumannii*. *Proteomics* 2006; 6 Suppl 1: S82-7.
39. Nwugo C C, Gaddy J A, Zimbler D L, Actis L A. Deciphering the iron response in *Acinetobacter baumannii*: A proteomics approach. *J Proteomics* 2011; 74(1): 44-58.
40. Schweppe D K, Harding C, Chavez J D, et al. Host-Microbe Protein Interactions during Bacterial Infection. *Chem Biol* 2015; 22(11): 1521-30.
41. Sato Y, Unno Y, Kawakami S, Ubagai T, Ono Y. Virulence characteristics of *Acinetobacter baumannii* clinical isolates vary with the expression levels of omps. *J Med Microbiol* 2017; 66(2): 203-12.
42. Sanchez-Encinales V, Alvarez-Marin R, Pachon-Ibanez M E, et al. Overproduction of Outer Membrane Protein A by *Acinetobacter baumannii* as a Risk Factor for Nosocomial Pneumonia, Bacteremia, and Mortality Rate Increase. *J Infect Dis* 2017; 215(6): 966-74.

43. Llobet E, March C, Gimenez P, Bengoechea J A. *Klebsiella pneumoniae* OmpA confers resistance to antimicrobial peptides. *Antimicrob Agents Chemother* 2009; 53(1): 298-302.
44. March C, Moranta D, Regueiro V, et al. *Klebsiella pneumoniae* outer membrane protein A is required to prevent the activation of airway epithelial cells. *J Biol Chem* 2011; 286(12): 9956-67.
45. Struve C, Forestier C, Krogfelt K A. Application of a novel multi-screening signature-tagged mutagenesis assay for identification of *Klebsiella pneumoniae* genes essential in colonization and infection. *Microbiology* 2003; 149(Pt 1): 167-76.
46. Kurupati P, Teh B K, Kumarasinghe G, Poh C L. Identification of vaccine candidate antigens of an ESBL producing *Klebsiella pneumoniae* clinical strain by immunoproteome analysis. *Proteomics* 2006; 6(3): 836-44.
47. Jeannin P, Renno T, Goetsch L, et al. OmpA targets dendritic cells, induces their maturation and delivers antigen into the MHC class I presentation pathway. *Nat Immunol* 2000; 1(6): 502-9.
48. Jeannin P, Magistrelli G, Goetsch L, et al. Outer membrane protein A (OmpA): a new pathogen-associated molecular pattern that interacts with antigen presenting cells-impact on vaccine strategies. *Vaccine* 2002; 20 Suppl 4: A23-7.
49. Jeannin P, Magistrelli G, Herbault N, et al. Outer membrane protein A renders dendritic cells and macrophages responsive to CCL21 and triggers dendritic cell migration to secondary lymphoid organs. *Eur J Immunol* 2003; 33(2): 326-33.
50. Jeannin P, Bottazzi B, Sironi M, et al. Complexity and complementarity of outer membrane protein A recognition by cellular and humoral innate immunity receptors. *Immunity* 2005; 22(5): 551-60.
51. Pichavant M, Taront S, Jeannin P, et al. Impact of bronchial epithelium on dendritic cell migration and function: modulation by the bacterial motif KpOmpA. *J Immunol* 2006; 177(9): 5912-9.
52. Kurupati P, Ramachandran N P, Poh C L. Protective efficacy of DNA vaccines encoding outer membrane protein A and OmpK36 of *Klebsiella pneumoniae* in mice. *Clin Vaccine Immunol* 2011; 18(1): 82-8.
53. Sengstock D M, Thyagarajan R, Apalara J, Mira A, Chopra T, Kaye K S. Multidrug-resistant *Acinetobacter baumannii*: an emerging pathogen among older adults in community hospitals and nursing homes. *Clin Infect Dis* 2010; 50(12): 1611-6.
54. Prabaker K, Lin M Y, McNally M, et al. Transfer from high-acuity long-term care facilities is associated with carriage of *Klebsiella pneumoniae* carbapenemase-producing Enterobacteriaceae: a multihospital study. *Infect Control Hosp Epidemiol* 2012; 33(12): 1193-9.
55. Thurlow C J, Prabaker K, Lin M Y, Lolans K, Weinstein R A, Hayden M K. Anatomic sites of patient colonization and environmental contamination with *Klebsiella pneumoniae* carbapenemase-producing Enterobacteriaceae at long-term acute care hospitals. *Infect Control Hosp Epidemiol* 2013; 34(1): 56-61.
56. O'Shea M K. *Acinetobacter* in modern warfare. *Int J Antimicrob Agents* 2012; 39(5): 363-75.
57. Tacket C O, Sztein M, Losonsky G, et al. Safety of live oral *Salmonella* typhi vaccine strains with deletions in htrA and aroC aroD and immune responses in humans. *Infect Immun* 1997; 65(2): 452-6.
58. Wang J Y, Noriega F, Galen J E, Barry E M, Levine M M. Constitutive expression of the Vi polysaccharide capsular antigen in attenuated *Salmonella enterica* serovar Typhi oral vaccine strain CVD 909. *Infect Immun* 2000; 68(8): 4647-52.
59. Wang J Y, Pasetti M F, Noriega F, et al. Construction, genotypic and phenotypic characterization, and immunogenicity of attenuated DguaBA *Salmonella enterica* serovar Typhi strain CVD 915. *Infect Immun* 2001; 69(8): 4734-41.
60. Tacket C O, Sztein M, Wasserman S S, et al. Phase 2 clinical trial of attenuated *Salmonella enterica* serovar Typhi oral live vector vaccine CVD 908-htrA in U.S. volunteers. *Infect Immun* 2000; 68: 1196-201.
61. Bumann D, Behre C, Behre K, et al. Systemic, nasal and oral live vaccines against *Pseudomonas aeruginosa*: a clinical trial of immunogenicity in lower airways of human volunteers. *Vaccine* 2010; 28(3): 707-13.
62. Galen J E, Zhao L, Chinchilla M, et al. Adaptation of the endogenous *Salmonella enterica* serovar Typhi clyA-encoded hemolysin for antigen export enhances the immunogenicity of anthrax protective antigen domain 4 expressed by the attenuated live-vector vaccine strain CVD 908-htrA. *Infect Immun* 2004; 72(12): 7096-106.
63. Galen J E, Chinchilla M, Pasetti M F, et al. Mucosal immunization with attenuated *Salmonella enterica* serovar Typhi expressing protective antigen of anthrax toxin (PA83) primes monkeys for accelerated serum antibody responses to parenteral PA83 vaccine. *J Infect Dis* 2009; 199(3): 326-35.
64. Galen J E, Wang J Y, Chinchilla M, et al. A new generation of stable, nonantibiotic, low-copy-number plasmids improves immune responses to foreign antigens in *Salmonella enterica* serovar Typhi live vectors. *Infect Immun* 2010; 78(1): 337-47.
65. Wang J Y, Harley R H, Galen J E. Novel methods for expression of foreign antigens in live vector vaccines. *Hum Vaccin Immunother* 2013; 9(7): 1558-64.
66. Galen J E, Wang J Y, Carrasco J A, et al. A Bivalent Typhoid Live Vector Vaccine Expressing both Chromosome- and Plasmid-Encoded *Yersinia pestis* Antigens Fully Protects against Murine Lethal Pulmonary Plague Infection. *Infect Immun* 2015; 83(1): 161-72.

67. Chase J W, Williams K R. Single-stranded DNA binding proteins required for DNA replication. *Annual Reviews in Biochemistry* 1986; 55: 103-36.

68. Lohman T M, Ferrari M E. *Escherichia coli* single-stranded DNA-binding protein: multiple DNA-binding modes and cooperativities. *Annual Reviews in Biochemistry* 1994; 63: 527-70.

69. Galen J E, Curtiss R, 3rd. The delicate balance in genetically engineering live vaccines. *Vaccine* 2014; 32(35): 4376-85.

70. Kang H Y, Curtiss R, III. Immune responses dependent on antigen location in recombinant attenuated *Salmonella* typhimurium vaccines following oral immunization. *FEMS Immunol Med Microbiol* 2003; 37(2-3): 99-104.

71. Carter P B, Collins F M. Growth of typhoid and paratyphoid bacilli in intravenously infected mice. *Infect Immun* 1974; 10(4): 816-22.

72. O'Brien A D. Innate resistance of mice to *Salmonella* typhi infection. *Infect Immun* 1982; 38(3): 948-52.

73. Galen J E, Gomez-Duarte O G, Losonsky G, et al. A murine model of intranasal immunization to assess the immunogenicity of attenuated *Salmonella* typhi live vector vaccines in stimulating serum antibody responses to expressed foreign antigens. *Vaccine* 1997; 15(6/7): 700-8.

74. Orr N, Galen J E, Levine M M. Expression and immunogenicity of a mutant diphtheria toxin molecule, CRM 197, and its fragments in *Salmonella* typhi vaccine strain CVD 908-htrA. *Infect Immun* 1999; 67(8): 4290-4.
75. Barry E M, Gomez-Duarte O G, Chatfield S, et al. Expression and immunogenicity of pertussis toxin S1 subunit-tetanus toxin fragment C fusions in *Salmonella* typhi vaccine strain CVD 908. *Infect Immun* 1996; 64(10): 4172-81.
76. Vindurampulle C J, Cuberos L F, Barry E M, Pasetti M F, Levine M M. Recombinant *Salmonella enterica* serovar Typhi in a prime-boost strategy. *Vaccine* 2004; 22(27-28): 3744-50.
77. Capozzo A V, Cuberos L, Levine M M, Pasetti M F. Mucosally delivered *Salmonella* live vector vaccines elicit potent immune responses against a foreign antigen in neonatal mice born to naive and immune mothers. *Infect Immun* 2004; 72(8): 4637-46.
78. Ramirez K, Capozzo A V, Lloyd S A, Sztein M B, Nataro J P, Pasetti M F. Mucosally delivered *Salmonella* Typhi expressing the *Yersinia pestis* F1 antigen elicits mucosal and systemic immunity early in life and primes the neonatal immune system for a vigorous anamnestic response to parenteral F1 boost. *J Immunol* 2009; WW(XX): YY-ZZ.

79. Ramirez K, Ditamo Y, Galen J E, Baillie L W, Pasetti M F. Mucosal priming of newborn mice with S. Typhi Ty21a expressing anthrax protective antigen (PA) followed by parenteral PA-boost induces B and T cell-mediated immunity that protects against infection bypassing maternal antibodies. *Vaccine* 2010; 28(37): 6065-75.

80. Gomez-Duarte O G, Pasetti M F, Santiago A, Sztein M B, Hoffman S L, Levine M M. Expression, extracellular secretion, and immunogenicity of the *Plasmodium falciparum* sporozoite surface protein 2 in *Salmonella* vaccine strains. *Infect Immun* 2001; 69(2): 1192-8.

81. Pasetti M F, Levine M M, Sztein M B. Animal models paving the way for clinical trials of attenuated *Salmonella enterica* serovar Typhi live oral vaccines and live vectors. *Vaccine* 2003; 21(5-6): 401-18.

82. Galen J E, Pasetti M F, Tennant S M, Olvera-Ruiz P, Sztein M B, Levine M M. *Salmonella enterica* serovar Typhi live vector vaccines finally come of age. *Immunol Cell Biol* 2009; 87(5): 400-12.

83. Tacket C O, Galen J, Sztein M B, et al. Safety and immune responses to attenuated *Salmonella enterica* serovar Typhi oral live vector vaccines expressing tetanus toxin fragment C. *Clin Immunol* 2000; 97(2): 146-53.

84. Tacket C O, Pasetti M F, Sztein M B, Livio S, Levine M M. Immune responses to an oral typhoid vaccine strain that is modified to constitutively express Vi capsular polysaccharide. *J Infect Dis* 2004; 190(3): 565-70.

85. Stratford R, McKelvie N D, Hughes N J, et al. Optimization of *Salmonella enterica* serovar typhi DaroC DssaV derivatives as vehicles for delivering heterologous antigens by chromosomal integration and in vivo inducible promoters. *Infect Immun* 2005; 73(1): 362-8.

86. Khan S, Chatfield S, Stratford R, et al. Ability of SPI2 mutant of S. typhi to effectively induce antibody responses to the mucosal antigen enterotoxigenic *E. coli* heat labile toxin B subunit after oral delivery to humans. *Vaccine* 2007; 25(21): 4175-82.

87. Park J S, Lee W C, Yeo K J, et al. Mechanism of anchoring of OmpA protein to the cell wall peptidoglycan of the gram-negative bacterial outer membrane. *FASEB J* 2012; 26(1): 219-28.

88. Trent M S, Pabich W, Raetz C R, Miller S I. A PhoP/PhoQ-induced Lipase (PagL) that catalyzes 3-O-deacylation of lipid A precursors in membranes of *Salmonella* typhimurium. *J Biol Chem* 2001; 276(12): 9083-92.

89. Tacket C O, Hone D M, Curtiss Iii R, et al. Comparison of the safety and immunogenicity of DaroC DaroD and Dcya Dcrp *Salmonella* Typhi strains in adult volunteers. *Infect Immun* 1992; 60(2): 536-41.

90. Choi C H, Hyun S H, Lee J Y, et al. *Acinetobacter baumannii* outer membrane protein A targets the nucleus and induces cytotoxicity. *Cell Microbiol* 2008; 10(2): 309-19.

91. Lee J S, Choi C H, Kim J W, Lee J C. *Acinetobacter baumannii* outer membrane protein A induces dendritic cell death through mitochondrial targeting. *Journal of microbiology* (Seoul, Korea) 2010; 48(3): 387-92.

92. Wai S N, Lindmark B, Soderblom T, et al. Vesicle-mediated export and assembly of pore-forming oligomers of the enterobacterial ClyA cytotoxin. *Cell* 2003; 115(1): 25-35.

93. Sansonetti P J, Ryter A, Clerc P, Maurelli A T, Mounier J. Multiplication of *Shigella flexneri* within HeLa cells: lysis of the phagocytic vacuole and plasmid-mediated contact hemolysis. *Infect Immun* 1986; 51(2): 461-9.

94. Ludwig A, Bauer S, Benz R, Bergmann B, Goebel W. Analysis of the SlyA-controlled expression, subcellular localization and pore-forming activity of a 34 kDa haemolysin (ClyA) from *Escherichia coli* K-12. *Mol Microbiol* 1999; 31(2): 557-67.

95. Lai X H, Arencibia I, Johansson A, et al. Cytocidal and apoptotic effects of the ClyA protein from *Escherichia coli* on primary and cultured monocytes and macrophages. *Infect Immun* 2000; 68(7): 4363-7.

96. Mushtaq A U, Park J S, Bae S H, et al. Ligand-Mediated Folding of the OmpA Periplasmic Domain from *Acinetobacter baumannii*. *Biophys J* 2017; 112(10): 2089-98.

97. Schiffrin B, Calabrese A N, Higgins A J, et al. Effects of periplasmic chaperones and membrane thickness on BamA-catalysed outer membrane protein folding. *J Mol Biol* 2017.

98. Davies I J, Drabble W T. Stringent and growth-rate-dependent control of the gua operon of *Escherichia coli* K-12. *Microbiology* 1996; 142(Pt 9): 2429-37.

99. Hengge-Aronis R. Signal transduction and regulatory mechanisms involved in control of the sigma(S) (RpoS) subunit of RNA polymerase. *Microbiol Mol Biol Rev* 2002; 66(3): 373-95, table.

100. Rossi O, Caboni M, Negrea A, et al. Toll-Like Receptor Activation by Generalized Modules for Membrane Antigens from Lipid A Mutants of *Salmonella enterica* Serovars Typhimurium and *Enteritidis*. *Clin Vaccine Immunol* 2016; 23(4): 304-14.

101. Yan Z, Yang J, Hu R, Hu X, Chen K. *Acinetobacter baumannii* Infection and IL-17 Mediated Immunity. *Mediators Inflamm* 2016; 2016: 9834020.

102. Gat O, Galen J E, Tennant S, et al. Cell-associated flagella enhance the protection conferred by mucosally-administered attenuated *Salmonella* Paratyphi A vaccines. *PLoS Negl Trop Dis* 2011; 5(11): e1373.

103. Kumar V, Chhibber S. Acute lung inflammation in *Klebsiella pneumoniae* B5055-induced pneumonia and sepsis in BALB/c mice: a comparative study. *Inflammation* 2011; 34(5): 452-62.

104. O'Brien R L, Roark C L, Born W K. IL-17-producing gammadelta T cells. *Eur J Immunol* 2009; 39(3): 662-6.

105. Passos S T, Silver J S, O'Hara A C, Sehy D, Stumhofer J S, Hunter C A. IL-6 promotes NK cell production of IL-17 during toxoplasmosis. *J Immunol* 2010; 184(4): 1776-83.
106. Yao S, Huang D, Chen C Y, et al. Differentiation, distribution and gammadelta T cell-driven regulation of IL-22-producing T cells in tuberculosis. *PLoS Pathog* 2010; 6(2): e1000789.
107. Chien Y H, Zeng X, Prinz I. The natural and the inducible: interleukin (IL)-17-producing gammadelta T cells. *Trends Immunol* 2013; 34(4): 151-4.
108. Xu X, Weiss I D, Zhang H H, et al. Conventional NK cells can produce IL-22 and promote host defense in *Klebsiella pneumoniae* pneumonia. *J Immunol* 2014; 192 (4): 1778-86.
109. Perez F, Endimiani A, Ray A J, et al. Carbapenem-resistant *Acinetobacter baumannii* and *Klebsiella pneumoniae* across a hospital system: impact of post-acute care facilities on dissemination. *J Antimicrob Chemother* 2010; 65(8): 1807-18.
110. Mammina C, Bonura C, Vivoli A R, et al. Co-colonization with carbapenem-resistant *Klebsiella pneumoniae* and *Acinetobacter baumannii* in intensive care unit patients. *Scand J Infect Dis* 2013; 45(8): 629-34.
111. Zhang H M, Liu D W, Wang X T, Long Y, Chen H. Bloodstream infection with carbapenem-resistant *Klebsiella pneumoniae* and multidrug-resistant *Acinetobacter baumannii*: a case report. *Chin Med Sci J* 2014; 29(1): 51-4.
112. Timofte D, Dan M, Maciuca I E, et al. Emergence of concurrent infections with colistin-resistant ESBL-positive *Klebsiella pneumoniae* and OXA-23-producing *Acinetobacter baumannii* sensitive to colistin only in a Romanian cardiac intensive care unit. *Eur J Clin Microbiol Infect Dis* 2015; 34(10): 2069-74.
113. Hammerum A M, Littauer P, Hansen F. Detection of *Klebsiella pneumoniae* co-producing NDM-7 and OXA-181, *Escherichia coli* producing NDM-5 and *Acinetobacter baumannii* producing OXA-23 in a single patient. *Int J Antimicrob Agents* 2015; 46(5): 597-8.
114. Zhang M, Sun C, Gu J, et al. *Salmonella* Typhimurium strain expressing OprF-OprI protects mice against fatal infection by *Pseudomonas aeruginosa*. *Microbiol Immunol* 2015; 59(9): 533-44.

We claim:

1. An immunogenic live *Salmonella* Typhi vector that has been engineered to express one or more heterologous antigens from a pathogen, wherein the heterologous antigen comprises outer membrane protein OmpW or an antigenic fragment or variant thereof and comprises outer membrane protein OmpA or an antigenic fragment or variant thereof, wherein the live *Salmonella* Typhi vector is capable of delivering immunogenic, recombinant outer membrane vesicles (rOMVs) to a mucosal tissue when administered to a subject, wherein the vesicles comprise the heterologous antigens, wherein the *Salmonella* Typhi vector has been engineered to overexpress a lipid A deacylase PagL.

2. The *Salmonella* Typhi vector of claim 1, wherein the pathogen is selected from *Acinetobacter baumannii* and *Klebsiella pneumoniae*.

3. The *Salmonella* Typhi vector of claim 1, wherein the outer membrane proteins are each encoded by a nucleic acid sequence that is chromosomally integrated in S. Typhi.

4. The *Salmonella* Typhi vector of claim 1, wherein a homologous S. Typhi outer membrane protein has been deleted or inactivated.

5. The *Salmonella* Typhi vector of claim 1, wherein the outer membrane proteins each encoded by a nucleic acid sequence are each inserted into an S. Typhi locus selected from the group consisting of guaBA, rpoS, htrA, ssb, and combinations thereof.

6. The *Salmonella* Typhi vector of claim 1, wherein at least one outer membrane protein encoded by a nucleic acid sequence is inserted into the rpoS locus of S. Typhi.

7. The *Salmonella* Typhi vector of claim 1, wherein the outer membrane protein OmpW encoded by a nucleic acid sequence is chromosomally integrated into the guaBA locus.

8. The *Salmonella* Typhi vector of claim 1, wherein the outer membrane protein OmpA encoded by a nucleic acid sequence is chromosomally integrated into the rpoS locus.

9. The *Salmonella* Typhi vector of claim 1, wherein the OmpA comprises one or more mutations.

10. The *Salmonella* Typhi vector of claim 9, wherein the mutation comprises one or more substitution mutations selected from D271A and R286A.

11. The *Salmonella* Typhi vector of claim 9, wherein OmpA comprises both D271A and R286A mutations.

12. The *Salmonella* Typhi vector of claim 1, wherein the S. Typhi overexpresses a cytolysin A (ClyA) protein to facilitate outer membrane vesicle formation.

13. The *Salmonella* Typhi vector of claim 12, wherein the ClyA is mutated to reduce hemolytic activity of ClyA.

14. The *Salmonella* Typhi vector of claim 13, wherein the ClyA mutant is selected from the group consisting of ClyA I198N, ClyA A199D, ClyA E204K, ClyA C285W and combinations thereof.

15. The *Salmonella* Typhi vector of claim 12, wherein the ClyA is a fusion protein.

16. The *Salmonella* Typhi vector of claim 15, wherein the ClyA comprises I198N, A199D, and E204K substitution mutations.

17. The *Salmonella* Typhi vector of claim 1, wherein the PagL amino acid sequence is selected from SEQ ID NO:2 and SEQ ID NO:4.

18. An immunogenic composition comprising a combination of the live *Salmonella* Typhi vectors according claim 1, wherein a first *Salmonella* Typhi vector expresses i) OmpA, an antigenic fragment thereof or a variant thereof from *Acinetobacter baumannii*; and ii) OmpW, an antigenic fragment thereof or a variant thereof from *Acinetobacter baumannii* and a second *Salmonella* Typhi vector expresses i) OmpA, an antigenic fragment thereof or a variant thereof from *Klebsiella pneumoniae*; and ii) OmpW, an antigenic fragment thereof or a variant thereof from *Klebsiella pneumoniae*.

19. An immunogenic composition comprising isolated recombinant outer membrane vesicles from the *Salmonella* Typhi of claim 1, comprising one or more heterologous antigens from a pathogen, wherein the heterologous antigen comprises an outer membrane protein, an antigenic fragment thereof or a variant thereof, wherein the *Salmonella* Typhi has been engineered to express the heterologous antigen.

20. An immunogenic composition comprising a combination of the isolated recombinant outer membrane vesicles of claim 19, wherein a first isolated recombinant outer membrane vesicle comprises i) OmpA, an antigenic fragment thereof or a variant thereof from *Acinetobacter baumannii*; and ii) OmpW, an antigenic fragment thereof or a variant thereof from *Acinetobacter baumannii* and a second isolated recombinant outer membrane vesicle comprises i) OmpA, an antigenic fragment thereof or a variant thereof from *Klebsiella pneumoniae*; and ii) OmpW, an antigenic fragment thereof or a variant thereof from *Klebsiella pneumoniae*.

* * * * *

```
SEQUENCE LISTING

<160> NUMBER OF SEQ ID NOS: 16

<210> SEQ ID NO 1
<211> LENGTH: 650
<212> TYPE: DNA
<213> ORGANISM: Artificial sequence
<220> FEATURE:
<223> OTHER INFORMATION: pagL

<400> SEQUENCE: 1
ggatccaatt gaaaataagg aggaaaaaat gactagtatg aagcgcatct ttatttatct      60
gttacttccg tgtgcattcg catgttctgc taatgataat gttttttttg gcaagggcaa     120
caagcatcag atctcttttg ctgcgggaga aagtataaga agaggagggg ttgagcactt     180
atatacggct tttctgacat acagtgaacc cagcgatttt ttcttttttac aggcaagaaa     240 taatctggag ttaggaggat ttaaggctaa gggtagcgat gattgcagta aacattctgg     300
cagcgttccc tgtaataaat ataaccaggg cgtattgggt atctcgaagg atgtggcgct     360
ggttcatttc gctggtatct ataccggtat tggtctgggg gcttatataa aatctaagtc     420
gcgagatgat atgcgtgtca attctgcatt tacctttgga gaaaaagcgt ttcttggctg     480
gaactttggg gcttttttcta cagaagctta tatccggcat ttctcgaatg gatcacttac     540
ggataaaaat tcagggcata attttgtagg tgcttcaatt agttataatt tctgataata     600
gttgataacc taggccgcct aatgagcggg cttttttttc tcgggctagc                 650

<210> SEQ ID NO 2
<211> LENGTH: 188
<212> TYPE: PRT
<213> ORGANISM: Salmonella enterica

<400> SEQUENCE: 2

Met Thr Ser Met Lys Arg Ile Phe Ile Tyr Leu Leu Leu Pro Cys Ala
1               5                   10                  15

Phe Ala Cys Ser Ala Asn Asp Asn Val Phe Phe Gly Lys Gly Asn Lys
                20                  25                  30

His Gln Ile Ser Phe Ala Ala Gly Glu Ser Ile Arg Arg Gly Val
            35                  40                  45
```

```
Glu His Leu Tyr Thr Ala Phe Leu Thr Tyr Ser Glu Pro Ser Asp Phe
    50              55                  60

Phe Phe Leu Gln Ala Arg Asn Asn Leu Glu Leu Gly Gly Phe Lys Ala
65              70                  75                  80

Lys Gly Ser Asp Asp Cys Ser Lys His Ser Gly Ser Val Pro Cys Asn
                85                  90                  95

Lys Tyr Asn Gln Gly Val Leu Gly Ile Ser Lys Asp Val Ala Leu Val
            100                 105                 110

His Phe Ala Gly Ile Tyr Thr Gly Ile Gly Leu Gly Ala Tyr Ile Lys
                115                 120                 125

Ser Lys Ser Arg Asp Asp Met Arg Val Asn Ser Ala Phe Thr Phe Gly
130                 135                 140

Glu Lys Ala Phe Leu Gly Trp Asn Phe Gly Ala Phe Ser Thr Glu Ala
145                 150                 155                 160

Tyr Ile Arg His Phe Ser Asn Gly Ser Leu Thr Asp Lys Asn Ser Gly
                165                 170                 175

His Asn Phe Val Gly Ala Ser Ile Ser Tyr Asn Phe
                180                 185
```

<210> SEQ ID NO 3
<211> LENGTH: 647
<212> TYPE: DNA
<213> ORGANISM: Artificial sequence
<220> FEATURE:
<223> OTHER INFORMATION: pagL

<400> SEQUENCE: 3

```
ggatccaatt gaaataagg aggaaaaagt gtatatgaag cgcatcttta tttatctgtt      60
acttccgtgt gcattcgcat gttctgctaa tgataatgtt tttttggca agggcaacaa     120 gcatcagatc tcttttgctg cgggagaaag tataagaaga ggaggggttg agcacttata    180
tacggctttt ctgacataca gtgaacccag cgattttttc ttttttacagg caagaaataa    240 tctggagtta ggaggattta aggctaaggg tagcgatgat tgcagtaaac attctggcag    300
cgttccctgt aataaatata accagggcgt attgggtatc tcgaaggatg tggcgctggt    360
tcatttcgct ggtatctata ccggtattgg tctgggggct tatataaaat ctaagtcgcg    420
agatgatatg cgtgtcaatt ctgcatttac ctttggagaa aaagcgtttc ttggctggaa    480
ctttggggct ttttctacag aagcttatat ccggcatttc tcgaatggat cacttacgga    540
taaaaattca gggcataatt ttgtaggtgc ttcaattagt tataatttct gataatagtt    600
gataacctag gccgcctaat gagcgggctt ttttttctcg ggctagc                  647
```

<210> SEQ ID NO 4
<211> LENGTH: 187
<212> TYPE: PRT
<213> ORGANISM: Salmonella enterica

<400> SEQUENCE: 4

```
Met Tyr Met Lys Arg Ile Phe Ile Tyr Leu Leu Pro Cys Ala Phe
1               5                   10                  15

Ala Cys Ser Ala Asn Asp Asn Val Phe Phe Gly Lys Gly Asn Lys His
                20                  25                  30

Gln Ile Ser Phe Ala Ala Gly Glu Ser Ile Arg Arg Gly Gly Val Glu
            35                  40                  45

His Leu Tyr Thr Ala Phe Leu Thr Tyr Ser Glu Pro Ser Asp Phe Phe
    50              55                  60
```

Phe Leu Gln Ala Arg Asn Asn Leu Glu Leu Gly Gly Phe Lys Ala Lys
65                  70                  75                  80

Gly Ser Asp Asp Cys Ser Lys His Ser Gly Ser Val Pro Cys Asn Lys
            85                  90                  95

Tyr Asn Gln Gly Val Leu Gly Ile Ser Lys Asp Val Ala Leu Val His
        100                 105                 110

Phe Ala Gly Ile Tyr Thr Gly Ile Gly Leu Gly Ala Tyr Ile Lys Ser
            115                 120                 125

Lys Ser Arg Asp Asp Met Arg Val Asn Ser Ala Phe Thr Phe Gly Glu
130                 135                 140

Lys Ala Phe Leu Gly Trp Asn Phe Gly Ala Phe Ser Thr Glu Ala Tyr
145                 150                 155                 160

Ile Arg His Phe Ser Asn Gly Ser Leu Thr Asp Lys Asn Ser Gly His
                165                 170                 175

Asn Phe Val Gly Ala Ser Ile Ser Tyr Asn Phe
            180                 185

<210> SEQ ID NO 5
<211> LENGTH: 655
<212> TYPE: DNA
<213> ORGANISM: Artificial sequence
<220> FEATURE:
<223> OTHER INFORMATION: pagL

<400> SEQUENCE: 5
ggatccaatt gctattgaca ttgaaatggt ggtggaatgt atatgaagag aatatttata      60
tatctattat taccttgtgc attcgcatgt tctgctaatg ataatgtttt ttttggcaag     120
ggcaacaagc atcagatctc ttttgctgcg ggagaaagta taagaagagg aggggttgag     180
cacttatata cggcttttct gacatacagt gaacccagcg attttttctt tttacaggca     240
agaaataatc tggagttagg aggatttaag gctaagggta gcgatgattg cagtaaacat     300
tctggcagcg ttccctgtaa taaatataac caggcgtat  tgggtatctc gaaggatgtg     360
gcgctggttc atttcgctgg tatctatacc ggtattggtc tggggcctta tataaaatct     420
aagtcgcgag atgatatgcg tgtcaattct gcatttacct tggagaaaa agcgtttctt     480 ggctggaact tggggctttt tctacagaa gcttatatcc ggcatttctc gaatggatca     540
cttacggata aaaattcagg gcataatttt gtaggtgctt caattagtta aatttctga     600 taatagttga taacctaggc cgcctaatga gcgggctttt ttttctcggg ctagc          655

<210> SEQ ID NO 6
<211> LENGTH: 6909
<212> TYPE: DNA
<213> ORGANISM: Artificial sequence
<220> FEATURE:
<223> OTHER INFORMATION: pagL

<400> SEQUENCE: 6
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcatttttg gggagaatgg acttgccgac tgattaatga gggttaatca     420

```
gtatgcagtg gcataaaaaa gcaaataaag gcatataaca gatcgatctt aaacatccac    480
aggaggatgg gatccaattg aaaataagga ggaaaaaatg actagtatga agcgcatctt    540
tatttatctg ttacttccgt gtgcattcgc atgttctgct aatgataatg tttttttttgg   600 caagggcaac aagcatcaga tctcttttgc tgcgggagaa agtataagaa gaggagggggt   660 tgagcactta tatacggctt ttctgacata cagtgaaccc agcgattttt tcttttttaca   720 ggcaagaaat aatctggagt taggaggatt taaggctaag ggtagcgatg attgcagtaa    780
acattctggc agcgttccct gtaataaata taaccagggc gtattgggta tctcgaagga    840
tgtggcgctg gttcatttcg ctggtatcta taccggtatt ggtctggggg cttatataaa    900
atctaagtcg cgagatgata tgcgtgtcaa ttctgcattt accttttggag aaaaagcgtt    960 tcttggctgg aactttgggg cttttttctac agaagcttat atccggcatt tctcgaatgg   1020
atcacttacg ataaaaatt cagggcataa ttttgtaggt gcttcaatta gttataattt    1080
ctgataatag ttgataaacct aggccgccta atgagcgggc ttttttttct cgggctagct   1140
gataacctag cccgcctaat gagcgggctt tttttctcg gcctaggttt cacctgttct    1200
attaggtgtt acatgctgtt catctgttac attgtcgatc tgttcatggt gaacagcttt   1260
aaatgcacca aaaactcgta aaagctctga tgtatctatc tttttttacac cgttttcatc   1320 tgtgcatatg gacagttttc cctttgatat ctaacggtga acagttgttc acttttgtt    1380 tgttagtctt gatgcttcac tgatagatac aagagccata agaacctcag atccttccgt   1440
atttagccag tatgttctct agtgtggttc gttgttttttg cgtgagccat gagaacgaac   1500
cattgagatc atgcttactt tgcatgtcac tcaaaaattt tgcctcaaaa ctggtgagct   1560 gaattttttgc agttaaagca tcgtgtagtg tttttcttag tccgttacgt aggtaggaat   1620
ctgatgtaat ggttgttggt attttgtcac cattcatttt tatctggttg ttctcaagtt   1680
cggttacgag atccatttgt ctatctagtt caacttggaa aatcaacgta tcagtcgggc   1740
ggcctcgctt atcaaccacc aatttcatat tgctgtaagt gtttaaatct ttacttattg   1800
gtttcaaaac ccattggtta agccttttaa actcatggta gttatttttca agcattaaca   1860 tgaacttaaa ttcatcaagg ctaatctcta tatttgcctt gtgagttttc ttttgtgtta   1920 gttctttttaa taaccactca taaatcctca tagagtattt gttttcaaaa gacttaacat   1980
gttccagatt atattttatg aatttttttta actggaaaag ataaggcaat atctcttcac   2040
taaaaactaa ttctaatttt tcgcttgaga acttggcata gtttgtccac tggaaaatct   2100
caaagccttt aaccaaagga ttcctgattt ccacagttct cgtcatcagc tctctggttg   2160
ctttagctaa tacaccataa gcattttccc tactgatgtt catcatctga gcgtattggt   2220
tataagtgaa cgataccgtc cgttctttcc ttgtagggtt tcaatcgtg ggttgagta    2280 gtgccacaca gcataaaatt agcttggttt catgctccgt taagtcatag cgactaatcg   2340
ctagttcatt tgcttgaaa acaactaatt cagacataca tctcaattgg tctaggtgat   2400
tttaatcact ataccaattg agatgggcta gtcaatgata attactagtc ctttttccttt   2460 gagttgtggg tatctgtaaa ttctgctaga cctttgctgg aaaacttgta aattctgcta   2520
gaccctctgt aaattccgct agacctttgt gtgtttttttt tgtttatatt caagtggtta   2580
taatttatag aataaagaaa gaataaaaaa agataaaaag aatagatccc agccctgtgt   2640
ataactcact actttagtca gttccgcagt attacaaaag gatgtcgcaa acgctgtttg   2700
ctcctctaca aaacagacct taaaacccta aaggcttaag tagcacccctc gcaagctcgg   2760
```

-continued

```
gcaaatcgct gaatattcct tttgtctccg accatcaggc acctgagtcg ctgtcttttt    2820
cgtgacattc agttcgctgc gctcacggct ctggcagtga atgggggtaa atggcactac    2880
aggcgccttt tatggattca tgcaaggaaa ctacccataa tacaagaaaa gcccgtcacg    2940
ggcttctcag ggcgttttat ggcgggtctg ctatgtggtg ctatctgact ttttgctgtt    3000
cagcagttcc tgccctctga ttttccagtc tgaccacttc ggattatccc gtgacaggtc    3060
attcagactg gctaatgcac ccagtaaggc agcggtatca tcaacaggct tacccgtctt    3120
actgtcaacc ggatctaaaa cactaggccc aagagtttgt agaaacgcaa aaaggccatc    3180
cgtcaggatg gccttctgct taatttgatg cctggcagtt tatggcgggc gtcctgcccg    3240
ccaccctccg ggccgttgct tcgcaacgtt caaatccgct cccggcggat ttgtcctact    3300
caggagagcg ttcaccgaca aacaacagat aaaacgaaag gcccagtctt tcgactgagc    3360
ctttcgtttt atttgatgcc tggcagttcc ctactctcgc atggggagac cccacactac    3420
catcggcgct acggcgtttc acttctgagt tcggcatggg gtcaggtggg accaccgcgc    3480
tactgccgcc aggcaaattc tgttttatca gaccgcttct gcgttctgat ttaatctgta    3540
tcaggctgaa aatcttctct catccgccaa aacagccaag ctggatctaa aacactagcc    3600
caaccttcta tagaaggcgg cggtggaatc gaaatctcgt gatggcaggt tgggcgtcgc    3660
ttggtcggtc atttcgaacc ccagagtccc gctcagaaga actcgtcaag aaggcgatag    3720
aaggcgatgc gctgcgaatc gggagcggcg ataccgtaaa gcacgaggaa gcggtcagcc    3780
cattcgccgc caagctcttc agcaatatca cgggtagcca acgctatgtc ctgatagcgg    3840
tccgccacac ccagccggcc acagtcgatg aatccagaaa agcggccatt ttccaccatg    3900
atattcggca agcaggcatc gccatgggtc acgacgagat cctcgccgtc gggcatgcgc    3960
gccttgagcc tggcgaacag ttcggctggc gcgagcccct gatgctcttc gtccagatca    4020
tcctgatcga caagaccggc ttccatccga gtacgtgctc gctcgatgcg atgtttcgct    4080
tggtggtcga atgggcaggt agccggatca agcgtatgca gccgccgcat tgcatcagcc    4140
atgatggata ctttctcggc aggagcaagg tgagatgaca ggagatcctg ccccggcact    4200
tcgcccaata gcagccagtc ccttcccgct tcagtgacaa cgtcgagcac agctgcgcaa    4260
ggaacgcccg tcgtggccag ccacgatagc cgcgctgcct cgtcctgcag ttcattcagg    4320
gcaccggaca ggtcggtctt gacaaaaaga accgggcgcc cctgcgctga cagccggaac    4380
acggcggcat cagagcagcc gattgtctgt tgtgcccagt catagccgaa tagcctctcc    4440
acccaagcgg ccggagaacc tgcgtgcaat ccatcttgtt caatcatgcg aaacgatcct    4500
catcctgtct cttgatcaga tcttgatccc ctgcgccatc agatccttgg cggcaagaaa    4560
gccatccagt ttactttgca gggcttccca accttaccag agggcgcccc agccgtggca    4620
attccggttc gctgctagac aacatcagca aggagaaagg ggctaccggc gaaccagcag    4680 ccccttttata aaggcgcttc agtagtcaga ccagcatcag tcctgaaaag gcgggcctgc    4740
gcccgcctcc aggttgctac ttaccggatt cgtaagccat gaaagccgcc acctccctgt    4800
gtccgtctct gtaacgaatc tcgcacagcg attttcgtgt cagataagtg aatatcaaca    4860
gtgtgagaca cacgatcaac acacaccaga caagggaact tcgtggtagt ttcatggcct    4920
tcttctcctt gcgcaaagcg cggtaagagg ctatcctgat gtggactaga catagggatg    4980
cctcgtggtg gttaatgaaa attaacttac tacgggcta tcttctttct gccacacaac    5040
acggcaacaa accaccttca cgtcatgagg cagaaagcct caagcgccgg gcacatcata    5100
gcccatatac ctgcacgctg accacactca ctttccctga aaataatccg ctcattcaga    5160
```

```
ccgttcacgg gaaatccgtg tgattgttgc cgcatcacgc tgcctccgg agtttgtctc      5220 gagcactttt gttacccgcc aaacaaaacc caaaaacaac ccatacccaa cccaataaaa      5280
caccaaaaca agacaaataa tcattgattg atggttgaaa tggggtaaac ttgacaaaca      5340
aacccactta aaacccaaaa catacccaaa cacacaccaa aaaaacacca taaggagttt      5400
tataaatgtt ggtattcatt gatgacggtt caacaaacat caaactacag tggcaggaaa      5460
gcgacggaac aattaaacag cacattagcc cgaacagctt caaacgcgag tgggcagtct      5520
cttttggtga taaaaaggtc tttaactaca cactgaacgg cgaacagtat tcatttgatc      5580
caatcagccc ggatgctgta gtcacaacca atatcgcatg gcaatacagc gacgttaatg      5640
tcgttgcagt gcatcacgcc ttactgacca gtggtctgcc ggtaagcgaa gtggatattg      5700
tttgcacact tcctctgaca gagtattacg acagaaataa ccaacccaat acggaaaata      5760
ttgagcgtaa gaaagcaaac ttccggaaaa aaattacatt aaatggcggg gatacattca      5820
caataaaaga tgtaaaagtc atgcctgaat ctataccggc aggttatgaa gttctacaag      5880
aactggatga gttagattct ttattaatta tagatctcgg gggcaccaca ttagatattt      5940
ctcaggtaat ggggaaatta tcggggatca gtaaaatata cggagactca tctcttggtg      6000
tctctctggt tacatctgca gtaaaagatg ccctttctct tgcgagaaca aaaggaagta      6060
gctatcttgc tgacgatata atcattcaca gaaaagataa taactatctg aagcaacgaa      6120
ttaatgatga gaacaaaata tcaatagtca ccgaagcaat gaatgaagca cttcgtaaac      6180
ttgagcaacg tgtattaaat acgctcaatg aattttctgg ttatactcat gttatggtta      6240
taggcggtgg cgcagaatta atatgcgatg cagtaaaaaa acacacacag attcgtgatg      6300
aacgtttttt caaaaccaat aactctcaat atgatttagt taacggtatg tatctcatag      6360
gtaattaatg atggacaagc gcagaaccat tgccttcaaa ctaaatccag atgtaaatca      6420
aacagataaa attgtttgtg atacactgga cagtatcccg caaggggaac gaagccgcct      6480
taaccgggcc gcactgacgg caggtctggc cttatacaga caagatcccc ggacccettt      6540 cctttatgt gagctgctga cgaaagaaac cacattttca gatatcgtga atatattgag      6600
atcgctattt ccaaaagaga tggccgattt taattcttca atagtcactc aatcctcttc      6660
acaacaagag caaaaagtg atgaagagac caaaaaaaat gcgatgaagc taataaatta      6720
attcaattat tattgagttc cctttatcca ctatcaggct ggataaaggg aactcaatca      6780
agttattttc ttaccagtca ttacataatc gttattatga aataatcgtt tgcactgtct      6840
ctgttattca ggcaatttca ataaaggcac ttgctcacgc tctgtcattt tctgaaactc      6900
ttcatgctg                                                             6909
```

<210> SEQ ID NO 7
<211> LENGTH: 1071
<212> TYPE: DNA
<213> ORGANISM: Acinetobacter baumannii

<400> SEQUENCE: 7

```
atgaaattga gtcgtattgc acttgctact atgcttgttg ctgctccatt agctgctgct       60
aatgctggcg taacagttac tccattattg ctttggttaca ctttccaaga cagccaacac      120
aacaatggcg gtaaagatgg taacttaact aacggtcctg agttacaaga cgatttattc      180
gttggcgcag ctcttggtat cgagttaact ccatggttag gtttcgaagc tgaatataac      240
caagttaaag gcgacgtaga cggcgcttct gctggtgctg aatataaaca aaaacaaatc      300
```

```
aacggtaact tctatgttac ttctgattta attactaaaa actacgacag caaaatcaag    360
ccgtacgtat tattaggtgc tggtcactat aaatacgact ttgatggcgt aaaccgtggt    420
acacgtggta actcagaaga aggtacttta ggtaacgctg tgttggtgc tttctggcgc     480
ttaaacgacg ctttatctct tcgtactgaa gctcgtgcta cttataatgc tgatgaagag    540
ttctggaact atacagctct tgctggctta aacgtagttc ttggtggtca cttgaagcct    600
gctgttcctg tagtagaagt tgctccagtt gaaccaactc cagttgctcc acaaccacaa    660
gagttaactg aagaccttaa catggaactt cgtgtgttct ttgatactaa caaatcaaac    720
atcaaagacc aatacaagcc agaaattgct aaagttgctg aaaaattatc tgaatacccT    780
aacgctactg cacgtatcga aggtcacaca gataacactg gtccacgtaa gttgaacgaa    840
cgtttatctt agctcgtgc taactctgtt aaatcagctc ttgtaaacga atacaacgtt     900
gatgcttctc gtttgtctac tcaaggtttc gcttgggatc aaccgattgc tgacaacaaa    960
actaaagaag gtcgtgctat gaaccgtcgt gtattcgcga caatcactgg tagccgtact   1020
gtagtagttc aacctggtca agaagcggca gctcctgcag cagctcaata a            1071
```

<210> SEQ ID NO 8
<211> LENGTH: 356
<212> TYPE: PRT
<213> ORGANISM: Acinetobacter baumannii

<400> SEQUENCE: 8

```
Met Lys Leu Ser Arg Ile Ala Leu Ala Thr Met Leu Val Ala Ala Pro
1               5                   10                  15

Leu Ala Ala Ala Asn Ala Gly Val Thr Val Thr Pro Leu Leu Leu Gly
                20                  25                  30

Tyr Thr Phe Gln Asp Ser Gln His Asn Asn Gly Gly Lys Asp Gly Asn
            35                  40                  45

Leu Thr Asn Gly Pro Glu Leu Gln Asp Asp Leu Phe Val Gly Ala Ala
        50                  55                  60

Leu Gly Ile Glu Leu Thr Pro Trp Leu Gly Phe Glu Ala Glu Tyr Asn
65                  70                  75                  80

Gln Val Lys Gly Asp Val Asp Gly Ala Ser Ala Gly Ala Glu Tyr Lys
                85                  90                  95

Gln Lys Gln Ile Asn Gly Asn Phe Tyr Val Thr Ser Asp Leu Ile Thr
            100                 105                 110

Lys Asn Tyr Asp Ser Lys Ile Lys Pro Tyr Val Leu Leu Gly Ala Gly
        115                 120                 125

His Tyr Lys Tyr Asp Phe Asp Gly Val Asn Arg Gly Thr Arg Gly Asn
    130                 135                 140

Ser Glu Glu Gly Thr Leu Gly Asn Ala Gly Val Gly Ala Phe Trp Arg
145                 150                 155                 160

Leu Asn Asp Ala Leu Ser Leu Arg Thr Glu Ala Arg Ala Thr Tyr Asn
                165                 170                 175

Ala Asp Glu Glu Phe Trp Asn Tyr Thr Ala Leu Ala Gly Leu Asn Val
            180                 185                 190

Val Leu Gly Gly His Leu Lys Pro Ala Val Pro Val Glu Val Ala
        195                 200                 205

Pro Val Glu Pro Thr Pro Val Ala Pro Gln Pro Gln Glu Leu Thr Glu
    210                 215                 220

Asp Leu Asn Met Glu Leu Arg Val Phe Phe Asp Thr Asn Lys Ser Asn
225                 230                 235                 240
```

Ile Lys Asp Gln Tyr Lys Pro Glu Ile Ala Lys Val Ala Glu Lys Leu
        245                 250                 255

Ser Glu Tyr Pro Asn Ala Thr Ala Arg Ile Glu Gly His Thr Asp Asn
            260                 265                 270

Thr Gly Pro Arg Lys Leu Asn Glu Arg Leu Ser Leu Ala Arg Ala Asn
        275                 280                 285

Ser Val Lys Ser Ala Leu Val Asn Glu Tyr Asn Val Asp Ala Ser Arg
    290                 295                 300

Leu Ser Thr Gln Gly Phe Ala Trp Asp Gln Pro Ile Ala Asp Asn Lys
305                 310                 315                 320

Thr Lys Glu Gly Arg Ala Met Asn Arg Arg Val Phe Ala Thr Ile Thr
                325                 330                 335

Gly Ser Arg Thr Val Val Gln Pro Gly Gln Glu Ala Ala Ala Pro
            340                 345                 350

Ala Ala Ala Gln
        355

<210> SEQ ID NO 9
<211> LENGTH: 591
<212> TYPE: DNA
<213> ORGANISM: Acinetobacter baumannii

<400> SEQUENCE: 9
gtgttcaaaa aagctttggt tattgcatta atggggatgt cttcttttac ttttgctggt      60
aactggcaag tgaaatttgg tggtagtgtt attgctccat ctgaagatac accaacacct     120
ttaggcgtgg taaaagcaga tcatgaatat gcatttacac catcagtaga atactttttt     180
ggtcagtctc catttcggc agaattatta ttagcaacgc ctattaatca tgatgtattg      240
ctagatggta aaaatgcagc acgtataaaa caattaccac caataattac tgcaaaatat     300
cattttaaaa actctacacg tttcacaccg tatattggta ttggtgctac agcatttatt     360
ccttgggatg aagaaggggc agcggtaaag gttaaagaag attttggttt ggcaggtcaa     420
gttggtttta atttccaacc tgctgatgct aaaaactggg gtgtatttgt agatgtacgt     480
tatgctgata ttagtccgga agtaacaatt gatccatcaa ttgctaacta caagtttgat     540
ctagatatta atccttttgt ttatactttg ggttatagct ataaaattta a              591

<210> SEQ ID NO 10
<211> LENGTH: 196
<212> TYPE: PRT
<213> ORGANISM: Acinetobacter baumannii

<400> SEQUENCE: 10

Met Phe Lys Lys Ala Leu Val Ile Ala Leu Met Gly Met Ser Ser Phe
1               5                   10                  15

Thr Phe Ala Gly Asn Trp Gln Val Lys Phe Gly Gly Ser Val Ile Ala
            20                  25                  30

Pro Ser Glu Asp Thr Pro Thr Pro Leu Gly Val Val Lys Ala Asp His
        35                  40                  45

Glu Tyr Ala Phe Thr Pro Ser Val Glu Tyr Phe Phe Gly Gln Ser Pro
    50                  55                  60

Phe Ser Ala Glu Leu Leu Leu Ala Thr Pro Ile Asn His Asp Val Leu
65                  70                  75                  80

Leu Asp Gly Lys Asn Ala Ala Arg Ile Lys Gln Leu Pro Pro Ile Ile
                85                  90                  95

Thr Ala Lys Tyr His Phe Lys Asn Ser Thr Arg Phe Thr Pro Tyr Ile

```
            100                 105                 110
Gly Ile Gly Ala Thr Ala Phe Ile Pro Trp Asp Glu Glu Gly Ala Ala
        115                 120                 125

Val Lys Val Lys Glu Asp Phe Gly Leu Ala Gly Gln Val Gly Phe Asn
    130                 135                 140

Phe Gln Pro Ala Asp Ala Lys Asn Trp Gly Val Phe Val Asp Val Arg
145                 150                 155                 160

Tyr Ala Asp Ile Ser Pro Glu Val Thr Ile Asp Pro Ser Ile Ala Asn
                165                 170                 175

Tyr Lys Phe Asp Leu Asp Ile Asn Pro Phe Val Tyr Thr Leu Gly Tyr
            180                 185                 190

Ser Tyr Lys Phe
        195

<210> SEQ ID NO 11
<211> LENGTH: 1071
<212> TYPE: DNA
<213> ORGANISM: Klebsiella pneumoniae

<400> SEQUENCE: 11
atgaaaaaga cagctatcgc gattgcagtg gcactggctg gcttcgctac cgtagcgcag        60
gccgctccga agataacac ctggtatgca ggtggtaaac tgggttggtc ccagtatcac        120
gacaccggtt tctacggtaa cggtttccag aacaacaacg tccgacccg taacgatcag        180 cttggtgctg gtgcgttcgg tggttaccag gttaacccgt acctcggttt cgaaatgggt       240
tatgactggc tgggccgtat ggcatataaa ggcagcgttg acaacggtgc tttcaaagct       300
cagggcgttc agctgaccgc taaactgggt tacccgatca ctgacgatct ggacatctac       360
acccgtctgg gcggcatggt ttggcgcgct gactccaaag caactacgc ttctaccggc        420 gtttcccgta gcgaacacga cactggcgtt tccccagtat ttgctggcgg cgtagagtgg       480
gctgttactc gtgacatcgc tacccgtctg aataccagt gggttaacaa catcggcgac        540
gcgggcactg tgggtacccg tcctgataac ggcatgctga gcctgggcgt tcctaccgc        600 ttcggtcagg aagatgctgc accggttgtt gctccggctc cggctccggc tccggaagtg       660
gctaccaagc acttcaccct gaagtctgac gttctgttca acttcaacaa agctaccctg       720
aaaccggaag tcagcaggc tctggatcag ctgtacactc agctgagcaa catggatccg        780
aaagacggtt ccgctgttgt tctgggctac accgaccgca tcggttccga agcttacaac       840
cagcagctgt ctgagaaacg tgctcagtcc gttgttgact acctggttgc taaaggcatc       900
ccggctggca aaatctccgc tcgcggcatg ggtgaatcca cccggttac tggcaacacc        960 tgtgacaacg tgaaagctcg cgctgccctg atcgattgcc tggctccgga tcgtcgtgta      1020
gagatcgaag ttaaaggcta caagaagtt gtaactcagc cggcggctta a               1071

<210> SEQ ID NO 12
<211> LENGTH: 356
<212> TYPE: PRT
<213> ORGANISM: Klebsiella pneumoniae

<400> SEQUENCE: 12

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Gly
            20                  25                  30

Lys Leu Gly Trp Ser Gln Tyr His Asp Thr Gly Phe Tyr Gly Asn Gly
```

```
                35                  40                  45
Phe Gln Asn Asn Asn Gly Pro Thr Arg Asn Asp Gln Leu Gly Ala Gly
 50                  55                  60

Ala Phe Gly Gly Tyr Gln Val Asn Pro Tyr Leu Gly Phe Glu Met Gly
 65                  70                  75                  80

Tyr Asp Trp Leu Gly Arg Met Ala Tyr Lys Gly Ser Val Asp Asn Gly
                 85                  90                  95

Ala Phe Lys Ala Gln Gly Val Gln Leu Thr Ala Lys Leu Gly Tyr Pro
            100                 105                 110

Ile Thr Asp Asp Leu Asp Ile Tyr Thr Arg Leu Gly Gly Met Val Trp
        115                 120                 125

Arg Ala Asp Ser Lys Gly Asn Tyr Ala Ser Thr Gly Val Ser Arg Ser
    130                 135                 140

Glu His Asp Thr Gly Val Ser Pro Val Phe Ala Gly Gly Val Glu Trp
145                 150                 155                 160

Ala Val Thr Arg Asp Ile Ala Thr Arg Leu Glu Tyr Gln Trp Val Asn
                165                 170                 175

Asn Ile Gly Asp Ala Gly Thr Val Gly Thr Arg Pro Asp Asn Gly Met
            180                 185                 190

Leu Ser Leu Gly Val Ser Tyr Arg Phe Gly Gln Glu Asp Ala Ala Pro
        195                 200                 205

Val Val Ala Pro Ala Pro Ala Pro Glu Val Ala Thr Lys His
    210                 215                 220

Phe Thr Leu Lys Ser Asp Val Leu Phe Asn Phe Asn Lys Ala Thr Leu
225                 230                 235                 240

Lys Pro Glu Gly Gln Gln Ala Leu Asp Gln Leu Tyr Thr Gln Leu Ser
                245                 250                 255

Asn Met Asp Pro Lys Asp Gly Ser Ala Val Val Leu Gly Tyr Thr Asp
            260                 265                 270

Arg Ile Gly Ser Glu Ala Tyr Asn Gln Gln Leu Ser Glu Lys Arg Ala
        275                 280                 285

Gln Ser Val Val Asp Tyr Leu Val Ala Lys Gly Ile Pro Ala Gly Lys
    290                 295                 300

Ile Ser Ala Arg Gly Met Gly Glu Ser Thr Pro Val Thr Gly Asn Thr
305                 310                 315                 320

Cys Asp Asn Val Lys Ala Arg Ala Ala Leu Ile Asp Cys Leu Ala Pro
                325                 330                 335

Asp Arg Arg Val Glu Ile Glu Val Lys Gly Tyr Lys Glu Val Val Thr
            340                 345                 350

Gln Pro Ala Ala
        355

<210> SEQ ID NO 13
<211> LENGTH: 639
<212> TYPE: DNA
<213> ORGANISM: Klebsiella pneumoniae

<400> SEQUENCE: 13
atgaagaagt tagcagcggc ggcattgatt cttggcacgc tttctaccgg cagcgtctgg      60
gcgcatgagg cgggggagtt tttcattcgt gccgggaccg ccaccgtccg accgacggag     120
ggctctgaca atgtgttagg cagccttggc agtttcaacg tcagtaacaa tacccagctg     180
ggtttaacct ttacctatat ggcgaccgat aacattggcg tggagttgct tgccgcgacg     240
ccgttccgcc ataaggtcgg caccgggcca accgggacta tcgccaccgt ccatcagctg     300
```

```
ccgcccaccc tgatggcgca gtggtacttt ggcgatgcgc aaagcaaggt gcgcccgtac    360 gtggggccg gtatcaacta caccaccttc tttaatgaag actttaacga taccggcaag     420 gcggccggc tttccgatct gagcctgaag gactcctggg gcgcggcggg gcaggtcggc     480
ctcgattatc tgattaaccg cgactggctg ctgaatatgt cggtgtggta catggatatc    540
gataccgatg tgaaattcaa agccggcggc gtggaccaga aagtcagcac ccgtctggat    600
ccgtgggtgt ttatgttctc cgcaggctat cggttctaa                          639
```

<210> SEQ ID NO 14
<211> LENGTH: 212
<212> TYPE: PRT
<213> ORGANISM: Klebsiella pneumoniae

<400> SEQUENCE: 14

```
Met Lys Lys Leu Ala Ala Ala Leu Ile Leu Gly Thr Leu Ser Thr
1               5                   10                  15

Gly Ser Val Trp Ala His Glu Ala Gly Glu Phe Phe Ile Arg Ala Gly
            20                  25                  30

Thr Ala Thr Val Arg Pro Thr Glu Gly Ser Asp Asn Val Leu Gly Ser
        35                  40                  45

Leu Gly Ser Phe Asn Val Ser Asn Asn Thr Gln Leu Gly Leu Thr Phe
    50                  55                  60

Thr Tyr Met Ala Thr Asp Asn Ile Gly Val Glu Leu Leu Ala Ala Thr
65                  70                  75                  80

Pro Phe Arg His Lys Val Gly Thr Gly Pro Thr Gly Thr Ile Ala Thr
                85                  90                  95

Val His Gln Leu Pro Pro Thr Leu Met Ala Gln Trp Tyr Phe Gly Asp
            100                 105                 110

Ala Gln Ser Lys Val Arg Pro Tyr Val Gly Ala Gly Ile Asn Tyr Thr
        115                 120                 125

Thr Phe Phe Asn Glu Asp Phe Asn Asp Thr Gly Lys Ala Ala Gly Leu
    130                 135                 140

Ser Asp Leu Ser Leu Lys Asp Ser Trp Gly Ala Ala Gly Gln Val Gly
145                 150                 155                 160

Leu Asp Tyr Leu Ile Asn Arg Asp Trp Leu Leu Asn Met Ser Val Trp
                165                 170                 175

Tyr Met Asp Ile Asp Thr Asp Val Lys Phe Lys Ala Gly Gly Val Asp
            180                 185                 190

Gln Lys Val Ser Thr Arg Leu Asp Pro Trp Val Phe Met Phe Ser Ala
        195                 200                 205

Gly Tyr Arg Phe
    210
```

<210> SEQ ID NO 15
<211> LENGTH: 921
<212> TYPE: DNA
<213> ORGANISM: Artificial sequence
<220> FEATURE:
<223> OTHER INFORMATION: ClyA

<400> SEQUENCE: 15

```
atgactagta tttttgcaga acaaactgta gaggtagtta aaagcgcgat cgaaaccgca    60 gatgggggcat tagatcttta taacaaatac ctcgaccagg tcatcccctg gaagaccttt    120
gatgaaacca taaagagtt aagccgtttt aaacaggagt actcgcagga agcttctgtt    180
```

-continued

```
ttagttggtg atattaaagt tttgcttatg gacagccagg acaagtattt tgaagcgaca      240
caaactgttt atgaatggtg tggtgtcgtg acgcaattac tctcagcgta tattttacta      300
tttgatgaat ataatgagaa aaaagcatca gcccagaaag acattctcat taggatatta      360
gatgatggtg tcaagaaact gaatgaagcg caaaaatctc tcctgacaag ttcacaaagt      420
ttcaacaacg cttccggaaa actgctggca ttagatagcc agttaactaa tgattttcg       480 gaaaaaagta gttatttcca gtcacaggtg gatagaattc gtaaggaagc ttatgccggt      540
gctgcagccg gcatagtcgc cggtccgttt ggattaatta tttcctattc tattgctgcg      600
ggcgtgattg aagggaaatt gattccagaa ttgaataaca ggctaaaaac agtgcaaaat      660
ttctttacta gcttatcagc tacagtgaaa caagcgaata agatatcga tgcggcaaaa      720 ttgaaattag ccactgaaat agcagcaatt ggggagataa aacggaaac cgaaacaacc       780 agattctacg ttgattatga tgatttaatg ctttctttat taaaaggagc tgcaaagaaa      840
atgattaaca cctgtaatga ataccaacaa cgtcatggta agaagacgct tttcgaggtt      900
cctgacgtcg ctagctgata a                                                921
```

<210> SEQ ID NO 16
<211> LENGTH: 305
<212> TYPE: PRT
<213> ORGANISM: Salmonella enterica

<400> SEQUENCE: 16

```
Met Thr Ser Ile Phe Ala Glu Gln Thr Val Glu Val Lys Ser Ala
1               5                   10                  15

Ile Glu Thr Ala Asp Gly Ala Leu Asp Leu Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
        50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240
```

-continued

```
Leu Lys Leu Ala Thr Glu Ile Ala Ala Ile Gly Glu Ile Lys Thr Glu
            245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser
305
```